(12) United States Patent
McCullough et al.

(10) Patent No.: US 10,646,652 B2
(45) Date of Patent: May 12, 2020

(54) CONTROLLABLE DRUG DELIVERY SYSTEM AND METHOD OF USE

(71) Applicant: AMGEN INC., Thousand Oaks, CA (US)

(72) Inventors: Adam B. McCullough, Westlake Village, CA (US); Ferry Tamtoro, San Ramon, CA (US); Huaying Yang, Vernon Hills, IL (US); Mark Ka Lai Lee, Newbury Park, CA (US); Desheng Yin, Thousand Oaks, CA (US); Scott R. Gibson, Granada Hills, CA (US); Donald Busby, Thousand Oaks, CA (US); Peter V. Shultz, Woodland Hills, CA (US); Keith P. Kogler, Simi Valley, CA (US); Basel Hasan Taha, Westlake Village, CA (US); Jimmie L. Ward, Golden, CO (US); Christopher R. Folk, Los Angeles, CA (US); Steven William Badelt, Los Angeles, CA (US)

(73) Assignee: AMGEN INC., Thousand Oaks, CA (US)

( * ) Notice: Subject to any disclaimer, the term of this patent is extended or adjusted under 35 U.S.C. 154(b) by 44 days.

(21) Appl. No.: 15/315,829

(22) PCT Filed: Jun. 3, 2015

(86) PCT No.: PCT/US2015/033933
§ 371 (c)(1),
(2) Date: Dec. 2, 2016

(87) PCT Pub. No.: WO2015/187797
PCT Pub. Date: Dec. 10, 2015

(65) Prior Publication Data
US 2017/0119969 A1    May 4, 2017

Related U.S. Application Data
(60) Provisional application No. 62/007,007, filed on Jun. 3, 2014.

(51) Int. Cl.
*A61M 5/20* (2006.01)
*A61M 5/315* (2006.01)
(Continued)

(52) U.S. Cl.
CPC .......... *A61M 5/20* (2013.01); *A61M 5/14244* (2013.01); *A61M 5/14248* (2013.01);
(Continued)

(58) Field of Classification Search
CPC .. A61M 2005/3267; A61M 2205/3331; A61M 2205/3368; A61M 2205/3553;
(Continued)

(56) References Cited

U.S. PATENT DOCUMENTS 3,485,239 A    12/1969 Vanderbeck
4,810,248 A     3/1989 Masters et al.
(Continued)

FOREIGN PATENT DOCUMENTS

CN    102413855 A    4/2012
CN    102905742 A    1/2013
(Continued)

OTHER PUBLICATIONS

International Search Report and a Written Opinion for Application No. PCT/US2015/033933, dated Nov. 5, 2015.
(Continued)

*Primary Examiner* — Imani N Hayman
(74) *Attorney, Agent, or Firm* — Marshall, Gerstein & Borun LLP

(57) ABSTRACT

A drug delivery system is disclosed that includes a drug delivery device having a reservoir, a delivery cannula having
(Continued)

a proximal end in fluid communication with the reservoir and a distal end to be received within a patient, and one or more controllable elements. The drug delivery system may further include one or more sensors coupled to the drug delivery device, and a controller coupled to the one or more sensors and the one or more controllable elements. The controller may be configured to use the one or more sensors to determine a condition or an operational state of the drug delivery device. Furthermore, the controller may be configured to control the controllable element based on the condition or the operational state of the drug delivery device and/or identity information stored in a memory onboard the device. A method for use with a drug delivery device is also disclosed.

16 Claims, 17 Drawing Sheets

(51) Int. Cl.
    *A61M 5/32*     (2006.01)
    *A61M 5/142*     (2006.01)
    *G06Q 50/22*     (2018.01)
    *A61M 5/50*     (2006.01)
    *G06F 19/00*     (2018.01)
    *G06Q 50/00*     (2012.01)
    *A61M 5/158*     (2006.01)
    *A61M 5/24*     (2006.01)

(52) U.S. Cl.
    CPC .............. *A61M 5/158* (2013.01); *A61M 5/24* (2013.01); *A61M 5/31501* (2013.01); *A61M 5/31568* (2013.01); *A61M 5/3202* (2013.01); *A61M 5/326* (2013.01); *A61M 5/3243* (2013.01); *A61M 5/3257* (2013.01); *A61M 5/5086* (2013.01); *G06F 19/325* (2013.01); *G06F 19/3418* (2013.01); *G06F 19/3468* (2013.01); *G06Q 50/01* (2013.01); *G06Q 50/22* (2013.01); *A61M 2005/3267* (2013.01); *A61M 2205/3331* (2013.01); *A61M 2205/3368* (2013.01); *A61M 2205/3553* (2013.01); *A61M 2205/3576* (2013.01); *A61M 2205/50* (2013.01); *A61M 2205/502* (2013.01); *A61M 2205/52* (2013.01); *A61M 2205/581* (2013.01); *A61M 2205/6009* (2013.01)

(58) Field of Classification Search
    CPC ...... A61M 2205/3576; A61M 2205/50; A61M 2205/502; A61M 2205/52; A61M 2205/581; A61M 2205/6009; A61M 5/14244; A61M 5/14248; A61M 5/158; A61M 5/20; A61M 5/24; A61M 5/31501; A61M 5/31568; A61M 5/3202; A61M 5/3243; A61M 5/3257; A61M 5/326; G06F 19/325; G06F 19/3418; G06F 19/3468; G06Q 50/01; G06Q 50/22
    See application file for complete search history.

(56) References Cited

U.S. PATENT DOCUMENTS

| | | | |
|---|---|---|---|
| 5,658,250 | A | 8/1997 | Blomquist et al. |
| 6,547,755 | B1* | 4/2003 | Lippe .................. A61M 5/20 604/154 |
| 7,004,928 | B2 | 2/2006 | Aceti et al. |
| 7,303,549 | B2 | 12/2007 | Flaherty et al. |
| 9,089,650 | B2 | 7/2015 | Nielsen et al. |
| 10,010,676 | B2 | 7/2018 | Bureau |
| 10,070,822 | B2 | 9/2018 | Terashima et al. |
| 2002/0072733 | A1 | 6/2002 | Flaherty |
| 2005/0182358 | A1 | 8/2005 | Veit et al. |
| 2006/0263839 | A1 | 11/2006 | Ward et al. |
| 2007/0106218 | A1 | 5/2007 | Yodfat et al. |
| 2007/0179448 | A1 | 8/2007 | Lim et al. |
| 2008/0014550 | A1 | 1/2008 | Jones et al. |
| 2008/0119705 | A1 | 5/2008 | Patel et al. |
| 2008/0160492 | A1 | 7/2008 | Campbell et al. |
| 2009/0093788 | A1 | 4/2009 | Sanchez, Jr. et al. |
| 2009/0192443 | A1* | 7/2009 | Collins, Jr. .......... A61M 11/005 604/24 |
| 2009/0259194 | A1 | 10/2009 | Pinedjian et al. |
| 2010/0211005 | A1 | 8/2010 | Edwards et al. |
| 2010/0262117 | A1 | 10/2010 | Magni et al. |
| 2010/0268190 | A1 | 10/2010 | Mielenz |
| 2011/0081888 | A1 | 4/2011 | Waniss |
| 2011/0178462 | A1 | 7/2011 | Moberg et al. |
| 2011/0270188 | A1 | 11/2011 | Caffey et al. |
| 2011/0313350 | A1 | 12/2011 | Krulevitch et al. |
| 2011/0313395 | A1 | 12/2011 | Krulevitch et al. |
| 2012/0066140 | A1 | 3/2012 | Hegeman et al. |
| 2012/0078181 | A1 | 3/2012 | Smith et al. |
| 2012/0232520 | A1 | 9/2012 | Sloan et al. |
| 2013/0079708 | A1 | 3/2013 | Wimpenny et al. |
| 2013/0184640 | A1 | 7/2013 | Li |
| 2013/0184649 | A1 | 7/2013 | Edwards et al. |
| 2013/0204227 | A1 | 8/2013 | Bochenko et al. |
| 2013/0236872 | A1 | 9/2013 | Laurusonis et al. |
| 2013/0261561 | A1 | 10/2013 | Deberadine |
| 2013/0310756 | A1 | 11/2013 | Whalley et al. |
| 2013/0317753 | A1 | 11/2013 | Kamen et al. |
| 2014/0012229 | A1 | 1/2014 | Bokelman et al. |
| 2014/0088554 | A1 | 3/2014 | Li et al. |
| 2014/0128843 | A1 | 5/2014 | Baker et al. |
| 2014/0207099 | A1 | 7/2014 | Nagar et al. |
| 2014/0243749 | A1 | 8/2014 | Edwards et al. |
| 2016/0030683 | A1 | 2/2016 | Taylor et al. |
| 2017/0098058 | A1 | 4/2017 | McCullough et al. |
| 2017/0103186 | A1 | 4/2017 | McCullough et al. |
| 2017/0124284 | A1 | 5/2017 | McCullough et al. |
| 2017/0124285 | A1 | 5/2017 | McCullough et al. |

FOREIGN PATENT DOCUMENTS

| | | |
|---|---|---|
| CN | 103108665 A | 5/2013 |
| CN | 103285448 A | 9/2013 |
| CN | 103491996 A | 1/2014 |
| CN | 103648552 A | 3/2014 |
| CN | 103702697 A | 4/2014 |
| EP | 1640029 A1 | 3/2006 |
| EP | 2537546 A1 | 12/2012 |
| EP | 2567662 A1 | 3/2013 |
| JP | 2006-524069 A | 10/2006 |
| JP | 2011-500154 A | 1/2011 |
| JP | 2012/508081 A | 4/2012 |
| JP | 2014-507963 A | 4/2014 |
| JP | 2015-513352 A | 5/2015 |
| JP | 2016-512144 A | 4/2016 |
| WO | WO-99/07425 A1 | 2/1999 |
| WO | WO-9907425 A1 | 2/1999 |
| WO | WO-2002/056822 A1 | 7/2002 |
| WO | WO-2006/134153 A1 | 12/2006 |
| WO | WO-2007/075677 A2 | 7/2007 |
| WO | WO-2007075677 A2 | 7/2007 |
| WO | WO-2007/088444 A1 | 8/2007 |
| WO | WO-2007088444 A1 | 8/2007 |
| WO | WO-2007/126851 A2 | 11/2007 |
| WO | WO-2008114218 A2 | 9/2008 |
| WO | WO-2009/125582 A1 | 10/2009 |
| WO | WO-2010/037828 A1 | 4/2010 |
| WO | WO-2010/052849 A1 | 5/2010 |
| WO | WO-2010/135184 A1 | 11/2010 |
| WO | WO-2011/005634 A1 | 1/2011 |
| WO | WO-2011097487 | 8/2011 |
| WO | WO-2012/127046 A2 | 9/2012 |
| WO | WO-2012/152628 A1 | 11/2012 |
| WO | WO-2012/160163 A1 | 11/2012 |
| WO | WO-2013/050535 A2 | 4/2013 |

(56) References Cited

FOREIGN PATENT DOCUMENTS

| WO | WO-2013/065055 A1 | 5/2013 |
|---|---|---|
| WO | WO-2013/160152 A1 | 10/2013 |
| WO | WO-2014/037331 A1 | 3/2014 |
| WO | WO-2014/064691 A2 | 5/2014 |
| WO | WO-2014066256 A1 | 5/2014 |

OTHER PUBLICATIONS

International Search Report and Written Opinion for Application No. PCT/US2015/033925, dated Nov. 3, 2015.
International Search Report and Written Opinion for International Application No. PCT/US2015/033939, dated Sep. 10, 2015.
"Omnipod Insulin Management System—UserGuide", Jan. 2008 (Jan. 1, 2008), XP055209058, Bedford, MA, USA Retrieved from the Internet: https://www.myomnipod.com/patient_guides/first_gen_user_guide_EN.pdf [retrieved on Aug. 21, 2015].
International Search Report and Written Opinion for Application No. PCT/US2015/033935, dated Aug. 12, 2015.
International Preliminary Report on Patentability and Written Opinion for International Application No. PCT/US2015/033935, dated Dec. 6, 2016.
International Preliminary Report on Patentability and Written Opinion for International Application No. PCT/US2015/033946, dated Dec. 6, 2016.
International Preliminary Report on Patentability and Written Opinion for International Application No. PCT/US2015/033925, dated Dec. 6, 2016.
International Preliminary Report on Patentability and Written Opinion for International Application No. PCT/US2015/033933, dated Dec. 6, 2016.
International Preliminary Report on Patentability and Written Opinion for International Application No. PCT/US2015/033939, dated Dec. 6, 2016.
Written Opinion for Singapore Application No. 11201609963P, dated Sep. 26, 2017.
International Application No. PCT/US2015/033946, International Search Report and Written Opinion, dated Feb. 26, 2016.
Singapore Patent Application No. 11201609970V, Written Opinion, dated Nov. 8, 2017.
Singapore Patent Application No. 11201609972R, Written Opinion, dated Nov. 7, 2017.
Written Opinion and Search Report issued in counterpart Singaporean Application No. 11201609966S, dated Feb. 1, 2018.
Australian Patent Application No. 2015271676, Examination Report No. 1, dated Mar. 25, 2019.
Australian Patent Application No. 2015271767, Examination Report No. 1, dated Mar. 16, 2019.
Chinese Patent Application No. 201580029198.9, Second Office Action, dated Mar. 1, 2019.
Chinese Patent Application No. 201580029455.9, Office Action, dated Mar. 4, 2019.
European Patent Application No. 15730345.4, Communication pursuant to Article 94(3) EPC, dated Feb. 6, 2019.
"The New OmniPod PDM", DiaTribe Learn Making Sense of Diabetes, Jun. 30, 2009.
Chinese Patent Application No. 201580029198.9, Official Action (translation) dated Aug. 20, 2018.
Singapore Patent Application No. 11201609963P, Examination Report, dated May 30, 2018.
Singapore Patent Application No. 11201609970V, Examination Report, dated May 30, 2018.
Singapore Patent Application No. 11201609972R, Examination Report, dated May 30, 2018.
U.S. Appl. No. 15/315,817, Nonfinal Office Action, dated Dec. 21, 2018.
U.S. Appl. No. 15/315,922, Nonfinal Office Action, dated Dec. 31, 2018.
Chinese Patent Application No. 201580029198.9, Decision of Rejection, dated Aug. 8, 2019.
European Patent Application No. 15728736.8, Communication Pursuant to Rule 164(2) and Article 94(3) EPC, dated Aug. 21, 2019.
European Patent Application No. 15729033.9, Communication Pursuant to Article 94(3) EPC, dated Jun. 19, 2019.
"Bar code technology in healthcare", Wikipedia entry, retrieved from the Internet at: <//en.wikipedia.org/w/index.php?title-Barcode_technology_in_healthcare&oldid=580283863> (Nov. 5, 2013).
Australian Patent Application No. 2015271763, Examination Report No. 1, dated May 18, 2019.
Chinese Patent Application No. 201580028862.8, First Office Action, dated Apr. 12, 2019.
Chinese Patent Application No. 201580029453.X, First Office Action, dated Apr. 16, 2019.
European Patent Application No. 15728737.6, Communication Pursuant to Article 94(3) EPC, dated May 17, 2019.
Japanese Patent Application No. 2016-570990, Notice of Reasons of Rejection, dated Apr. 2, 2019.
Japanese Patent Application No. 2016-570991, Notice of Rejection, dated Apr. 2, 2019.
Japanese Patent Application No. 2016-571023, Notice of Rejection, dated Apr. 2, 2019.
Japanese Patent Application No. 2016-571049, Notice of Rejection, dated May 21, 2019.
U.S. Appl. No. 15/315,817, Final Office Action, dated Jun. 12, 2019.
U.S. Appl. No. 15/315,922, Final Office Action, dated Oct. 1, 2019.
Australian Patent Application No. 2015271676, Examination Report No. 2, dated Nov. 15, 2019.
Australian Patent Application No. 2015271769, Examination Report No. 1, dated Oct. 23, 2019.
Australian Patent Application No. 2015271767, Examination Report No. 2, dated Nov. 29, 2019.
Chinese Patent Application No. 201580029455.9, Second Office Action, dated Dec. 18, 2019.
Israel Patent Application No. 248731, Office Action, dated Dec. 12, 2019.
Israel Patent Application No. 248756, Office Action, dated Dec. 26, 2019.

* cited by examiner

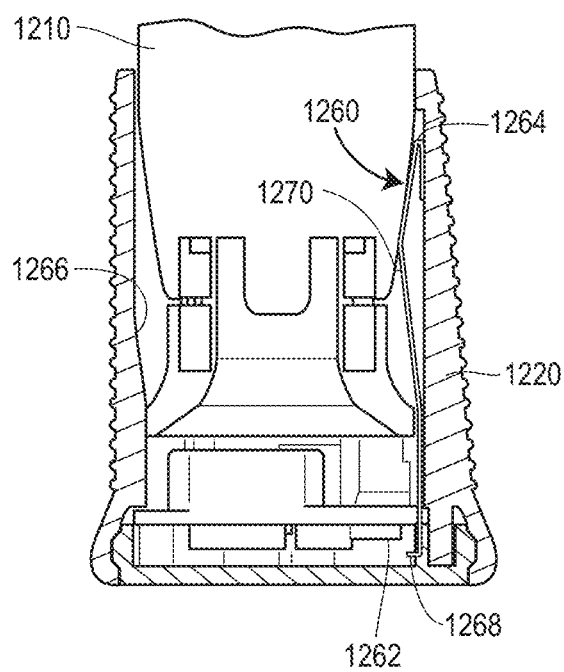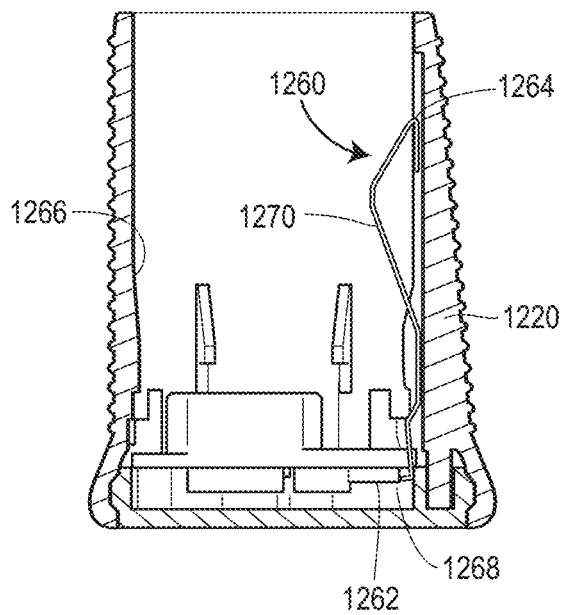
*FIG. 22*   *FIG. 23*

CONTROLLABLE DRUG DELIVERY SYSTEM AND METHOD OF USE

CROSS-REFERENCE TO RELATED APPLICATION

This is the United States national phase of International Application No. PCT/US2015/033933, having an international filing date of Jun. 3, 2015, which claims the priority benefit of U.S. Provisional Patent Application No. 62/007,007, filed Jun. 3, 2014. The contents of each of the foregoing is expressly incorporated herein by reference in the entirety.

BACKGROUND

The present disclosure generally relates to systems and methods for use with drug delivery devices relating to control of the drug delivery devices according to information representative of a condition or operational state of the drug delivery devices.

Drugs can be administered through the use of drug delivery devices, such as autoinjectors or on-body injectors or infusers. These devices may replace older delivery systems using the combination of a syringe and a vial containing the drug or medicament, or a pre-filled syringe. Autoinjectors and on-body injectors may be used to automate the injection and delivery or administration process, thereby simplifying the process for certain patient groups or subgroups for which use of the syringe/vial combination or pre-filled syringe systems is disadvantageous, whether because of physiological or psychological impediments.

Even with the use of drug delivery devices, such as autoinjectors, patients may experience challenges during the initial use of the drug delivery device after they have been prescribed a drug that is delivered or administered through the use of a drug delivery device. For example, the user may be uncertain whether the injection should be delayed after a drug delivery device has been removed from cold storage, such as in a refrigerator, and if the injection should be delayed, how long it should be delayed. Additionally, the user may be uncertain whether the medication inside the drug delivery device is the medication prescribed for them. Further, the user may be uncertain whether the medication has expired. Still further, the user may also be uncertain if the actions and their sequence necessary to correctly operate the drug delivery device.

In addition, after a substantial period of storage, various features of the drug delivery device may require initiation and/or acceleration to ensure proper delivery of the medication. For example, after the drug delivery device has been removed from cold storage, the temperature of the medicament inside the drug delivery device may need to be raised prior to injection. While passive warming of the medication is possible, it may be desirable to hasten this process so that the user to not have to wait a significant period of time to deliver the drug. Also, onboard electronics of the drug delivery device may need to be awakened from a low-energy state to a high-energy state prior to drug delivery.

As set forth in more detail below, the present disclosure sets forth an drug delivery system embodying advantageous alternatives to existing drug delivery devices and that may address one or more of the challenges or needs mentioned above.

SUMMARY

According to an aspect of the disclosure, a drug delivery system includes a drug delivery device comprising a reservoir, a delivery cannula having a proximal end in fluid communication with the reservoir and a distal end to be received within a patient, and a controllable element. The drug delivery system also includes a sensor coupled to the drug delivery device and a controller coupled to the sensor as well as the controllable element. The controller may be configured to: use the sensor to determine a condition or an operational state of the drug delivery device, and control the controllable element based on the condition or operational state of the drug delivery device.

According to another aspect of the disclosure, a drug delivery system includes a drug delivery device comprising a reservoir, a delivery cannula having a proximal end in fluid communication with the reservoir and a distal end to be received within a patient, and a controllable element. The drug delivery system also includes a memory configured to store identity information representative of at least one of an identity of the patient, an identity of the drug delivery device, or an identity of a medicament to be stored within the reservoir. Additionally, the drug delivery system includes a controller coupled to the memory and the controllable element. The controller may be configured to control the controllable element based on the identity information.

According to a further aspect of the disclosure, a method is provided of using a drug delivery device comprising a reservoir, a delivery cannula having a proximal end in fluid communication with the reservoir and a distal end to be received within a patient, a removable sterile barrier disposed about the second end of the delivery cannula, and a controllable element. The method includes determining, with one or more sensors, a condition or an operational state of the drug delivery device, and controlling the controllable element based on the condition or the operational state of the drug delivery device.

BRIEF DESCRIPTION OF THE DRAWINGS

It is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

FIG. 22 is cross-sectional view of an embodiment of a removable sterile barrier attached to a housing of a drug delivery device; and FIG. 23 is a cross-sectional view of the removable sterile barrier of FIG. 22 after its removal from the housing of the drug delivery device.

DETAILED DESCRIPTION

Figure 1:
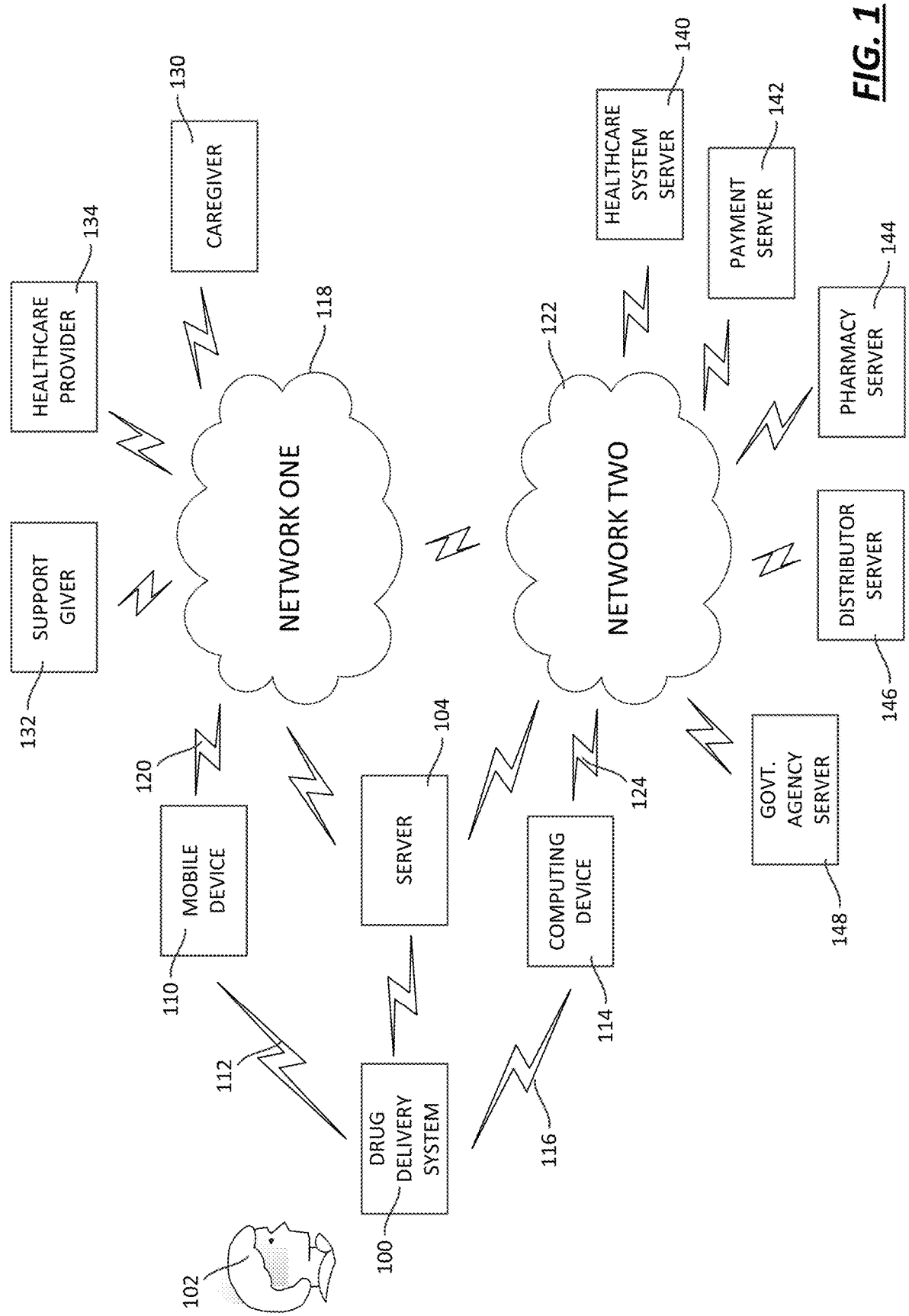
FIG. 1 is a schematic diagram of a drug delivery system according an embodiment of the disclosure in communication with one or more computing devices and one or more networks.

This disclosure is directed to a plurality of systems including a drug delivery device, and to a plurality of methods for using the drug delivery system. In particular, the systems and methods involve the determination of one or more states, which states may be determined through the use of one or more sensors in combination with one or more controllers. The sensors may rely on mechanical, electrical or chemical sensing mechanisms, and the controllers may be mechanical, electrical or electro-mechanical. By way of example and not by way of limitation, the states may relate to the operation of the drug delivery device, or to the condition of the drug delivery device. The system and methods may use the state determination to control the operation of the drug delivery device, and/or may communicate the state determination to other devices, such as third-party servers that may collect, process and/or further disseminate the state determinations received from the system including the drug delivery device, the one or more sensors, and the one or more controllers. In addition or in the alternative, the systems and methods may communicate the state determination to local devices, such as a mobile computing device (e.g., cell phone).

A drug delivery system according to the disclosure may include a drug delivery device having a reservoir (which may also be referred to as a primary container, e.g. a syringe, vial or cartridge). The reservoir may contain a drug, which may also be referred to as a medication or a medicament. The drug may be, but is not limited to various biologicals such as peptides, peptibodies, or antibodies. The drug may be in a fluid or liquid form, although the disclosure is not limited to a particular state (e.g., no differentiation is intended between a solution, a gel, or a lyophilized product for example). The drug delivery device also includes delivery cannula having a first end connected to or connectable in fluid communication with the reservoir and a second end to be inserted within a patient. As used herein, the term "delivery cannula" or "cannula" is hereby defined to mean a tube that can be inserted into the body for the delivery of fluid. A cannula may include a rigid or semi-rigid needle or blunt cannula, or may be in a flexible form, by example and not by way of limitation. The cannula may be integrated with the other elements of the drug delivery device, or the cannula may be separate from the other elements of the drug delivery until immediately prior to use. According to certain embodiments, the drug delivery device may further include an inserter to introduce the second end into the patient, although this is not required according to each embodiment of the disclosure. The inserter may or may not be withdrawn back into the device, thereby leaving the cannula in a patient.

Considering the foregoing description of the drug delivery device, the device may be characterized as an autoinjector or an on-body injector or infuser (the reference to injector intended to include also a reference to an infuser, to the extent that a difference is suggested). Autoinjectors may be single-use devices, administering a single dose during a single application of the device to the user's skin, although autoinjectors are not limited to only single-use devices—they may be multi-use devices as well. On-body injectors may be multi-use devices, administering multiple doses during one or more applications of the device to the user's skin, although on-body devices may also be used as single-use devices. Either autoinjectors or on-body injectors may have assemblies or sub-assemblies that are reusable, in that the assemblies may be used and re-used by refilling the reservoir, by removing an empty reservoir and replacing it with a filled reservoir, or by replacing the cannula, for example.

As noted above, the system or method according to the disclosure will determine one or more states relative to the drug delivery device.

For example, the system or method may determine if the drug delivery device is in one or more operational states (i.e., a state relating to the operation of the drug delivery device to deliver the drug to the patient). A non-exhaustive list of the general operational states may include (i) packaged/ready for distribution; (ii) packaged/distributed; (iii)

unpackaged/ready for administration; (iv) sterile barrier removed; (v) device applied; (vi) cannula injected (or inserted); (vii) drug delivery initiated; (viii) drug delivery completed; and (ix) device removed. The system or method may determine specific operational states within each of the general operational states; for example, the system or method may determine if plunger has been moved from a first end of a bore (defining a drug reservoir) to a second end of the bore to determine if the drug delivery device is in the "drug delivery complete" state.

Furthermore, the system or method may determine if the drug delivery device is in one or more condition states (i.e., a state relating to the condition of the drug delivery device, not necessarily related to the operation of the drug delivery device to deliver the drug to the patient). A non-exhaustive list of condition states may include (i) age (e.g., taken with respect to a manufacturing date or an expiration date); (ii) sterility/contamination; (iii) temperature (or temperature history); and (iv) orientation. The determination of a condition state may be considered as part of the determination of an operational state; for example, the determination of the temperature state may be considered as part of the determination of the "ready for administration" state. Alternatively, the operational and condition states may be determined separately.

These states may be determined through the use of one or more sensors. The sensors may be particular to a condition state to be determined: for example, a thermocouple disposed adjacent to the reservoir may be used to determine the temperature state of the drug delivery device. The sensors may be particular to an operational state to be determined: for example, a switch may be coupled to a needle guard to determine when a needle cap has been removed to determine the "sterile barrier removed" operational state, the switch being open when the needle cap is disposed over the second end of the cannula and the switch being closed when the needle guard is not disposed over the second end of the cannula. Sensors may be used to determine both a condition state and an operational state: for example, the thermocouple may be used to determine the temperature condition state of the device (or more particularly, the drug), and/or the thermocouple may be used to determine the "ready for administration" operational state.

The system or method may use the determined states to control the operation of the drug delivery device. For example, the system may include a controller that is coupled to the sensor and may be coupled to one or more of the assemblies or subassemblies of the drug delivery device described above, or to one or more additional assemblies or subassemblies of the drug delivery device. The controller may be adapted structurally or programmed (if electrical or electro-mechanical) to activate or to inhibit these assemblies or subassemblies in accordance with the determined states. For example, the drug delivery device may include a lockout that limits or completely inhibits the operation of the injector, and the controller may activate the lockout in a reversible fashion if the temperature state of the drug delivery device (and in particular, the drug in the reservoir) is below a threshold state.

The system or method may communicate the determined state(s) to another device or system, which communication may be performed in conjunction with use of the determined state(s) to control the operation of the drug delivery device. For example the system or method may communicate the determined state(s) with a networked device using a communication link. In this sense, a networked device is intended to include any device that communicates with at least one other device over a communication link, and might include communication with a device such as mobile device (e.g., cell phone or mobile computing device) using a Bluetooth connection or a computing device using a Wi-Fi connection, for example. The networked device may communicate the determined states to other computing devices remote from the drug delivery system over the network that includes the networked device such as a server. According to certain embodiments of the present disclosure, the system communicates directly with the network (i.e., without an intermediate networked device—the system would be a networked device) or directly with a remote computing device such as a server (using, for example, a 3G antenna). The state information communicated over network, may then be used, for example, to determine if a patient is in compliance, or if a class of drug delivery devices is exhibiting a systemic malfunction. The state information may be used in other manners as well.

The systems and methods may also include control of the drug delivery device according to information relating to the identity of the drug, the drug delivery device, or the user, and/or communication of this identity information. Identity information relating to the drug may include a drug name, a drug concentration, dose information, a lot number or serial number, and a date of manufacture and/or expiration. Identity information relating to the drug delivery device may include a device type (e.g., autoinjector, on-body injector), a lot number or serial number, and a date of manufacture. Identity information relating to the user may include a patient name, demographic information, and patient subgroup information. This information may be referred to as "static" information, in contrast to the state information discussed above.

As to the communication of the information, and in particular relative to the identity information discussed immediately above, it will be recognized that not all information may be useful, desired, or even accessible to every different party whether for convenience, patient privacy or data security concerns.

FIG. 1 illustrates a drug delivery system 100 according to an embodiment of the disclosure. The drug delivery system 100 may be associated with a patient 102, who may use the drug delivery system 100 to inject a drug as part of a therapeutic regime. The drug delivery system 100 may communicate with a computing device (e.g. server) 104 via one or more intermediate computing devices and/or one or more networks. In turn, the server 104 may communicate with the drug delivery system 100, the patient 102, and one or more computing devices (with their associated parties) via one or more intermediate computing devices and/or one or more networks. As is also illustrated in FIG. 1, the server 104 may communicate directly with the drug delivery system 100, using a 3G antenna for example.

For example, the drug delivery system 100 is illustrated as communicating with a mobile computing device 110 (e.g., a smartphone) via a first communication link 112, and with a computing device (e.g., a personal computer or dedicated hub) 114 via a second communication link 116. Both links 112, 116 may operate according to a near field communication protocol, such as Bluetooth, for example. The mobile computing device 110 may communicate with a cellular network 118 via a communication link 120, while the other computing device 114 may communicate with a hard-wired network (e.g., local area network or wide area network) 122 via a communication link 124. These networks 118, 122 may also communicate with the server 104.

The networks 118, 122 may facilitate communication between the server 104 and one or more parties associated with the patient 102, such as his or her caregiver 130, support giver 132, and healthcare provider 134, via their mobile computing devices (e.g., smartphones). The server 104 may also be in communication with one or more computing devices (e.g., servers) associated with one or more additional parties associated with the patient 102. For example, a healthcare system server 140, a payment server 142, a pharmacy server 144, a distributor server 146, and a governmental agency server 148 are illustrated in communication with the server 104 via the network 122. It will also be recognized that the networks 118, 122 may be in communication with each other.

Figure 2:
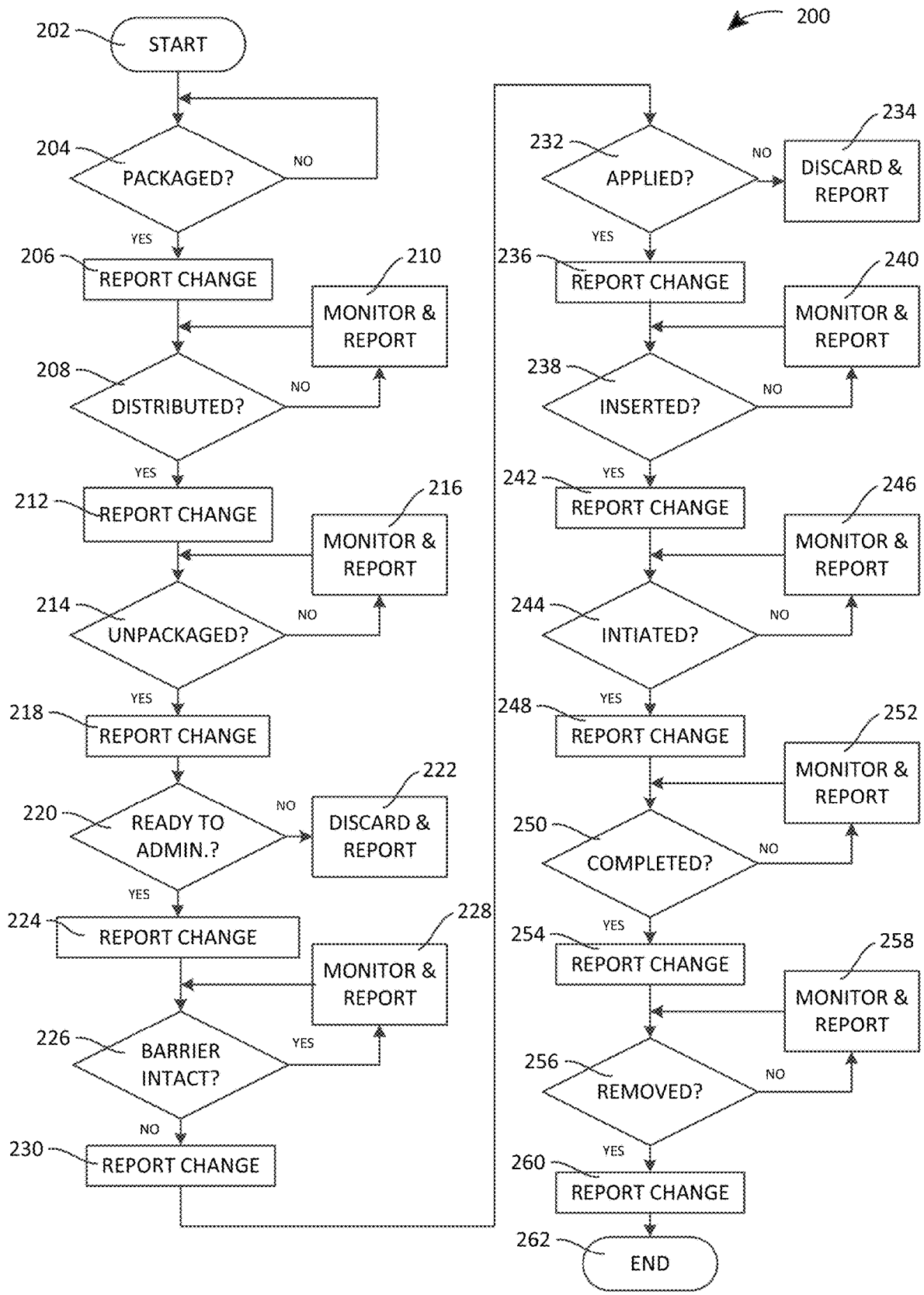
FIG. 2 is a block diagram of a method of operating the drug delivery system illustrated in FIG. 1 according to an embodiment of the disclosure.

FIG. 2 illustrates a method 200 of operating a drug delivery system, such as the drug delivery system 100 in FIG. 1, to determine various condition and operational states of the drug delivery system, to control the drug delivery system according to those states, and to communicate the determined state information to a computing device, such as the mobile device 110 and/or the server 104. From a brief review of the flowchart of FIG. 1, it will be recognized that the method 200 according to FIG. 2 illustrates the determination of various condition and operational states of the drug delivery device that is part of the drug delivery system, and the actions taken and communications made in association with or in regard to these condition and operational states. It should also be recognized that while the method 200 includes the actions described herein, other embodiments of a method of operating a drug delivery system according to the disclosure may include only some of the actions described herein, as is specifically illustrated in FIG. 3, for example. Those actions outlined in FIG. 2 not included in other embodiments of a method of operating a drug delivery device according to the disclosure may be omitted or eliminated.

The actions and communications from the drug delivery system may change with the drug delivery device operational state as that device passes through the useable product life cycle from manufacture to disposal, as indicated in FIG. 2. In fact, the determination made on the basis of a single sensor may vary according to the drug delivery device's operational state. By way of example, in regard to those drug delivery devices that utilize a needle cap disposed over a second end of the cannula to preserve sterility, determination made using a needle cap sensor that the needle cap has been removed from over or about the second end of the cannula prior to package or packaging removal might indicate that primary container integrity has been compromised, whereas in removal or separation of the needle cap from over or about the second end of the cannula after package or packing removal might indicate that the device is ready to administer the drug.

The method 200 starts at block 202, and continues from block 204 to blocks 206 and 208 when it is determined that the drug delivery system has been packaged. In particular, once it is determined that the device is packaged at block 204, a communication is made at block 206 to report the operational state change of the device, and the method continues to block 208, where a determination is made whether the device has been distributed.

Between the determination that the drug delivery system has been packaged and the determination that the drug delivery system has been distributed to the user, the drug delivery device may pass through different portions of the supply chain. The portions of the supply chain through which the drug delivery system may pass may depend on the drug in the drug delivery device, the intended use of the drug delivery device by the user, which may be a patient or a healthcare professional, or other factors (such as the structure and characteristics of the drug delivery device itself).

As the packaged device emerges from manufacture, there is interest in maintaining current knowledge of the authenticity, environmental history and information about the current or historic location throughout distribution. Consequently, while the method and system await the determination of the transition to the next operational state at block 208, the system may monitor and communicate this information at block 210. By automating the collection and reporting of information in this state, supply chain partners can leverage improved information and supply chain management systems. Information such as product identification, expiration date, and counterfeiting measures might be useful for logistics, warehousing, and customs officials. This information, when added to what is known of the combination product (i.e., therapeutic and diagnostic products that combine drugs, devices, and/or biological products) during manufacture can help alert interested and authorized parties to product location in the event of field events such as product transfer or return and replacement under recall.

Depending on the route which the drug delivery system takes between the manufacturer and its distribution to the patient or healthcare provider, the drug delivery system may also pass through a pharmacy, where the system may also monitor and communicate information at block 210. If the drug delivery system passes through a pharmacy, information such as drug/dose/device, environmental history, expiration date, counterfeiting measures, and location data may provide useful information to those responsible for managing stock and ensuring product quality as delivered to the end user. Incorporation of signals which trigger access to label and instruction information can provide value in training the end user about the delivery device or drug product, provide access to user communities and provide an information stream to the user or user's network about the effectiveness of product training or associated materials. These signals, when added to what is known of the combination product during manufacture can help to alert to product location in the event of field events such as product transfer or return and replacement under recall.

Once the determination is made at block 208 that the packaged product has been distributed to the user (e.g., a patient or healthcare provider), the method 200 may continue to block 212 where the change in the operational state is communicated. The method 200 may continue with a determination as to whether the drug delivery device has been unpackaged at block 214. If the determination has not been made that the drug delivery device has been unpackaged, then the method 200 may monitor the drug delivery system, and report information at block 216. If the determination has been made that the drug delivery device has been unpackaged, then the method continues to block 218 with the communication of the operation state change.

During this operational state, information such as environmental history, instructions for use, storage instructions, product authenticity or any associated field alerts for the produced lot of materials, expiration date, medication reminders and current location or estimated arrival through shipping provide information of interest to the user. The use of sensors to provide signals for environmental condition such as temperature can help the user to understand whether the product is now suitable for use, i.e., whether the method may pass from block 214 to block 220 (with the reporting occurring at block 218). One extended example of this is a "wake-up" of the electronics into a high-activity state or a high-energy power state for delivery and reporting when temperature exceeding a certain threshold such as 15 C. This could result in a message to the user (e.g., via the user's networked devices) to return to the device to cold storage or administer within 24 hours. Similarly, the sensed temperature could put the electronics back into a low-activity state or low-energy state (e.g., a "sleep" state) if the drug product drops below a preset threshold such as 15 C.

If the determination is made at block 214 that the device has been unpackaged (presumably by the user), then the method 200 may report the operational state change at block 218, and proceed to the determination at block 220. As noted above, it is possible for the method to carry out determinations other than those illustrated at block 214 before the method 200 may proceed to block 220.

In determining if the system is ready for use at block 220, it is typical to verify the quality of the product presented. While the user may perform this action, the system may also include sensors that will carry out this action. For example, the verifications may include verification of the label information to confirm authenticity, visual inspection the device for signs of damage or to confirm that the needle cap has not come free in shipping, visual inspection of the drug product container for color and clarity. The verifications may also include a determination whether the environmental history of the device is such that the device may be safely used. Such a determination may consider the environmental conditions through storage and distribution which may have compromised the drug product or the delivery device. By including sensors in the device (such as position or proximity sensors for the needle cap or temperature sensors), many of these inspection steps can be automated, providing greater ease of use to the user and greater information to the user and user's network.

According to the determination made at block 220, the method 200 may pass to block 222, where the user discards the device instead of using the device. For example, it may be determined at block 220 that the environmental history of the device is such that the device may not be safely used. In such a case, the device may indicate to the user that the device is to be discarded at block 222 and may communicate this information to a remote server that tracks such device determinations, or may communicate this with a local device (such as a mobile or cell phone or other mobile device, portable computing device or the like) that is capable of being or is networked and may communicate the information to a remote server.

On the other hand, if the determination is made at block 220 that the system is ready for administration, the method 200 may proceed to block 224 with the reporting of the change in operational state. The method 200 may then continue to block 226, wherein a determination is made whether a barrier is no longer intact, has prematurely deployed or if it has been prematurely removed or separated from the drug delivery device such that the sterility of the device is no longer preserved or can no longer be assured to be preserved. In this regard, the barrier may be a sterile barrier (i.e., the minimum package that prevents ingress of microorganisms and allows aseptic presentation of the product at the point of use), such as a needle cap. If the determination is made at block 226 that the barrier is intact, then the method 220 may continue at block 228, wherein the operational state and condition states of the system are monitored and that information is communicated to local or remote devices. If the determination is made that the barrier is no longer intact, then the method 200 may continue to block 230, wherein the operational change is reported, and the method 200 may continue to block 232.

In regard to the determination made at block 226, it is typical for autoinjectors and on-body devices to have a component or packaging product that is removed immediately before administration that maintains the sterility of the needle or injection head. Sometimes outside protective packaging is inappropriately removed and discarded days in advance of medicament administration; while normally the patient may be no more than a few minutes away from insertion and/or injection when the sterile barrier is removed from the device. This determination also provides a key opportunity to ensure the drug delivery device electronics are "awake" (e.g., in a high-energy state) during the injection process without requiring excess cost and bulk to ensure adequate power through manufacture, storage, and distribution before key functions are performed.

By triggering onboard electronics (e.g., a circuit) to "wake-up" from a low-energy state to a high-energy state upon removal of the sterile barrier, the onboard electronics of a drug delivery device can provide significantly improved power consumption while in manufacture, storage and distribution. According to certain embodiments, the startup sequence may take 10-200 seconds for example, inclusive of startup, completion of preliminary checks and interaction with the patient/user in advance of attempted administration (which interaction may include waiting for the device/drug to warm to room temperature, although inclusion of this action may further increase the total time required). Conversely, one can wait for body contact or delivery actuation to wake-up the onboard electronics from a low-energy state to a high-energy state, but this may not provide an opportunity for every desired "Smart" feature. Similarly, if something such as the removal of protective packaging from an exterior of the drug delivery device is used to wake-up the electronics from a low-energy state to a high-energy state, then there is a risk that a significant amount of power will be utilized in advance of delivery that can complicate the optimization of the device and drug delivery system.

It is possible to design a component that is removed in conjunction with the sterile barrier, which has typically provided an opportunity to increase the ease, ergonomics, or obviousness of removal. By designing a tab, or other electrically insulating feature into this component; it may be inserted into the power circuit of onboard electronics so that removal of the sterile barrier connects the battery or other power supply and wakes up the electronics from a low-energy state to a high-energy state to perform the required functions. Alternatively, the removal of the barrier may cause a switch to close, completing a circuit with the power supply, and thus powering up the system into from a low-energy state to a high-energy state.

At block 232, a determination is made if the drug delivery system has been applied to the patient. In regard to an autoinjector, this determination may involve a determination as to whether the autoinjector has been held in place against the patient's skin. In regard to an on-body injector, this determination may involve a determination as to whether an adhesive has been exposed on a surface of the on-body injector and the injector has been disposed onto the surface of the patient's skin. According to certain embodiments of the method 200, if a determination is made at block 232 that the drug delivery system has not been applied within a specified time after the barrier is no longer intact, the user may be instructed to discard the device at block 234 and the event is communicated to local and/or remote devices. Alternatively, if the determination is made that the device has been applied to the patient at block 232, the operational state change is reported at block 236 and the method 200 proceeds to block 238.

In some embodiments, the determination made at block 232 regarding skin application may be performed repetitively at pre-defined intervals (e.g., every 5 milliseconds) throughout the remainder of the method 200. Accordingly, it may be possible to determine if the drug delivery device has been prematurely removed from the patient's skin prior to completion of delivery of the medicament to the patient, and if so, when this occurred relative to the start of medicament delivery. This information may be used to calculate an amount of the medicament actually delivered to the patient prior to the premature removal of the drug delivery device from the patient's skin.

As was the case above, it may also be useful to know when deliberate contact has been made between a housing of the drug delivery device and a patient's skin, because this may be a useful opportunity to "wake-up" onboard electronics from a low-energy state to a high-energy state for example depending on what "smart" functions are desired by the circuitry. Alternatively, some checks to confirm that the device is ready for administration might be performed in order to provide the user with greater confidence in the value of the injection.

Additionally, there is a risk of deliberate non-compliance with therapy where many commercially available injectors can be tricked into dispensing medication by depressing the needle guard and activating the product to dispense into the air instead of the patient. There is incremental value in the knowledge that the device was in contact with the body throughout the delivery period, and particularly if additional information that is in line with the properties expected of human tissue and appropriate injection sites. The overlap of known body contact with the duration of drug delivery and completion can be used to infer the amount of dosage missed in the event of use errors as further explained in the similar state of "needle inserted".

The method 200 determines at block 238 if the second end of the cannula has been injected or inserted into the patient. With many drug delivery devices, the injection of the cannula into the patient is not instantaneous with the application of the drug delivery device to the patient's skin. For example, there may be a delay between application and injection because of time required for various assemblies or subassemblies of the drug delivery device to recognize that the drug delivery device has been applied and to activate the injector. Alternatively, there may be a planned delay in the injection of the cannula because the administration of the drug is planned to occur after a time delay elapses after application of the drug delivery device to prevent damage to the cannula or discomfort to the patient because of the planned delay between application and injection. In yet another alternative, in an on-body drug delivery device, a needle referred to as an introducer needle may be activated to insert a cannula that can remain inserted in the patient. The needle then retracts back into the delivery device, leaving the cannula behind. The actual injection or introduction of a medicament can occur immediately thereafter or at a later desired time. As such, the method 200 may proceed to block 240 if it is determined at block 238 that the cannula has not been inserted, and the system may monitor the operational state and one or more condition states and communicate that information.

Similar to the body contact information, the injection information may be used in conjunction with other processes to achieve a higher confidence in the gathered information. In contrast to body contact information, accurately measuring needle insertion to the target administration route such as intradermal, subcutaneous, intramuscular, intravenous, ocular or others can provide direct confirmation that the drug product was delivered to the correct anatomical depth and location.

One use for needle insertion signal can be release of a delivery lockout once the needle has been inserted into the patient. Alternatively, if the completion of drug delivery occurs and the needle was inserted for the entire period of time between "delivery triggered" and "delivery completion" a very high degree of confidence in successful dosing is provided. And conversely if the timing of the events do not overlap appropriately it may be possible to predict the amount of dose that was successfully delivered based on the systems delivery characteristics. In the event that an incomplete or unsuccessful dose administration is detected and reported, there is significant incremental value if the amount of dose discrepancy is also reported. A "Smart Drug Delivery Device" might be used for many different types of medicaments with varying therapeutic effects and toxicity risk profiles. For example some medications may require urgent completion of dosing such as by a second injection for any incomplete dose if there is a low risk of toxicity but high risk of complications with a missed or incomplete dose. Alternatively, a healthcare provider may prefer to know about a missed or incomplete dose but wait for the next dose instead of scheduling a replacement if the risk of complications is low. Importantly, there may be opportunities to mitigate issues associated with incomplete dosing by administering just the amount of missed dose if it is correctly recorded and reported, offering an opportunity to maximize benefit while minimizing the overall cost of care.

If the determination is made at block 238 that the needle has been inserted, then the method 200 may communicate the operation state change at block 242 and determine if the administration of the drug has been initiated or triggered at block 244. If the cannula has been inserted, but the administration has not yet started, the method 200 may continue at block 246 to monitor the states of the drug delivery device, and communicate that information. A delay between the insertion of the cannula and the administration of the drug product may occur because of the sequential operation of the assemblies or subassemblies of the drug delivery device, or the delay may be planned, such that the cannula is inserted into the patient contemporaneous with or approximately contemporaneous with the application of the device to the patient's skin but administration occurs at least a time delay thereafter.

It is believed that successful triggering of delivery generally leads to successful dosing except when a device may be programmed to insert a cannula and then at a later time the injection of the medicament begins. Upon triggering, the patient has generally performed an action intended to provide the therapeutic result. Triggering delivery may be viewed, according to certain embodiments, as evidence of a higher level of commitment as compared to body contact or needle insertion alone. It is believed that some patients try different sites by placing the device against the body to "feel" it before triggering delivery. Many devices include a feature to ensure that delivery is not triggered for such trials. Thus it is known that triggering delivery typically indicates the patient has mentally committed to dose the prescribed therapy. Enabling features of a "Smart Drug Delivery Device" to sense when delivery has been triggered provides value to many stakeholders as an indication of compliance. While not as direct a measure of successful delivery by comparison to other methods, detecting a trigger signal can be achieved through relatively simple means, providing greater value of cost and reliability.

Once the determination has been made that administration of the drug product has been initiated at block 244, the method may proceed to block 248 where the operational state change of the device is communicated with local and/or remote devices. The method 200 then proceeds to block 250, and a determination is made that the administration of the drug product is complete. Until the determination is made that the administration of the drug product is complete, the system continues to monitor the device, and communicate the information at block 252. Once the determination is made that administration is complete at block 250, the change in operational state is communicated at block 254, and the method 200 proceeds to block 256.

Capturing the completion of administration or delivery is a useful metric, particularly in combination with other device state information. By itself there is value if a device does not have the means to capture other device states, and indeed would provide sufficient value to many stakeholders if the other states were unable to be reported. However, capturing the time and date of dose delivery completion in comparison to other device states can provide a very high level of confidence (or counterevidence) that the drug was delivered successfully. For example, if dose completion occurred while the needle was still inserted that confirms that the patient or caregiver administering the medicament did not pull the device away from the body during or after it was triggered thus compromising the dosage accuracy. Commonly available drug delivery devices may lockout to prevent drug delivery in advance of applying the device to the body, but once the device has been applied to the body there is generally no means of keeping the device secured against the body during the full time of delivery. Most often the drug will continue to deliver, spilling into the air as waste if the needle is pulled away from the body after the delivery is triggered. Sometimes a medicament may be painful or cause a certain sensation due to the specific ingredients or speed of delivery and thus cause a reflex that compromises the dose even after the needle has been inserted. Other times, an action of the delivery device itself may startle the user and cause the same reflex. It is known to be important for the user or user's network to understand the difference between slow response and noncompliance to a therapy in order to provide the patient with the evidence needed to encourage compliance with a given therapy or the evidence needed to alter a therapeutic strategy. Thus there is incredible value to the patient to a comprehensive measurement and reporting of drug delivery device performance.

Several of the embodiments disclosed below may be expanded in scope to monitor the overall progress of the delivery. For example if an optical sensor is optimized to detect the stopper material and oriented at the end of the delivery stroke that can be used to relay completion information; similarly an array of optical sensors placed parallel to the travel of a plunger through a drug reservoir might be used to monitor progress throughout the travel.

At block 256, the method 200 determines if the device has been removed from the patient. The determination at block 256 may be based on a skin sensor that determines if the device is no longer in contact with the patient's skin. According to other embodiments, the determination may be made on a needle shield or other structure that deploys after removal from the skin to prevent contact with the second end of the cannula of the drug delivery device. According to still other embodiments, the removal of the drug delivery device may be based on a change in the orientation of the drug delivery device. In any event, until it is determined that the drug delivery device has been removed, the method and system may monitor the device at block 258 and communicate information with local and/or remote devices. When it is determined that the drug delivery device has been removed, the method communicates this operational state change at block 260, and ends at block 262.

Disposal of the device, and alternatively receipt of a used device by collection center, provides a final opportunity to interrogate any stored information and/or utilize the receipt itself to function as evidence of prior state changes. Any data collected previously might be stored for download at a collection point. In addition, for situations where a return is warranted for replacement or in satisfaction of other field action, knowledge of the location of the drug delivery device through distribution and return shipping is valuable. The same signals, in combination with remote authorization of return can allow for return shipping to be electronically authorized and paid for by the appropriate partner in the user or distribution network with minimal impact to the user.

It will be recognized that according to other embodiments of the disclosure, the various operational states described in regard to FIG. 2 may be considered to be optional. For example, it may not be necessary to make the determinations at blocks 238 and 244 relative to the insertion of the cannula and the initiation of the administration of the drug product if, for example, the determinations are made at blocks 232 and 250 that the device has been applied and the drug product administration has been completed. Furthermore, while the method 200 includes communication of operational state changes after each operational state change, none of the operational state changes may be stored within the system, but the communication of each of the operational state changes may not occur until block 260. Further, while the monitoring of the drug delivery device has been illustrated as occurring while the method 200 is waiting for certain determinations to be made (e.g., block 208 and 210), this monitoring need not be performed at every instance illustrated.

Furthermore, it will be recognized that the monitoring described in FIG. 2 may include more than monitoring of the various operational state changes discussed. The monitoring may also include monitoring of condition state changes. In fact, the method and system may monitor one or more sensors to make these operational and/or condition state changes, which information or signals from the one or more sensors may be used in the determinations made at various points along the method 200.

Figure 3A:
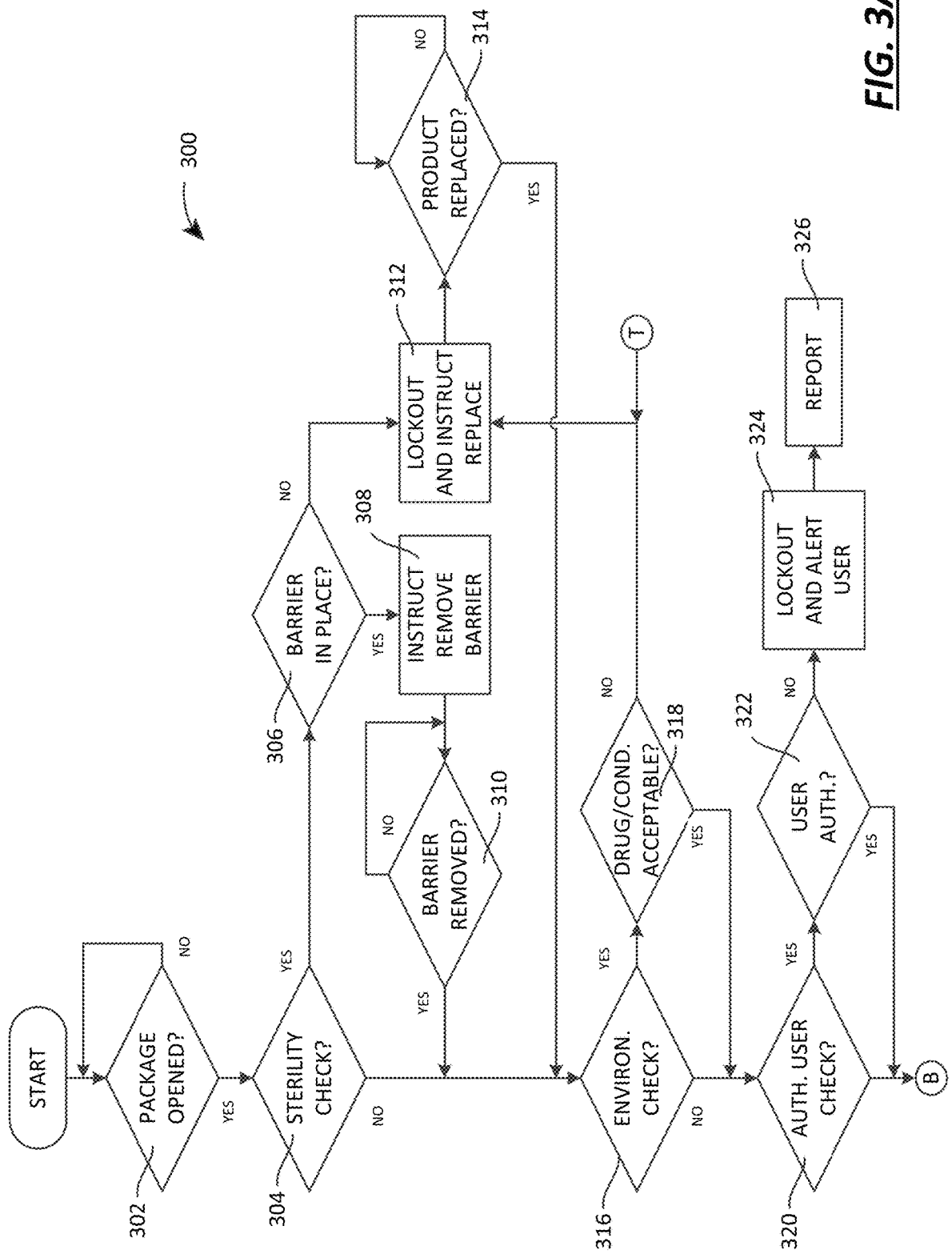
FIGS. 3A-3C is a block diagram of a method of operating the drug delivery system illustrated in FIG. 1 according to another embodiment of the disclosure.
Figure 3B:
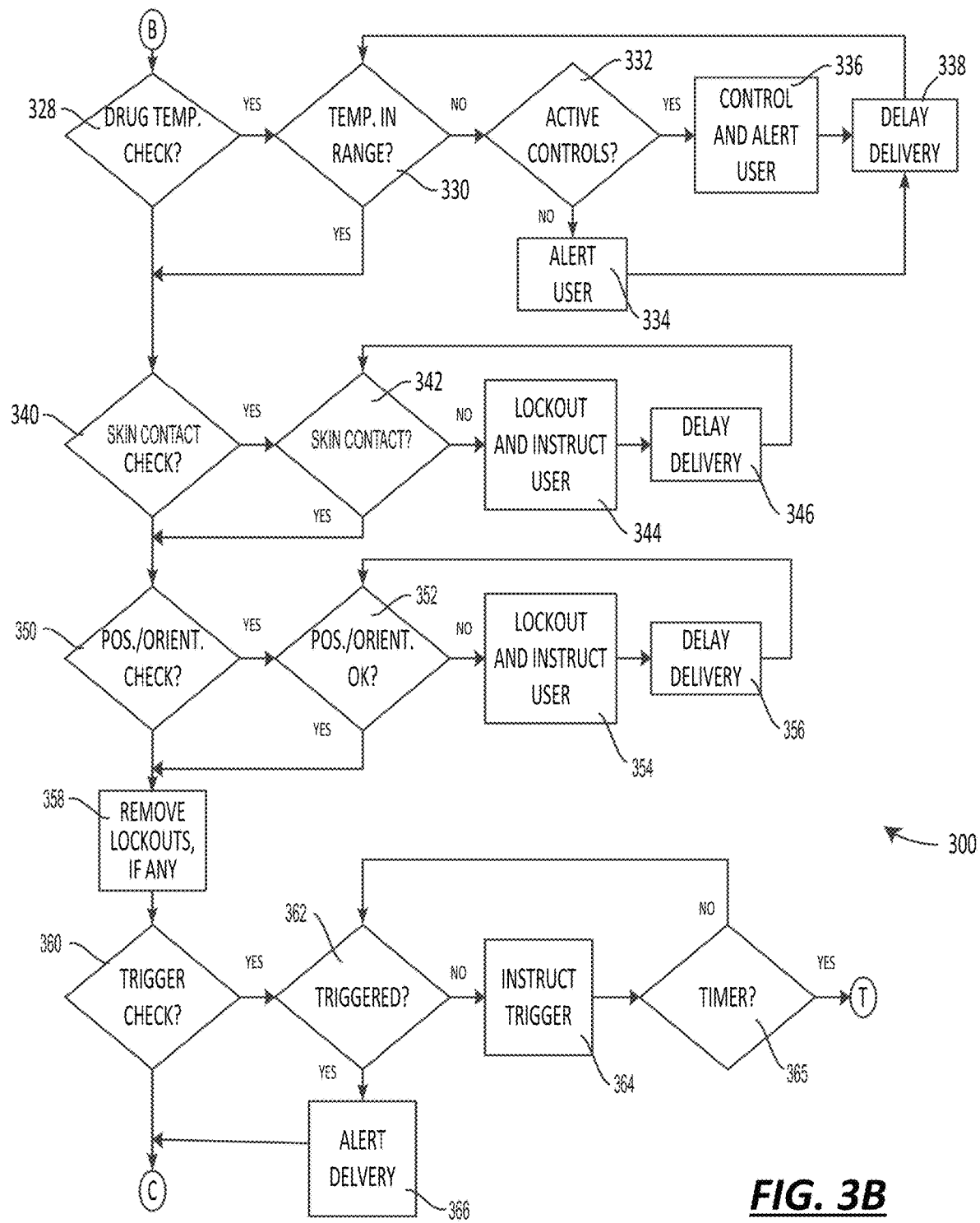
Figure 3C:
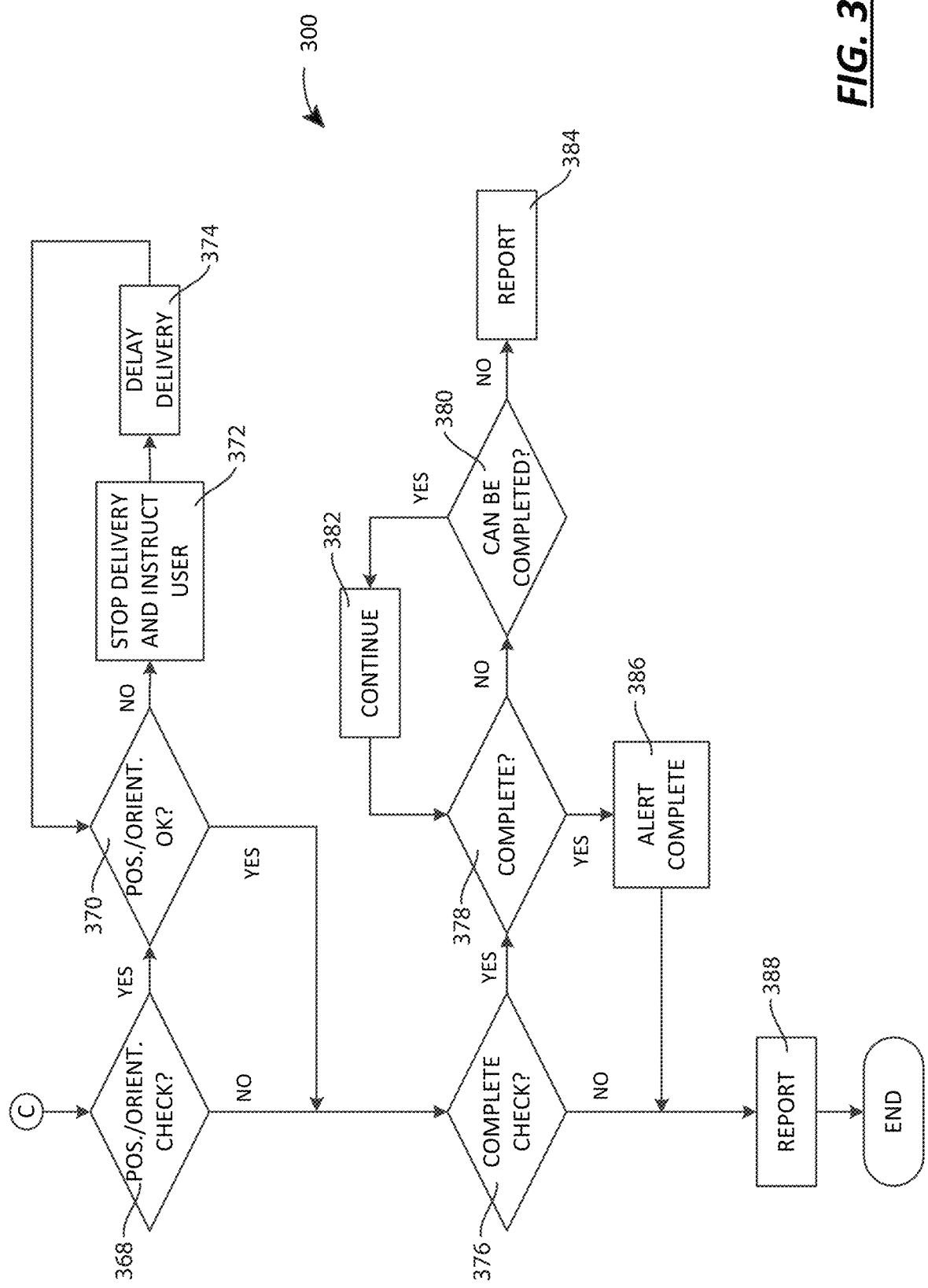

FIGS. 3A-3C illustrate a method 300 of operating a drug delivery system, such as the drug delivery system 100 in FIG. 1, to determine various conditions and/or operational states of the drug delivery system, to control the drug delivery system according to those determined states and/or identity information, and/or to communicate the determined condition and/or operational state information to a computing device, such as the mobile device 110 and/or the server 104. From a brief review of the flowchart of FIG. 1, it will be recognized that the method 300 according to FIGS. 3A-3C illustrates the determination of various conditions and/or operational states of the drug delivery device that is part of the drug delivery system, and the actions taken and communications made in association with or in regard to these conditions and/or operational states and/or identity information. It should also be recognized that while the method 300 includes the actions described herein, other embodiments of a method of operating a drug delivery system according to the disclosure may include only some of the actions described herein.

Referring first to FIG. 3A, the method 300 may begin with the drug delivery device in the package, and the method waits at block 302 until it is determined that the package has been opened. At this point, the device may optionally be locked until such time as the system conducts one or more validations, verifications or checks to ensure that the device is ready to administer, the sterile barrier has been removed and/or the device has been (correctly) applied (see blocks 220, 226, 232 of method 220 in FIG. 2). Before conducting each of the one or more validations, verifications or checks, the method 300 may determine if the drug delivery device is adapted or programmed to carry out the validation, verification or check. For example, a determination may be made at block 304 if the drug delivery device is adapted or programmed to check the sterility of the drug delivery device; in particular, the validation or verification may be related to a sterile barrier disposed at the second end of the cannula. If the drug delivery device is adapted or programmed to perform the sterility check, the method 300 may proceed to block 306, where it is determined if the sterile barrier is disposed over or about the second end of the cannula, for example.

If it is determined at block 306 that the barrier is in place, then the method may proceed to block 308 where the user is instructed to remove the barrier. The method 300 may then determine at block 310 if the barrier has been removed. When it is determined that the barrier has been removed, a sterility timer may be started, the expiration of which may result in the drug delivery device being placed into or remaining in a locked state, preventing use of the drug delivery device.

If it is determined at block 306 that the barrier is not in place (i.e., the barrier has been prematurely removed), the method 300 may proceed to block 312, wherein the delivery device is locked (e.g., a lock or lock-out device is actuated) or the delivery device remains in a locked state if the device was previously locked. According to certain embodiments, the locking of the delivery device at block 312 may be irreversible. According to other embodiments, including the embodiment illustrated in FIGS. 3A-3C, the lock may be reversed once it is determined that the drug product (e.g., the drug product reservoir) or medicament has been replaced at block 314. If the drug product or medicament is not replaced, or in those embodiments where the drug product or medicament cannot be replaced (i.e., the lock is irreversible), information regarding the failed sterility check may be communicated by the system.

If (i) the determination is made at block 304 that the system is adapted to validate, verify or check the sterility of the device, (ii) the determination is made at block 306 that the barrier is in place and at block 310 that the barrier subsequently has been removed, or (iii) the determination is made at block 306 that the barrier is not in place but the determination is made at block 314 that the drug product or medicament had been replaced, the method 300 continues to block 316. At block 316, a determination is made if the drug delivery device is capable of performing visual and/or environmental inspections. If the device is so adapted, the method proceeds to block 318, wherein the determination is made if the visual inspection and/or environmental conditions are within desired thresholds. If the determination is made that the visual inspection and/or environmental conditions are outside desired thresholds, then the method may proceed to blocks 312, 314. If the determination is made that the visual inspection and/or environmental conditions are within desired thresholds, then the method 300 may proceed to block 319.

At block 319, a determination is made whether a medicament stored in a reservoir has exceeded its expiration date. This may involve comparing, with a controller onboard the drug delivery device, a current date with expiration date information stored in a memory onboard the drug delivery device. If the current date is determined to be later than or equal to the expiration date of the medicament, then the method may proceed to blocks 312, and 314. If the current date is determined earlier than the expiration date of the medicament, the method may proceed to block 320.

At block 320, a determination is made whether the drug delivery system is able to confirm the user identity. If the drug delivery system is so adapted, then the method 300 continues to block 322, and the determination is made if the user identity matches the authorization for the use of the drug delivery device. If the user is not identified as an authorized user at block 322, then the method 300 continues to block 324, where the drug delivery device is locked or remains locked, and block 326, where the information regarding the attempted unauthorized use is communicated to local and/or remote devices. If the user is identified as an authorized user, then the method 300 proceeds to FIG. 3B and block 328.

At block 328, a further determination is made as to whether the drug delivery system is enabled to confirm the temperature of the drug product or medicament. If the system is so adapted, then the method 300 continues to block 330. At block 330, a determination is made if the drug product or medicament temperature is within a target range for predictable delivery (neither too high nor too low). In some embodiments, this step may involve determining if the drug product or medicament temperature is below or above a target temperature. If the determination is made at block 330 that the temperature is not within the range for predictable delivery, then the method 300 continues to block 332, wherein a determination is made if the device is capable of heating or cooling the drug product to bring the temperature of the drug product or medicament within the target range. If the system is not so adapted, then the method proceeds to block 334, where the device may be locked or remain locked to allow passive heating or cooling to occur and the user may be alerted via, for example, an output unit coupled to the drug delivery device. Optionally, the system may also communicate the information to local and/or remote devices. If the system is enabled to permit heating or cooling, then the method proceeds to block 336, where the device may be locked or remain locked, heating or cooling may be initiated, and the user may be alerted. In some embodiments, the drug delivery device may include a heating element (e.g., an electrically conductive coil) coupled to a reservoir for heating the drug product or medicament. Whether passive or active heating or cooling (blocks 334, 336), the method 300 may continue to block 338, where delivery is delayed to provide time for the heating or cooling to occur before the method returns to block 330. According to certain embodiments, the method 300 may terminate after block 330 (in case of excessive temperature, for example) and may communicate that information to local and/or remote devices.

While the present embodiment of the method 300 may activate a heating or cooling element in response to a temperature of the drug product or medicament being outside a target temperature range, other embodiments may activate a heating or cooling element in response to other condition and/or conditional states of the drug delivery device. For example, a heating or cooling element may be activated in response to, for example, removal of a sterile barrier from a distal end of a delivery cannula of the drug delivery device, or contact between a housing of the drug delivery device and a patient's skin or clothing, or use of an actuator to trigger the drug delivery device.

In some embodiments, the temperature check performed at block 330 may involve an evaluation of the temperature history of the drug product to determine the range and duration of temperatures experienced by the drug product in the past (e.g., during storage, distribution, shipping etc.). If the temperature history of the drug product is unacceptable due to, for example, the drug product being exposed to elevated temperatures for several days during shipping, the controller 350 may lockout the drug delivery device 302 so that it cannot be used to deliver the drug product to a patient, and additionally, may control the communication module 352 to transmit a report to the local computing device 304 or the remote computing device 306 representative of the unacceptability of drug product's temperature history. In some embodiments, upon a determination that the temperature of the drug product exceeds a threshold temperature, the controller may begin a timer that runs until the temperature returns below the threshold temperature. If the duration of the timer exceeds a predefined time limit, the controller 350 may lockout the drug delivery device 302 and control the communication module 352 to transmit a report representative of the unacceptability of drug product's temperature history.

Returning to FIG. 3B, if the determination is made at block 328 that the device is enabled to determine that a housing of the drug delivery device is positioned against the patient's skin or clothing. If the drug delivery device is so adapted, then the method proceeds to block 342, and a determination is made whether a housing of the drug delivery device contacts the patient's skin or clothing. As discussed below in more detail, a sensor that forms a closed electrical circuit when positioned in contact with the patient's skin or clothing may be used to determine contact with the patient's skin or clothing. If the housing of the drug delivery device is determined to not be in contact with the patient's skin or clothing, then the method proceeds to block 344, and the drug delivery device may be locked and the user instructed (e.g., via an output unit coupled to the drug delivery device) to press the drug delivery device against the patient's skin or clothing. The method 300 may then proceed to block 346 wherein a time delay is provided for the user to reposition the drug delivery device before the method 300 returns to block 342 for a further determination of whether contact with the patient's skin or clothing exists. Alternatively, if the housing of the drug delivery device is determined to be in contact with the patient's skin or clothing, the method may proceed to block 350.

At block 350, a determination is made if the device is enabled to determine that the device is properly positioned on or oriented relative to the patient. If the device is so adapted, then the method proceeds to block 352, and a determination is made whether the device is properly disposed or oriented. In this regard, depending on the preferred insertion site, knowledge of the orientation of the device may be useful in providing a successful injection. For example, self-administration into the abdomen would most likely result in an orientation of an autoinjector axis approximately horizontal.

If the device is not properly disposed, then the method proceeds to block 354, and the device may be locked and the user instructed to reposition or reorient the device. The method 300 may then proceed to block 356 wherein a time delay is provided for the user to reposition the device before the method 300 returns to block 352 for a further determination relative to the position of the device. Alternatively, if the device is properly disposed, then the method may proceed to block 358, and any locks or lockouts that may have previously activated are deactivated.

The method 300 continues at block 360, wherein a determination is made whether the system is enabled to determine if the delivery has been triggered. If the determination is made that the system is so adapted, then the method proceeds to block 362, and a determination is made if the device has been activated or triggered. If the determination is made at block 362 that the device has not been triggered, then the method 300 may proceed to block 364 and the system may instruct the user to trigger the device. According to other embodiments, the drug delivery device may wait for a predetermined and/or preprogrammed time delay to occur before triggering the device automatically upon the completion of the time delay. According to still other embodiments, the method 300 may optionally determine if a timer has elapsed at block 365 to reduce the risk of contamination and infection, for example. According to such embodiments, the timer may be started upon the determination that the barrier has been properly removed at block 310 (or may be started upon the determination that the barrier has been removed, according to still further embodiments), and if the method 300 does not determine that the device has been triggered within a certain amount of time from that event, the method 300 may return to block 312, for example, as illustrated in FIGS. 3B and 3A. If it is determined at block 360 that the trigger has occurred, then the method proceeds to block 366, where the user may be notified of the triggering of the device and/or the date, time and location of the delivery may be stored or recorded. Optionally, this information may also be communicated to local and/or remote devices in communication with the system. The method 300 then continued to FIG. 3C.

A further determination may be made at block 368 whether the system is enabled to determine if the device has remained properly positioned on or oriented relative to the body. If the system is so adapted, then the method 300 continues to block 370, and a determination is made if the device is properly positioned on or oriented relative to the body. If the device is not properly positioned or oriented, then the method 300 may continue to block 372, where the user is alerted, e.g., via an output unit coupled to the drug delivery device, to reposition or reorient the device, and block 364, where a time delay is provided for the user to reposition or reorient the device, before returning to block 370 wherein the position or orientation of the device on the patient's body is determined. If the device is properly positioned or oriented, the method 300 may proceed to block 376. Optionally, the method 300 may repeat block 370 periodically during the time the device is administering the drug product to ensure that the device remains correctly positioned.

At block 376, a determination is made whether the system is enabled to determine if the administration is complete. If the system is so adapted, then the method 300 continues to block 378, and a determination is made if the delivery is complete. If the determination is made at block 378 that the delivery is not complete, then a further determination is made at block 380 whether the delivery can be completed. If the delivery is not complete but may be completed, then the method 300 returns to block 378 via block 382, where the device is permitted to continue to administer the drug product. If the delivery is not complete and cannot be completed (e.g., the device has been removed from the patient's skin), then the method 300 continues to block 384, and information regarding the drug and drug delivery may be communicated to a local and/or remote device. For example, information regarding whether certain operational states occurred (cannula inserted, delivery started, delivery partially completed), the timing of the operational states, and the amount of drug product that was administered may be communicated.

If the determination is made at block 378 that the delivery has been completed, then the method proceeds to block 386, where the system notifies the user, e.g., via an output unit coupled to the drug delivery device, that the delivery is complete. Furthermore, the method 300 communicates information regarding the drug delivery, the drug delivery device, and the drug product to local and/or remote devices at block 388. For example, the information may include that certain operational states occurred and the timing of the operational states. The method 300 may also verify that the device was correctly positioned throughout, where the system is enabled to make this determination. The method 300 may also pass to block 388 if the system is not enabled to determine if the administration of the drug product is complete, the assumption made that the drug delivery device having been determined to have passed through one or more of the preceding operational states necessarily leads to the conclusion that the delivery was completed.

The method 300 involves controlling various aspects of the drug delivery device including locking or unlocking the drug delivery device to prevent or allow administration of a medicament contained in a reservoir of the drug delivery device depending on various conditions and/or operational states of the drug delivery device. The locking steps provided by the method 300 may be implemented by one or more locks including, for example, a lock configured to prevent movement of a needle shield when the lock is activated, a lock configured to prevent movement of a plunger when the lock is activated, and/or a lock configured to prevent movement of an actuator when the lock is activated. Examples of locks capable of implementing the locking control described in the method 300 are described below in more detail in connection with FIGS. 16 and 17, for example. In addition, the active heating steps provided by the method 300 may be accomplished by one or more heating elements coupled to the drug delivery device and configured to increase the temperature of a medicament contained in the reservoir, as described below in more detail with respect to FIGS. 16 and 17, for example. Furthermore, aspects of the method 300 that involve alerting the user of relevant information may be accomplished via an output unit coupled to the drug delivery device, as described below in more detail in relation to FIGS. 16 and 17, for example.

Again, it should be noted that while the above description relates to a method including a series of states of for the devices and alternative actions that may depend on those states, the device need not determine each and every state or perform each and every action illustrated in the FIGS. 3A-3C. Rather, it will be recognized that one of ordinary skill in the art may omit or eliminate the determination of certain states or performance of certain actions, so as to result in a system that may control the drug delivery device based on or communicate a subset of the states described.

Furthermore, while the above description relates to a method in which the drug delivery device is controlled, for the most part, based on one or more conditions and/or operational states of the drug delivery device determined through use of one or more onboard sensors, the drug delivery device does not necessarily have to be controlled based on information collected by sensors, and may be controlled, for example, based on identity information representative of an identity of the patient (e.g., a patient's name, age, height, weight, password, fingerprint, biometrics, social security number, demographic, patient subgroup, etc.) an identity of the drug delivery device (e.g., a serial number of the drug delivery device, a type of discharge mechanism used by the drug delivery device, a date of manufacture of the drug delivery device, etc.) and/or an identity of the medicament to be stored within the reservoir of the drug delivery device (e.g., an expiration date of the medicament, a type of the medicament, a name of the medicament, etc.). The identity information may be stored onboard the drug delivery device in a memory device. In some embodiments, the drug delivery device may include an input unit that allows a patient to input identity information (e.g., the patient's password) which, if inputted correctly, may deactivate a lock used by the drug delivery device to prevent unauthorized administration of the medicament. Examples of such locks are described below in more detail in connection with FIGS. 16 and 17.

Figure 4:
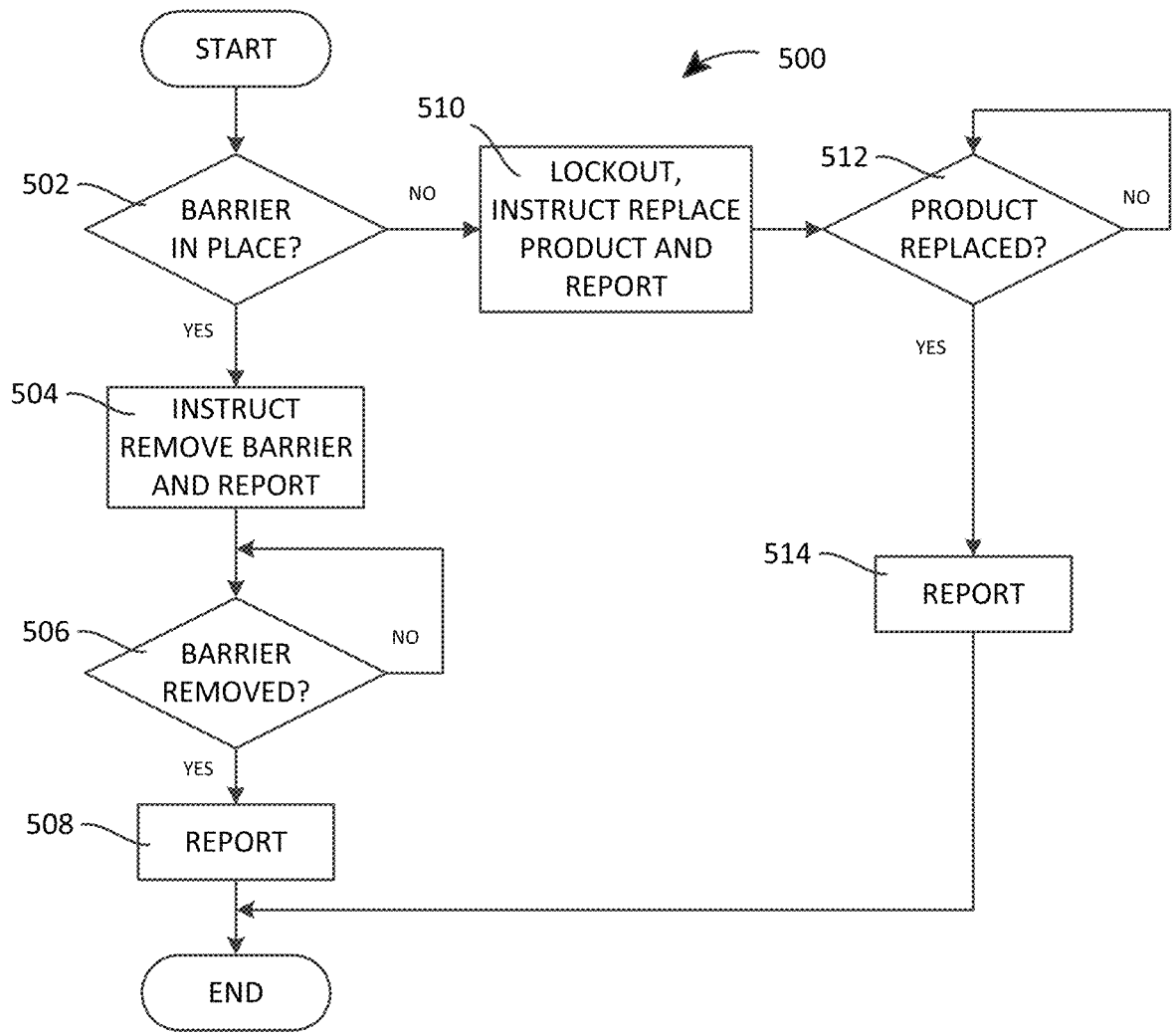
FIG. 4 is a block diagram of a method of operating a drug delivery system according to another embodiment of the disclosure.

Turning first to FIG. 4, a method 500 is illustrated wherein the drug delivery system is adapted or programmed to provide instruction to the patient or user, through the use of an output devices such as a light emitting diode, display, speaker or other device, and to communicate with a computing device (e.g., mobile device 110 or computing device 114) over a communication link (e.g., 112 or 116) to transmit a report to that computing device. The method 500 is focused on a single issue: whether the sterility of the device is intact. The method 500 determines if the sterility of the device is maintained based on whether a barrier, in the form of a needle cap, is disposed over the second end of a cannula that is intended to be inserted into the patient.

The method 500 begins by making a determination whether the needle cap is in place at block 502. This determination may be made, at least in part, on whether a signal has been received by a controller adapted or programmed to carry out the method 500 from a switch or other proximity sensor that abuts a structure of an autoinjector when the needle cap is properly disposed over the end of the needle. If the determination is made at block 502 that the needle cap is in place, then the method 500 continues to block 504 and the user may be instructed to remove the needle cap, for example by illuminating one or more light emitting diodes visible to the patient or user of the drug delivery device. The controller may also cause a transmitter (which is at least capable of one-way communication, and may be capable of two-way communication—i.e., a transceiver) to transmit a report at block 504 to one or more computing devices in communication with the transmitter representative of the fact that the sterility of the device is intact. For example, the transmitter may be a near field transmitter, such as may use the Bluetooth or similar protocol.

The method 500 may continue at block 506, where the controller determines if the needle cap has been removed after the patient or user was instructed to remove the needle cap. For example, the controller may determine that the needle cap has been removed when a different signal (or no signal) is received from the switch or other proximity sensor. When the controller determines that the needle cap has been removed, the method continues to block 508 where the controller causes the transmitter to transmit a report representative of the fact that the needle cap has been removed after the sterility of the device was confirmed.

As illustrated in FIG. 4, the method 500 includes a different set of actions if the controller determines at block 502 that the barrier is not in place, e.g., the needle cap is not disposed about the end of the needle at the beginning of the process. If such a determination is made at block 502, then the method 500 continues at block 510, where the controller locks the drug delivery device, instructs the patient or user to replace the product container, and causes the transmitter to transmit a report representative of the fact that the sterility of the device is not intact. As was the case with the action taken at block 504, the controller may instruct the patient or user to replace the product by illuminating a light emitting diode. The controller may lock the product by preventing the operation of one or more other assemblies necessary to administer the drug to the patient; for example, the controller may prevent the needle from being inserted into the patient. The controller then waits until a determination is made at block 512 that the product has been replaced. The controller may determine that the product has been replaced depending on whether a switch proximate to the container has changed states, which the switch would do only if the container was replaced. When the controller determines that the product has been replaced, the method 500 continues to block 514, and the controller causes the transmitter to transmit a report to one or more computing devices in communication with the drug delivery system representative of the fact that while the sterility of the device was not initially intact, the product has been replaced.

Figure 5:
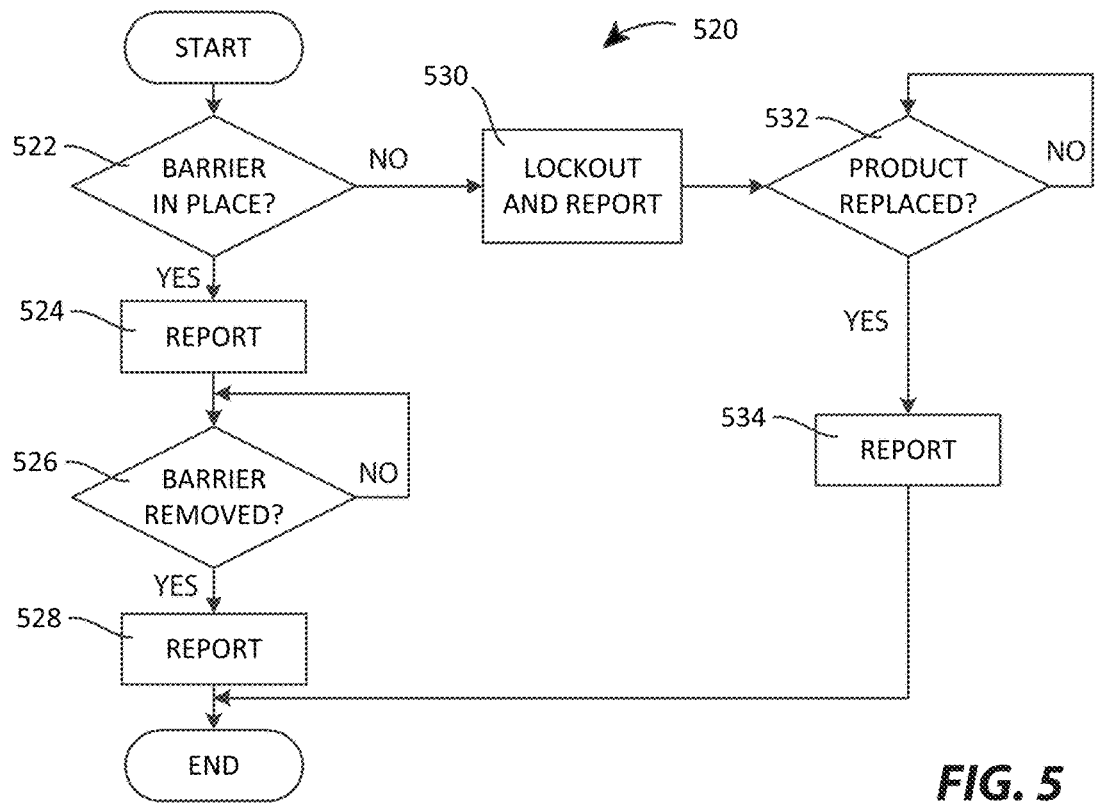
FIG. 5 is a block diagram of a method of operating a drug delivery system according to a still further embodiment of the disclosure.
Figure 6:
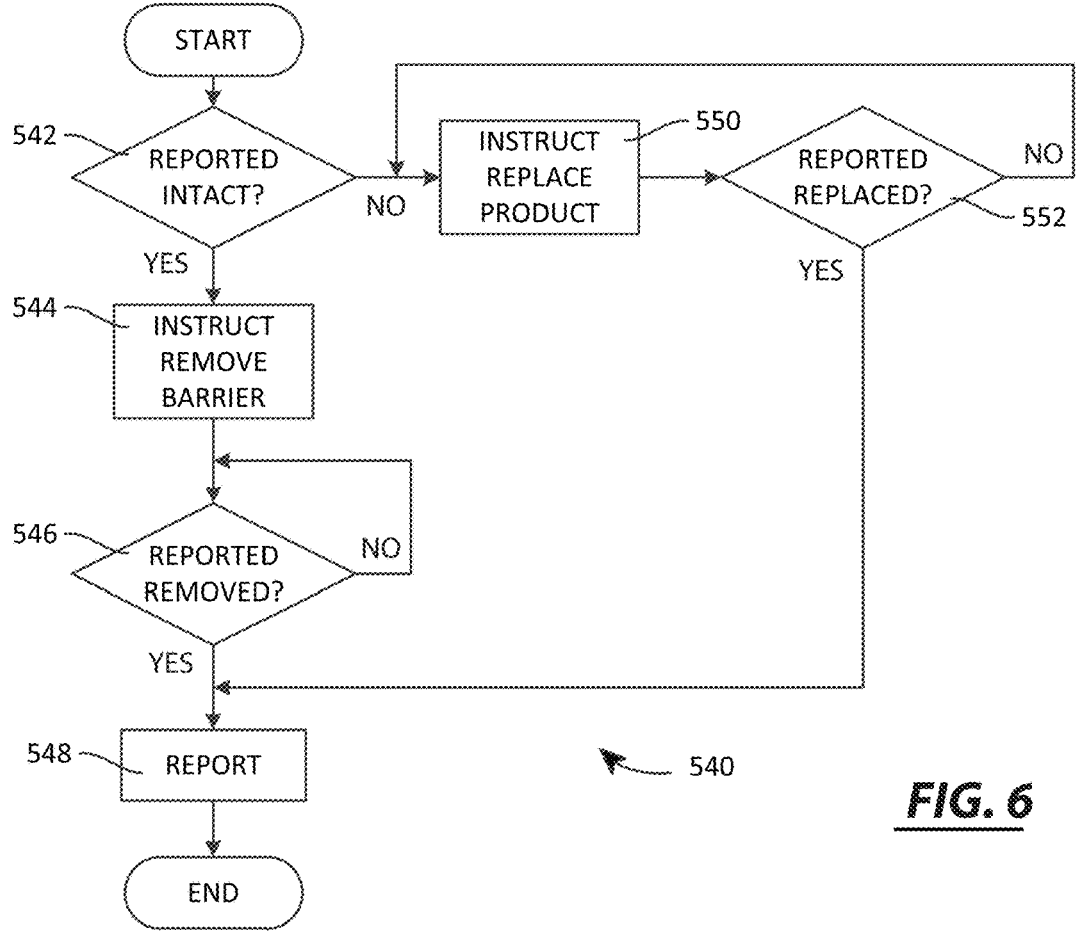
FIG. 6 is a block diagram of a method of operating a computing device according to an embodiment of the disclosure, the computing device in communication with the drug delivery system operating according to the method of FIG. 5, for example.

By contrast to the method 500 of FIG. 4 which is carried out by a drug delivery system with a controller adapted or programmed to carry out the method 500, the methods 520, 540 of FIGS. 5 and 6 are carried out by a drug delivery system and an associated computing device, which drug delivery system is adapted or programmed to carry out the method 520 and which computing device is adapted or programmed to carry out the method 540. It will be recognized that the methods 520, 540 may limit the amount of hardware required by the drug delivery system by shifting interactive events with the patient or user to the computing device, which may be in the form of a mobile device 110, to take advantage of the output devices or peripherals already associated with the computing device.

The method 520 of FIG. 5 begins at block 522, with a controller that is part of the drug delivery system determining if the barrier is intact, i.e., the needle cap is disposed over the end of the needle. If the determination is made that the needle cap is initially in place, the controller causes a transmitter to transmit a report to the computing device representative of the fact that the needle cap is disposed over the end of the needle at block 524.

The method 540 of FIG. 6 begins with receipt of the report from the drug delivery device at block 542. If the computing device determines that a report has been received and that the report received is representative of the fact that the needle cap is initially in place, the method 540 proceeds to block 544, wherein the computing device controls an associated display to display a message to the user or patient that the needle cap should be removed. According to one embodiment of the disclosure, where the computing device is a hand-held mobile device, such as a smart phone, the message may be displayed on the display associated with the mobile device in the form of an image that may include words, pictures or a combination thereof representative of the instruction to remove the needle cap. The method 540 then passes to block 546, where the computing device waits to receive a report from the drug delivery system representative of the fact that the needle cap has been removed.

Returning to FIG. 5, the method 520 continues at block 526 where the controller associated with the drug delivery device determines whether the needle cap has been removed after the initial determination was made that the needle cap had not been removed initially. The controller begins this determination upon completion the transmission of the report at block 524, and thus the determination is not dependent upon the patient or user receiving the instruction via the computing device to remove the needle cap, although according to certain embodiments the determination of the controller whether the needle cap has been removed at block 526 could be made dependent upon the user first receiving a message from the computing device that the needle cap should be removed. When the controller determines that the needle cap has been removed, the method 520 continues at block 528, where a report is transmitted to the computing device representative of the fact that the needle cap has been removed.

Returning to FIG. 6, upon determination at block 546 that a report has been received by the computing device that the needle cap has been removed, the method 540 may continue at block 548 where a report is transmitted, for example by the mobile device 110 in FIG. 1 to the server 104 in FIG. 1 via the network 118, representative of the fact that the drug delivery system is ready for use. According to other embodiments the report may be more particular, e.g., representative of the fact that the barrier was initially intact and that the needle cap had been subsequently removed.

In the alternative, the controller of the drug delivery system may determine at block 522 that the barrier is not initially in place. If so, the controller may lock the drug delivery device and cause the transmitter to transmit a report to the computing device representative of the fact that the barrier was not initially in place at block 530. The controller of the drug delivery system may then determine at block 532 if the product has been replaced.

Meanwhile, the computing device has received the report representative of the fact that the barrier is not initially in place at block 542, and the method 540 has continued to block 550, where the device controls an associated display to display a message to the user or patient that the product should be replaced. According to the embodiment of the disclosure discussed above, where the computing device is a hand-held mobile device, the message may be displayed on the display associated with the mobile device in the form of an image that may include words, pictures or a combination thereof representative of the instruction to replace the product. The method 540 then continues at block 552, where the computing device determines if a report has been received from the drug delivery system representative of the fact that the drug product has been replaced.

Shifting again to FIG. 5, once the determination is made at block 532 that the product has been replaced, the controller may cause the transmitter to transmit at block 534 a report representative of the fact that the product has been replaced. When the computing device determines that the report has been received at block 552 in FIG. 6, the method 540 continues to block 548, where a report is transmitted to the server 104, for example, representative of the fact that the drug delivery device is ready for use.

It is not a requirement of the disclosure that the determinations regarding condition state information, operational state information or other information be made by a controller that is housed in the same housing as the drug delivery device, or the computing device for that matter. In fact, the controller that makes the determination regarding a particular state of the drug delivery device may be disposed in a housing that is detachable from the drug delivery device. For example, again with reference to an embodiment that determines if a sterility barrier is intact based on whether a needle cap is disposed over the end of a needle, a method 560 is provided in FIG. 7 for a controller that is disposed in the needle cap and that is coupled to a sensor, such as a switch or other proximity sensor, that will determine when the needle cap is removed from the end of the needle.

Figure 8:
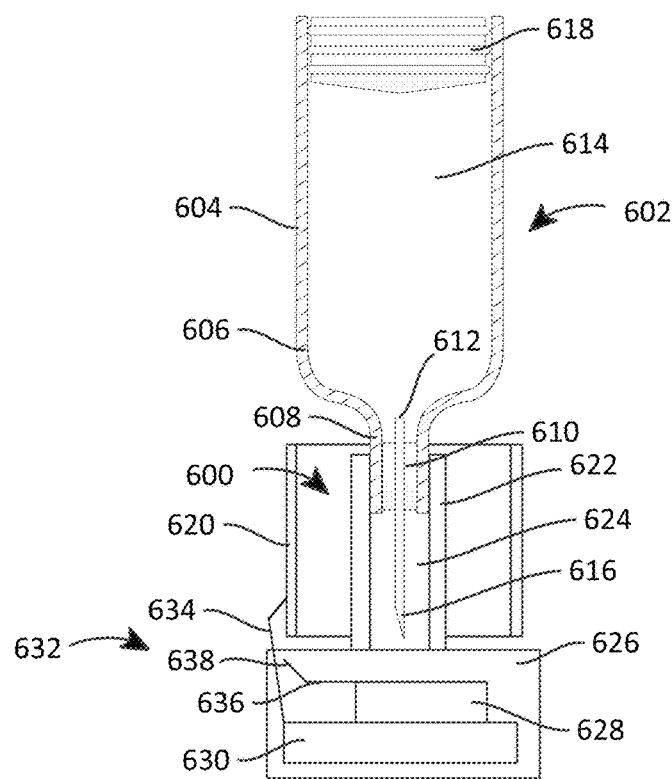
FIG. 8 is a partial cross-sectional view illustrating an embodiment of a system used to carry out, for example, the method of FIG. 7.

Before discussing the method 500, it may be helpful to discuss the illustration of FIG. 8, which includes the needle cap 600 and portions of an embodiment of an autoinjector 602 with which the needle cap 600 is used. It will be recognized that much of the construction of the autoinjector 602 has been omitted to facilitate discussion of the structure and operation of the needle cap 600. The autoinjector 602 may include other structures, subassemblies, and/or assemblies that may, for example, insert a cannula into a patient and force a drug or medicament from a reservoir through the cannula into the patient. In this regard, reference is made to the embodiment of an autoinjector illustrated in FIG. 12, below.

According to the simplified presentation of the autoinjector 602 illustrated in FIG. 8, the autoinjector includes a reservoir 604 in the shape of a syringe. Thus, the reservoir 604 is defined by a substantially cylindrical wall 606 having a hub 608 in which a cannula 610 is disposed and fixed (or staked). The cannula 610 has a first end 612 in fluid communication with an interior 614 of the reservoir 604, and a second end 616 that is intended to be inserted into the patient. The reservoir 604 may also include a plunger 618 that moves along the reservoir 604 to force fluid out of the reservoir 604 through the cannula 610 into the patient. The autoinjector 602 also includes a structure 620 that cooperates with structures of the needle cap 600, which structure 620 is disposed about the cannula 610. The structure 620 may be, for example, a needle shield (explained in greater detail relative to the embodiment of FIG. 12), or a portion of a housing of the autoinjector 602.

The needle cap 600 includes an annular collar (or hub) 622 in which the hub 608 of the reservoir 604 is received. The collar 622 fits snugly about the hub 608 at one end and receives the second end 616 of the cannula 610 in an interior space 624 of the collar 622. The collar 622 may also be described as disposed about the second end 616 of the cannula 610. The collar 622 is attached to a body 626 (that may be in the form of a housing) in which is disposed a power supply 628 and a controller/communication module assembly 630. The power supply 628 and the module assembly 630 may be coupled through the use of a switch 632, which as illustrated includes first and second contacts 634, 636. When the contacts 634, 636 abut each other, the module assembly 630 is coupled to the power supply 6268.

In particular, as is illustrated in FIG. 8, the first contact 634 abuts the needle shield 620 with the needle cap 600 disposed about the second end 616 of the cannula 610, and thus does not abut an end 638 of the second contact 636 in this first state. When the needle cap 600 is removed (second state), the first contact 634 is free to move in the direction of the second contact 636 and to abut the end 638 of the second contact 636. With the contacts 634, 636 abutting each other, the circuit is closed and the module 630 is coupled to the power supply 628.

Figure 7:
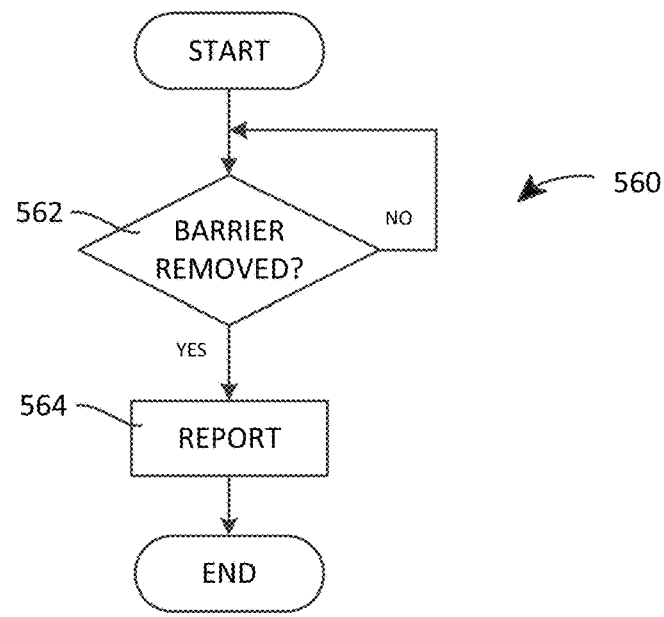
FIG. 7 is a block diagram of a method carried out by a drug delivery system according to another embodiment of the disclosure.

According to the method 560 of FIG. 7, the controller of the module 630 may determine based on a signal received (or not received) from the switch or sensor 632 that the needle cap 602 is disposed over the end 616 of the needle 610 at block 562. The sensor may be extremely simple in regard to this embodiment, and may even include a pair of contacts 634, 636 that are ordinarily disposed on opposite sides of the needle shield or housing 620 or are otherwise spaced apart by the needle shield or housing (see FIG. 8), but that are connected or coupled when the needle cap 602 is removed (such that the needle shield or housing 620 is no longer disposed between the contacts 634, 636 or no longer prevents their contact with each other). In fact, according to such an embodiment, the sensor 632 and the controller of the module assembly 630 may be the same structure. When the module 630 determines that the needle cap 602 has been removed, the module assembly 630 controls the associated transmitter to transmit a report representative of the fact the needle cap 602 has been removed at block 564. Again, according to the embodiment where the contacts 634, 636 are the sensor 632, the connection or coupling of the contacts 634, 636 may close a circuit including the transmitter 630 and a power supply 628 (e.g., a battery), which causes the transmitter 630 to transmit the required report.

Figure 9:
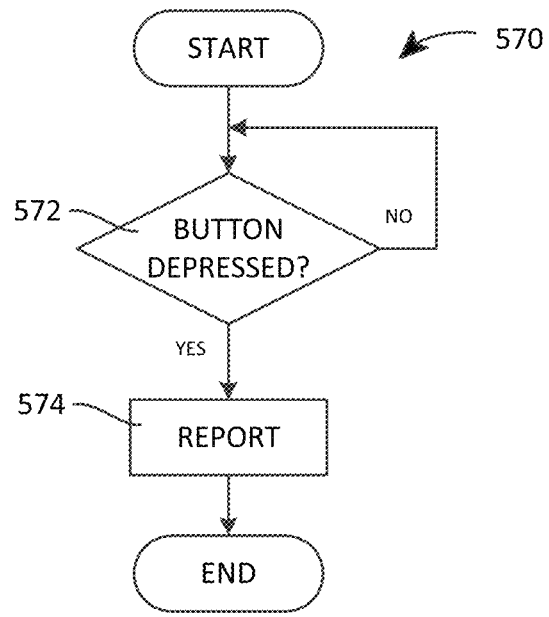
FIG. 9 is a block diagram of a method carried out by a drug delivery system according to yet another embodiment of the disclosure.
Figure 10:
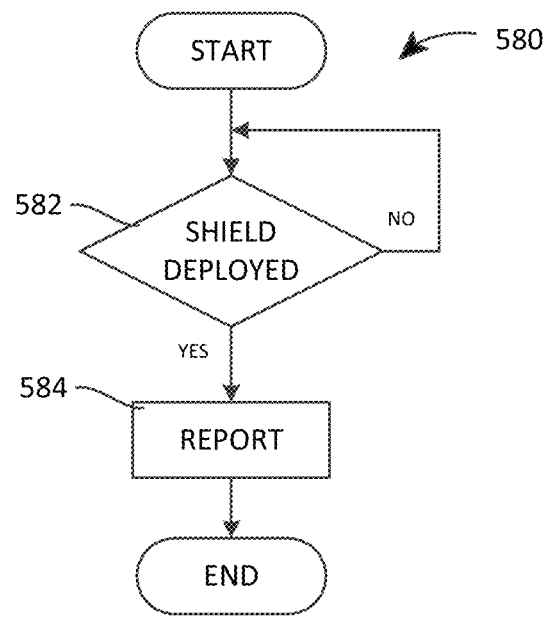
FIG. 10 is a block diagram of a method carried out by a drug delivery system according to a further embodiment of the disclosure.

FIGS. 9 and 10 illustrate methods similar to that of FIG. 7, in that each method is focused on the determination of a single condition or operational state of the drug delivery device, and transmits a report when the condition or operational state occurs. In this regard, the method 570 focuses on determining if the drug delivery device has been triggered by determining if an actuator (e.g., a button) has been depressed, and the method 580 focuses on determining if a needle shield that is part of the drug delivery device has deployed (which needle shield deployment ordinarily occurs after the drug delivery has been completed and the drug delivery device is removed from against the skin of the patient). As was also the case with the embodiment of FIG. 9, the embodiments of FIGS. 9 and 10 may be carried out through the use of a sensor in the form of a switch or pair of contacts that closes a circuit including the transmitter and a power supply upon determination of the operational state.

Figure 12:
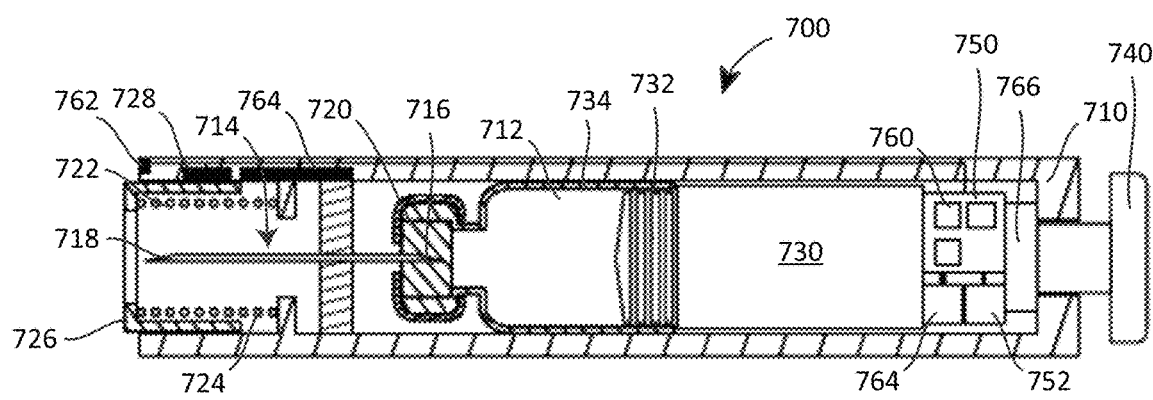
FIG. 12 is a cross-sectional view of an embodiment of a drug delivery system including an autoinjector.

Thus, according to FIG. 9, the method 570 begins at block 572, where the controller/switch determines if the actuator has been depressed according to whether the switch state has changed in accordance with the switch contacting a portion of the drug delivery device that would not ordinarily be in contact with the switch unless the button was depressed (see, e.g., switch 766 in FIG. 12). For example, the switch may be attached to and carried on the actuator (e.g., button), such that when the actuator moves relative to the housing of the drug delivery device, the switch comes in contact with a structure of the drug delivery device that changes its state. When this occurs, the method 570 continues at block 574, and the controller/switch causes the transmitter to transmit a report representative of the fact that the drug delivery device has been trigger by closing a circuit between the transmitter and a power supply (e.g., a battery, capacitor or inductive power supply). The triggering of the drug delivery device may coincide with the activation of a drive associated with a reservoir to cause a medicament to be ejected from the reservoir, although the activation of the drive need not coincide with the triggering of the drug delivery device.

Figure 11A:
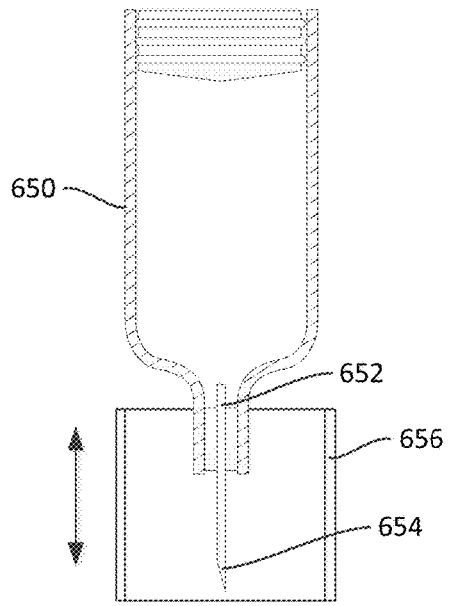
FIGS. 11A and 11B are schematic views of an embodiment of a system used to carry out, for example, the method of FIG. 10.
Figure 11B:
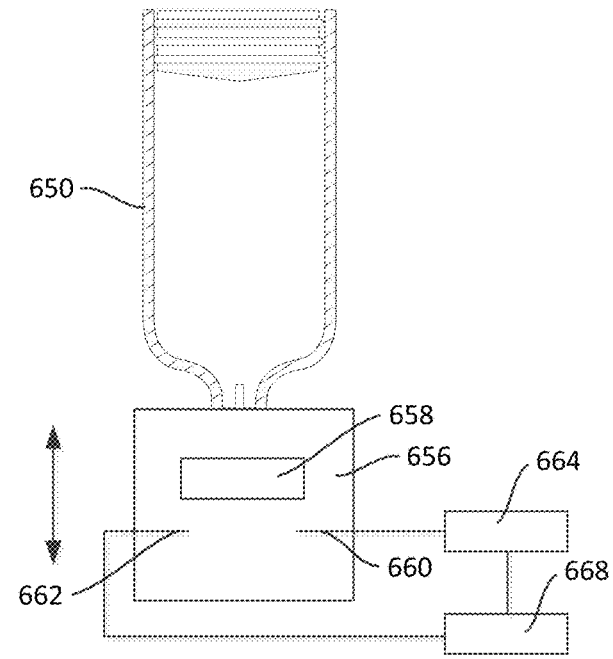

In a similar fashion, according to FIG. 10, the method 580 begins at block 582, where the controller/contact pair determines if the needle shield has been deployed according to whether the contact pair has been connected or coupled together. As illustrated in FIGS. 11A and 11B, an embodiment of a drug delivery device system for carrying out the method 580 may include a reservoir 650 in the form of a syringe, having a cannula 652 in the form of a needle with an end 654 that is to be inserted into the patient (see FIG. 11A) and a needle shield 656 that includes a conductive pad 658 that connects the contact pair 660, 662 when the needle shield 656 is deployed; alternatively, one of the contact pair may be disposed on the housing of the drug delivery device and the other of the contact pair may be disposed on the needle shield, such that when the needle shield moves relative to the housing of the drug delivery device, the contacts are connected or coupled. When this occurs, the method 580 continues at block 584, a circuit including a power supply 664 and a controller and transmitter module assembly 668 is closed, causing the transmitter of the module 668 to transmit a report representative of the fact (under most circumstances) that the drug delivery has been completed.

According to one alternative embodiment, using the structure of FIGS. 11A and 11B, a repositioning of the contacts 660, 662 relative to the conductive pad 658 would permit the system of FIGS. 11A and 11B to determine if the needle shield 656 has been moved relative to the end 654 of the cannula 652 so as to determine that the cannula 652 has been inserted into the patient. Rather than movement of the needle shield 656 toward the bottom of the page causing the conductive pad 658 to close the circuit between the contacts 660, 662, movement of the needle shield 656 toward the top of the page would cause the conductive pad 658 to close the circuit between the contacts 660, 662, which would cause the module assembly 668 to transmit a report representative of the fact that the needle has been inserted. As a further alternative embodiment, two sets of contacts may be included, the sets spaced from each other in the direction of movement of the needle shield 656, with the set of contacts closest to the top of the page being used to determine if the needle shield 656 has been moved relative to the end 654 of the cannula 652 indicative of insertion of the end 654 into the patient, and the set of contacts closest to the bottom of the page being used to determine if the needle shield is disposed about the end 654 of the cannula 652 indicative of the completion of the delivery to the patient.

The methods discussed above may be carried out by a variety of different drug delivery systems. FIGS. 12 and 13-15 illustrate two examples of such systems, the embodiment of FIG. 12 including a drug delivery system including a drug delivery device in the form of an autoinjector, and the embodiment of FIGS. 13-15 including a drug delivery system including a drug delivery device in the form of an on-body injector or infuser.

Referring first to the drug delivery device of FIG. 12, the autoinjector 700 includes a housing 710 in which may be disposed assemblies or structures that insert or enable insertion of a cannula into the patient, and that inject a drug or medicament from the reservoir through the cannula into the patient. According to certain embodiments, the same assemblies or structures that insert the cannula into the patient may also allow flow of the drug or medicament from the reservoir through the cannula into the patient. The autoinjector 700 may also include assemblies or structures that connect the cannula to the reservoir, that withdraw the cannula into the housing 710, or that deploy other structures that will prevent contact with the cannula once the cannula has been removed from the patient. Further additional assemblies and structures are also possible. The specific embodiment of the autoinjector 700 discussed below is thus by way of example and not by way of limitation. For example, the autoinjector 700 may lack assemblies or structures that insert the cannula (e.g., needle) into the patient, the insertion of the cannula into the patient resulting from the cannula being substantially fixed relative to the housing of the autoinjector 700 and the autoinjector 700 being moved in the direction of the patient.

The drug delivery system 700 includes a reservoir 712 and a cannula 714 having a first end 716 that may be connected or connectable in fluid communication to the reservoir 712 and a second end 718 that may be inserted into a patient. The cannula 714 may be, for example, a rigid needle having a beveled edge that may be sized such that the second end 718 of the cannula 714 is received under the skin so as to deliver a subcutaneous injection of the drug within the reservoir 712. The first end 716 of the cannula 714 may be disposed through a wall 720 of the reservoir 712, and thus be connected in fluid communication with the reservoir 712. As illustrated, the first end 716 of the cannula 714 may be disposed only partially through the wall 720 (which wall 720 may be a resealable septum or stopper, for example) such that the first end of the cannula 714 may not be connected in fluid communication until the second end 718 of the cannula 714 is inserted into the patient. In such a circumstance, the first end 716 of the cannula 714 may thus be described as connectable in fluid communication with the reservoir 712, although it will be recognized that there are other mechanisms by which the first end 716 of the cannula 714 may be connectable, but not connected, in fluid communication with the reservoir 712.

The drug delivery device 700 includes a shield 722 that may be deployed at least after the injection has been completed to limit access to the second end 718 of the cannula 714. According to certain embodiments, the shield 722 may have a biasing element 724 (such as a spring) that extends the shield 722 from the housing 710 such that a distal end 726 of the shield 722 extends beyond the second end 718 of the cannula 714 except when the shield 722 is disposed against the skin and the injection of the cannula 714 is actuated. In fact, the injection of the cannula 714 may be actuated according to certain embodiments of the autoinjector 700 by disposing the distal end 726 of the shield on or against the skin of the patient. The autoinjector 700 may also include a lock 728 that is associated with the shield 722 and which limits the movement of the shield 722 relative to the housing 710 of the autoinjector 700 such that the distal end 726 of the shield 722 extends from the housing 710 a sufficient distance to limit or prevent contact with the second end 718 of the cannula 714 after the cannula 714 has been removed from the skin of the patient after the drug has been delivered.

The drug delivery device 700 also includes at least one drive 730 that may be used to insert the second end 718 of the cannula 714 into the skin of the patient, and to inject the drug or medicament from the reservoir 712 through the cannula 714 into the patient. The drive 730 may include one or more springs, according to certain embodiments. According to other embodiments, the drive 730 may include a source of pressurized gas or a source of a material that undergoes a phase change, such that the escaping gas or phase changing material provides a motive force that may be applied to the reservoir 712 to eject the drug therefrom. According to still other embodiments, the drive 730 may include an electromechanical system, such as may include a motor for example, although such an electromechanical system may be more appropriate for the on-body autoinjector or infuser described in greater detail below. Other embodiments for the drive 730 will be recognized.

The drive 730 may cooperate with a wall 732 of the reservoir 722 to move that wall 732 toward the patient's skin. In accordance with such an embodiment, the wall 732 may be a stopper that is received within a bore 734, and which may move along the bore 734 from a first end to a second end to inject the drug from the reservoir 712. The drive 730 may also cooperate with the stopper 732 and/or the bore 734 to move the reservoir 712 relative to the housing 710 so as to move the second end 718 of the cannula 714 relative to the housing 710 and into the patient. According to those embodiments wherein the drive 730 cooperates with the stopper 732, this may occur before the first end 716 of the cannula 714 is in fluid communication with the reservoir 712. According to those embodiments wherein the drive cooperates with the bore 734, the drive may include one component (e.g., first spring) that cooperates with the bore 734 to move the reservoir 712 and cannula 714 relative to the housing 710, and a second component (e.g., second spring) that cooperates with the stopper 732 to move the stopper 732 relative to the bore 734.

The drive 730 is associated with an actuator 740. The actuator 740 activates the drive to cause the drive 730 to insert the cannula 714 and inject the drug from the reservoir 712 through the cannula 714 into the patient. The actuator 740 may, according to certain embodiments, be the shield 722. According to other embodiments, such as the embodiment illustrated, the actuator 740 may be a button that may be depressed by the user once the autoinjector 700 is disposed on or against the patient's skin. While the embodiment illustrated in FIG. 12 has the actuator 740 disposed at one end of the device, the actuator 740 could be disposed on the side of the device as well.

As illustrated, the reservoir 712, biasing element 724, lock 728, and the drive 730 are disposed within the housing 710, along with at least part of the cannula 714. Also disposed within the housing 710 is a controller 750, a communication module 752, and at least one sensor or switch. According to the embodiment illustrated, four sensors are included: a temperature sensor 760, a proximity sensor 762 (to determine the presence of a needle cap (not shown) or the position of the needle shield 722) and two orientation sensors 764. In addition, a switch 766 is also provided to determine if the button 740 has been depressed. The controller 750 is coupled to the communication module 752, the sensors 760, 762, 764 and the switch 766. The controller 750, communication module 752, one or more of the sensors 760, 762, 764 and the switch 766 may be packaged together as a single module, or each component may be fabricated separately and coupled once the components are disposed within the housing 710. According to certain embodiments, each component may be integrated into the structure of the device 702 associated with that component (e.g., the sensors 762, 764 may be integrated into the shield 722) and the location of the sensors in FIG. 12 is merely illustrative.

The controller 750 may include at least one processor and memory. The controller 750 may also include or be coupled to a power supply, e.g. a battery. The processor may be programmed to carry out the actions that the controller is adapted to perform and the memory may include one or more tangible non-transitory readable memories having executable instructions stored thereon, which instructions when executed by the at least one processor may cause the at least one processor to carry out the actions that the controller 750 is adapted to perform. Alternatively, the controller may include other circuitry that carries out the actions that the controller is adapted to perform.

The communication module 752 may be any of a number of different communication modules used to communicate with the mobile device 110 and/or the computing device 114 (see FIG. 1). According to one embodiment, the communication module 752 may be a Bluetooth/Bluetooth Low Energy module that is on-board with the controller 750. The communication module 752 is used to transmit information from the autoinjector 700 to the mobile device 110 or computing device 114. Alternatively, other protocols may be used by the communication module 752, such as RFID, Zigbee, Wi-Fi, NFC, and others.

Given the presence of the temperature sensor 760, the proximity sensor 762, the orientation sensors 764, and the switch 766, the controller 750 may adapted or programmed to carry out most, of the method 300 illustrated in FIGS. 3A-3C, as well as the methods illustrated in FIGS. 4-6, 9 and 10, with the provision of suitable output devices, as required.

Figure 12A:
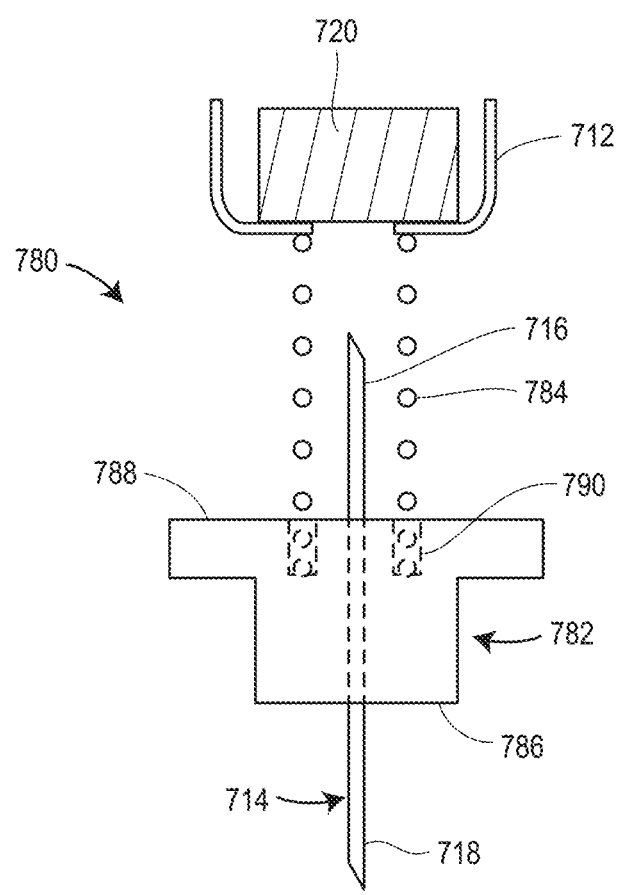
FIG. 12A is a cross-sectional view of an alternative cannula subassembly for the drug delivery system of FIG. 12.

While the cannula 714 of the drug delivery system 300 illustrated in FIG. 12 is fixed relative to the reservoir 712 and thus in fluid communication with the reservoir 712 at all times, other embodiments may be arranged differently, for example, with the cannula 714 being movable relative to the reservoir 712. FIG. 12A illustrates a cannula subassembly 780 which can be implemented in the drug delivery system 700 of FIG. 12 and which allows the first end 716 of the cannula 714 to be moved into fluid communication with the reservoir 712 when the second end 718 of the cannula 714 is inserted into the patient and moved out of fluid communication with the reservoir 712 when the second end 718 of the cannula 714 is removed from the patient. To achieve this functionality, the cannula subassembly 780 includes a spring seat 782 fixed to the cannula 714 and a spring 784 positioned between the spring seat 782 and the distal end of the reservoir 714. The spring seat 782 may have a distal end surface 786 configured to be pressed against the patient's skin and a proximal end surface 788 in contact with the spring 784. As illustrated in FIG. 12A, the proximal end surface 788 may include a guide channel or groove 790 to receive the distal end of the spring 784 and prevent the spring 784 from sliding off of the spring seat 782. Prior to delivery of the medicament to the patient, the spring 784 may be in an un-compressed, natural state which biases the spring seat 782 away from the reservoir 712, as seen in FIG. 12A. Accordingly, the first end 716 of the cannula 714 is spaced apart from the reservoir 712 and not in fluid communication with the reservoir 712 when the spring 784 is not compressed. When the drug delivery system 700 is used to deliver the medicament to the patient, the patient's skin pushes against the distal end surface 786 of the spring seat 782, thereby compressing the spring 784 and moving the cannula 714 in the distal direction until the first end 716 of the cannula 714 penetrates the septum 720 and enters the interior of the reservoir 712. In this configuration, fluid communication is established between the cannula 714 and the reservoir 712 so that the cannula 714 can deliver medicament in the reservoir 712 to the patient. When the drug delivery system 700 is removed from the patient's body, the spring 784 expands and returns to its natural, un-compressed state shown in FIG. 12A. As a result, the spring 784 pushes the spring seat 786 away from the reservoir 712 and the first end 716 of the cannula 714 is removed from the reservoir 712. Accordingly, the first end 716 of the cannula 714 is moved out of fluid communication with the reservoir 712. One benefit of the cannula subassembly 780 is that premature removal of the drug delivery device 700 from the patient's skin during medicament delivery is less likely to result in wasteful discharge of the medicament. This is because premature removal of the drug delivery system 700 from the patient's skin causes the cannula subassembly 700 to automatically moved the cannula 714 out of fluid communication with the reservoir 712.

Figure 13:
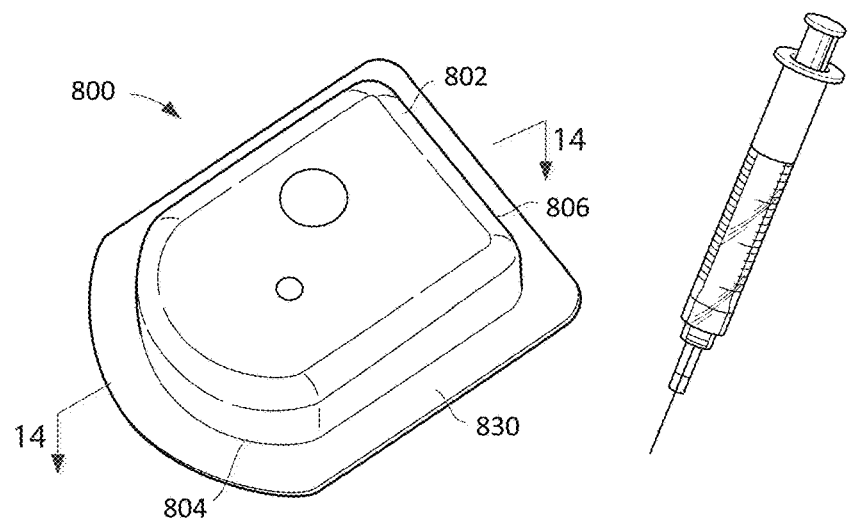
FIG. 13 is a perspective view of an embodiment of a drug delivery system including an on-body injector.

FIG. 13 illustrates a drug delivery system 800. The system 800 may be a wearable, disposable system. The system 800 may include a disposable housing 802 that may be attached to a patient or wearer with adhesive, for example.

Figure 14:
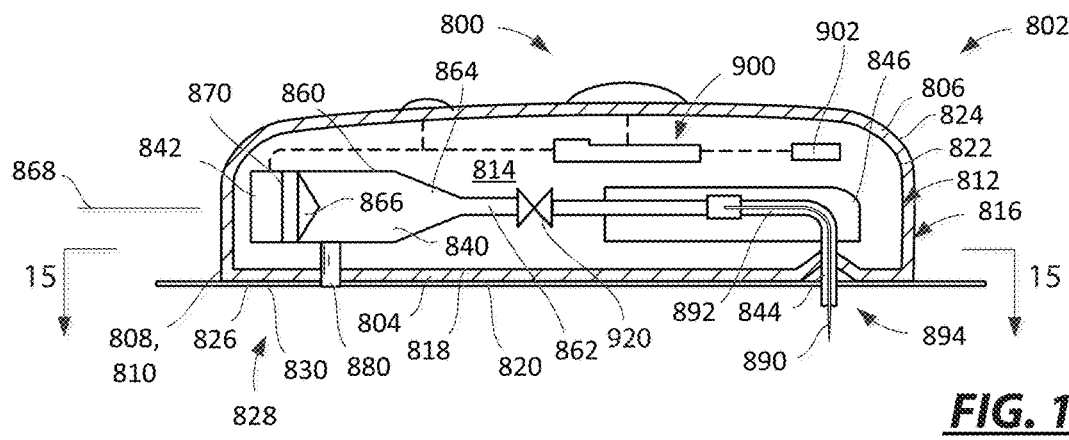
FIG. 14 is a cross-sectional view of the drug delivery device of FIG. 13 taken along line 14-14.

The disposable housing 802 may be made of a plastic material. As seen in FIG. 14, the housing 802 may be defined by two sections, a plate 804 that is applied against the wearer's skin, and a dome 806 that is attached to the plate 804, preferably by a seal at an interface between a peripheral edge 808 of the plate 804 and a peripheral edge 810 of the dome 806.

As shown in FIG. 14, the housing 802 has an interior surface 812 defining an interior space 814, and an exterior surface 816. In particular, the plate 804 has an interior surface 818 and an exterior surface 820, and the dome 806 has an interior surface 822 and an exterior surface 824. According to the illustrated embodiment, the interior surface 812 of the housing 802 is defined by the interior surfaces 818, 822 of the plate 804 and the dome 806, while the exterior surface 816 of the housing 802 is defined by the exterior surfaces 820, 824 of the plate 804 and dome 806.

Figure 15:
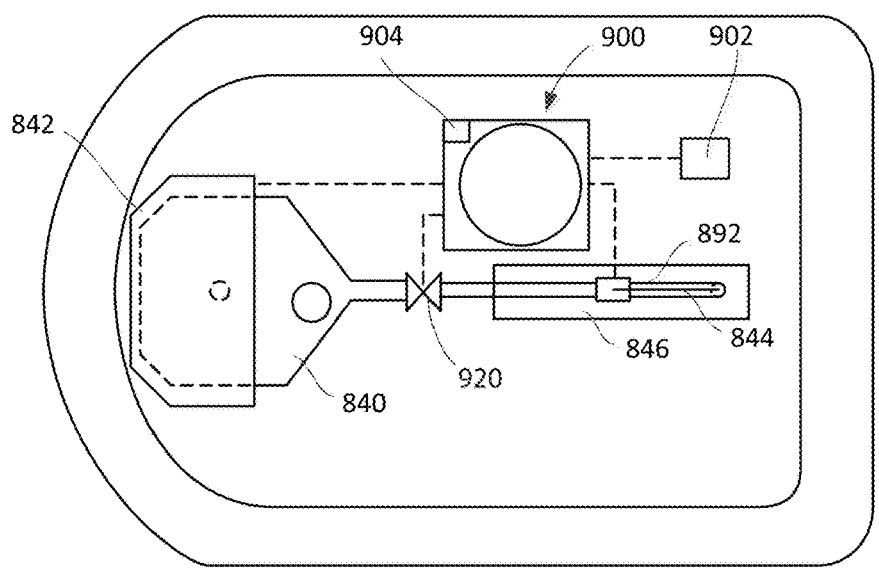
FIG. 15 is a cross-sectional view of the drug delivery device of FIG. 14 taken along line 15-15.

As noted above, the housing 802 may be attached to the skin of the wearer. In particular, an adhesive may be used. The adhesive may be adapted to releasably secure the housing to skin during a single application. As shown in FIG. 15, the adhesive is disposed in a layer 826 on a portion 828 of the exterior surface 816 of the housing 802, and in particular on the exterior surface 820 of the plate 804. The adhesive is covered with a removable, disposable sheet 830 prior to application of the housing 802 to the skin of the wearer.

As seen in FIGS. 14 and 15, a reservoir 840, a drive 842, a cannula (or structure, see below) 844, and an inserter 846 are disposed in the housing 802. According to the illustrated embodiment, the reservoir 840 may be defined at least in part by a combination of a rigid-walled cylinder or bore 860 having a port 862 at a first end 864 and a plunger 866 fitted to move along a longitudinal axis 868 of the cylinder 860 between a second end 870 and the first end 864 to force drug out of the reservoir 840 through the port 862 (FIG. 13). The movement of the plunger 866 may be caused by the operation of the drive 842.

The drive 842 may be similar in structure and operation to the mechanisms for moving a plunger along a cylinder as may be found in U.S. Pat. Nos. 6,656,158; 6,656,159; 7,128,727; and 7,144,384, which patents are incorporated by reference herein for all purposes. The drive 842 may include a plunger arm, a motor, a transmission and a power supply (e.g., a battery). The plunger arm may be in contact at least at a first end with the plunger 866 to urge the plunger 866 along the cylinder 860, and the transmission may be coupled to the plunger arm and the motor to cause the plunger arm to move according to the operation of the motor. The power supply provides a source of electrical power for the motor. The combination of the motor, transmission and power supply may also be referred to as one example of an actuator. Other mechanisms, such as springs, pressurized gases, materials undergoing phase changes and the like, may also be used to apply a force to the plunger to move the plunger along the cylinder.

According to other variants, a non-rigid collapsible pouch may be substituted for the rigid-walled cylinder 860 and the plunger 866 shown in FIG. 14. It will be recognized that where the reservoir 860 is in the form of a non-rigid collapsible pouch, a spring-based mechanical system may be used to compress and pressurize the reservoir. According to still further variants, a non-mechanical system may be used to move the plunger 866 or compress the bag. For example, a gas-generating system may be used, including a two-component system wherein the components are kept apart until the gas is to be generated, in which case they are combined. As a further alternative, a swellable gel may be used, wherein the introduction of water from a source internal to the device causes the gel to increase in dimension to move the plunger or compress the pouch. As a further example, a propellant reservoir may be opened and the propellant discharged to move the plunger 866 or compress the bag. Examples of such alternative mechanisms may be found in U.S. Pat. Nos. 5,957,895; 5,858,001; and 5,814,020, which patents are incorporated by reference herein for all purposes.

According to certain embodiments, the reservoir 840 may be a pre-filled container, such as a pre-filled cartridge or a pre-filled syringe. Alternatively, the delivery system 800 may include a fill port 880 in fluid communication with the reservoir 840, the fill port 880 adapted to receive a luer tip of a syringe (e.g., syringe illustrated in FIG. 13), although a rubber septum may be used instead, for example. In use, a healthcare provider may inject the drug from the syringe through the fill port 880 into the reservoir 840, and the syringe may be provided as a pre-filled syringe (filled with any of the materials mentioned above) to the healthcare provider with the delivery system 800 as a kit.

The cannula 844 may have a retracted state wherein a pointed end 890 (in fact, the entire cannula 844) may be withdrawn inside the housing 802 and a deployed state wherein the pointed end 890 projects from the housing 802, the inserter 846 moving the needle 844 from the retracted state to the deployed state. Examples of exemplary inserters may be found in U.S. Pat. Nos. 7,128,727 and 7,144,384, which patents are incorporated by reference herein for all purposes.

The cannula 844 may be hollow, and may be used to administer the drug directly to the patient. Alternatively, the structure 844 may be used in conjunction with a cannula 892, the structure 844 being used to insert the cannula 892 into the patient through the injection site, and the drug passing through the catheter 892 into the patient during administration. Phrased slightly differently, the system 800 may, according to certain exemplary embodiments, automatically insert a soft cannula into the subcutaneous tissue.

As illustrated in FIG. 14, the housing 802 (specifically the plate 804) may have an aperture or opening 894 formed therein to permit the cannula (or structure) 844 (and optionally cannula 892) to pass therethrough. According to certain embodiments, the aperture 894 may be unobstructed, such that there is no impediment or obstacle to the movement of the cannula 844 (and catheter 892) through the opening 894. However, to better maintain the sterility of the cannula 844 and the device's container closure integrity (CCI), a septum may be disposed in or over the aperture 894.

The septum, which may be made of a rubber, may be disposed between the cannula 844 (and the space 814) and the patient's skin with the needle 844 in the retracted state. In the deployed state, at least a portion of the needle 844 (i.e., the pointed end 890) will depend from the space 814 through the septum. As such, the septum is always present as a barrier between the interior space 814 and the external environment.

The system 800 may also include a controller 900, which may include at least one processor and memory, the processor programmed to carry out the actions that the controller is adapted to perform and the memory including one or more tangible non-transitory readable memories having executable instructions stored thereon, which instructions when executed by the at least one processor may cause the at least one processor to carry out the actions that the controller is adapted to perform. Alternatively, the controller may include other circuitry that carries out the actions that the controller is adapted to perform. By way of example and not by way of limitation, the controller 900 may be adapted to carry out any one of the methods described above relative to the drug delivery system.

In addition to the controller 900, the system 800 may include a communication module 902 and at least one sensor or switch. The communication module 902 may be any of a number of different communication modules used to communicate with the mobile device 110 and/or the computing device 114 (see FIG. 1). According to one embodiment, the communication module 902 may be a Bluetooth/Bluetooth Low Energy module that is coupled to the controller 900. The communication module 902 is used to transmit information from the system 800 to the mobile device 110 or computing device 114. Alternatively, other protocols may be used by the communication module 752, such as RFID, Zigbee, Wi-Fi, NFC, and others. According to the embodiment illustrated, the system 800 also includes a temperature sensor 904 on board the controller 900, and thus may carry out at least parts of the methods described in FIGS. 2 and 3A-3C.

The drug delivery system 800 may additionally include a valve 920 positioned along the fluid path between the reservoir 840 and the cannula 844. The valve 920 may be selectively opened and closed to, respectively, establish fluid communication between the reservoir 840 and the cannula 844 or prevent fluid communication between the reservoir 840 and the cannula 844. The valve 920 may be coupled to the controller 900, and opened or closed by the controller 900 based on the analysis of sensor data by the controller 900, for example. In some embodiments, the valve 920 may be a solenoid valve which can be opened or closed with an electrical signal. Any of the lockout steps described above may involve use of the controller 900 controller to close the valve 920 to prevent the discharge of medicament from the reservoir 840.

While a small fraction of the number of possible sensors or sensing systems have been mentioned above, further examples are provided below, grouped in accordance with the condition or operational states that may be determined using these sensors or sensing systems.

Condition State Information, Generally

Temperature may be determined using a temperature sensitive paper that changes color upon receipt of thermal energy, the paper used in conjunction with an optical sensor that can sense the color or a color change. Temperature also may be determined using a thermocouple, for example, with junctions against drug reservoir and external to device, the voltage across an in-line resistor being used to determine if the reservoir temperature or the ambient temperature is colder than that of the device and by how much. A reversible circuit may be used featuring a material such as nitinol that changes shape with temperature, the changing shape closing the circuit thereby activating a cumulative timer each time a temperature threshold is exceeded, the cumulative time used to ensure that the total time that the temperature exceeded a threshold temperature is below a predetermined threshold time period. A shape change material may also be used to actuate a flag or a shield so as to reveal a readiness indicator, such as may be read using an optical device.

Light exposure also may be determined using light sensitive paper that changes color with exposure to light, the paper used in conjunction with an optical device that can sense the color or a color change. Alternatively, a photoresistor with an associated voltage divider circuit may be used to sense the presence of light.

Orientation of the drug delivery system (and device) might be determined by using an accelerometer or a magnetometer. Additionally, the drug delivery system may use two-way communication with a computing device, such as the mobile device 110, to obtain orientation information from the mobile device 110 and thereby infer the orientation of the drug delivery device. In fact, the drug delivery system may be connected to a mobile device 110 to improve the strength of the inference that the orientation of the mobile device 110 corresponds to the orientation of the drug delivery device.

The color and/or turbidity of the product may be measured using an optical device, such as an optical transmitter/receiver pair, which pair may be disposed on the same side of the reservoir or on opposite sides of the reservoir. The measurement obtained using the optical device relative to the drug reservoir may be compared against a reference measurement. In fact, a reference may be provided within the drug device adjacent the drug reservoir such that the optical device may be used to optically inspect the drug in the reservoir and the reference, so that a comparison may be made between, for example, the measurement obtained relative to the drug product in the reservoir and relative to the reference. Alternatively, any gap in the reception of the light beam transmitted through the reservoir may indicate a cloudy product or one that has undergone a color change, as may the reception (or failure of reception) of a light beam that is deflected at a particular angle because of the presence of particulate matter in the product. Alternatively, a CCD array may be used to take a picture of the product in the reservoir, the picture being analyzed to determine color and/or turbidity, which analysis may be performed by the system or by a local device or a remote device (in which case the picture may be transmitted to the local or remote device for analysis).

Geographic position may be determined using Global Positioning Satellite transceivers. Additionally, the drug delivery system may use two-way communication with a computing device, such as the mobile device 110, to obtain geographic position information from the mobile device 110 and infer the position of the drug delivery device. In fact, the drug delivery system may be connected to a mobile device 110 to improve the strength of the inference that the position of the mobile device 110 corresponds to the position of the drug delivery device.

Temporal information may be obtained using a timer that is started at the time of manufacture, and which may be expiration date-calibrated. Alternatively, an RFID tag coded with manufacturing date may be included in package or with device, and queried by system prior to administration.

Operational State Information, Generally

The packaging may be used as a faraday cage, and the drug delivery system may include circuitry that detects interference with a signal or increased received signals as a consequence of the removal of the packaging so as to determine the operational state that the device is unpackaged.

A variety of sensors may be used to determine the operational state of application to patient. For example, back EMF through a coil from moving magnet on needle shield may indicate that the device has been applied to the patient.

Alternatively, displacement of component or assembly (such as the needle shield) because of application of the drug delivery device to the patient may open or close a switch/circuit to signal this operational state. Along similar lines, the movement of components or assemblies may be detected using an optical sensor, with the light beam between a transmitter and receiver being broken by a change in the position of components, such as the needle shield or the reservoir (e.g., syringe or cartridge), upon application of the drug delivery device to the patient. As a further alternative, a capacitive or resistive sensor may be used, as may a pressure sensor. In fact, information regarding cannula (or needle) insertion may be determined by measuring the resistance through the needle and/or skin relative to external contact. Changes in temperature at the end of the drug delivery device intended to abut the patient's skin may also be used to determine the operational state of application to the patient.

A similar set of sensors associated with the needle shield may be used to determine when the needle shield has been deployed and locked in place upon completion of drug delivery.

A similar set of sensors associated with the actuator or button (instead of the needle shield) may be used to determine when the actuator or button has been depressed to trigger delivery of the drug.

An accelerometer may be used to sense the shock impulse of an actuator being manipulated or the needle shield being moved to determine one of the operational states of triggering the device, initiating drug delivery and completing drug delivery. A pressure sensor may be mounted in the reservoir to detect an increase in pressure in the reservoir that would occur upon initiation of drug delivery so as to be used to determine this operational state. As a further alternative, a microphone or audio sensor may be used to determine if the mechanical noises from components indicate activation of the device. As a still further alternative, a strain sensor may be mounted on a thin column between drive mechanism and plunger that will flex under force to sense the operational state of triggering the drug device. In fact, according to certain embodiments the strain sensor may be limited to a single use (i.e., the sensor fails or permanently deforms under flex) to "save" the fact that delivery was triggered thus eliminating the need for high frequency signal monitoring.

ADDITIONAL EMBODIMENTS

Figure 16:
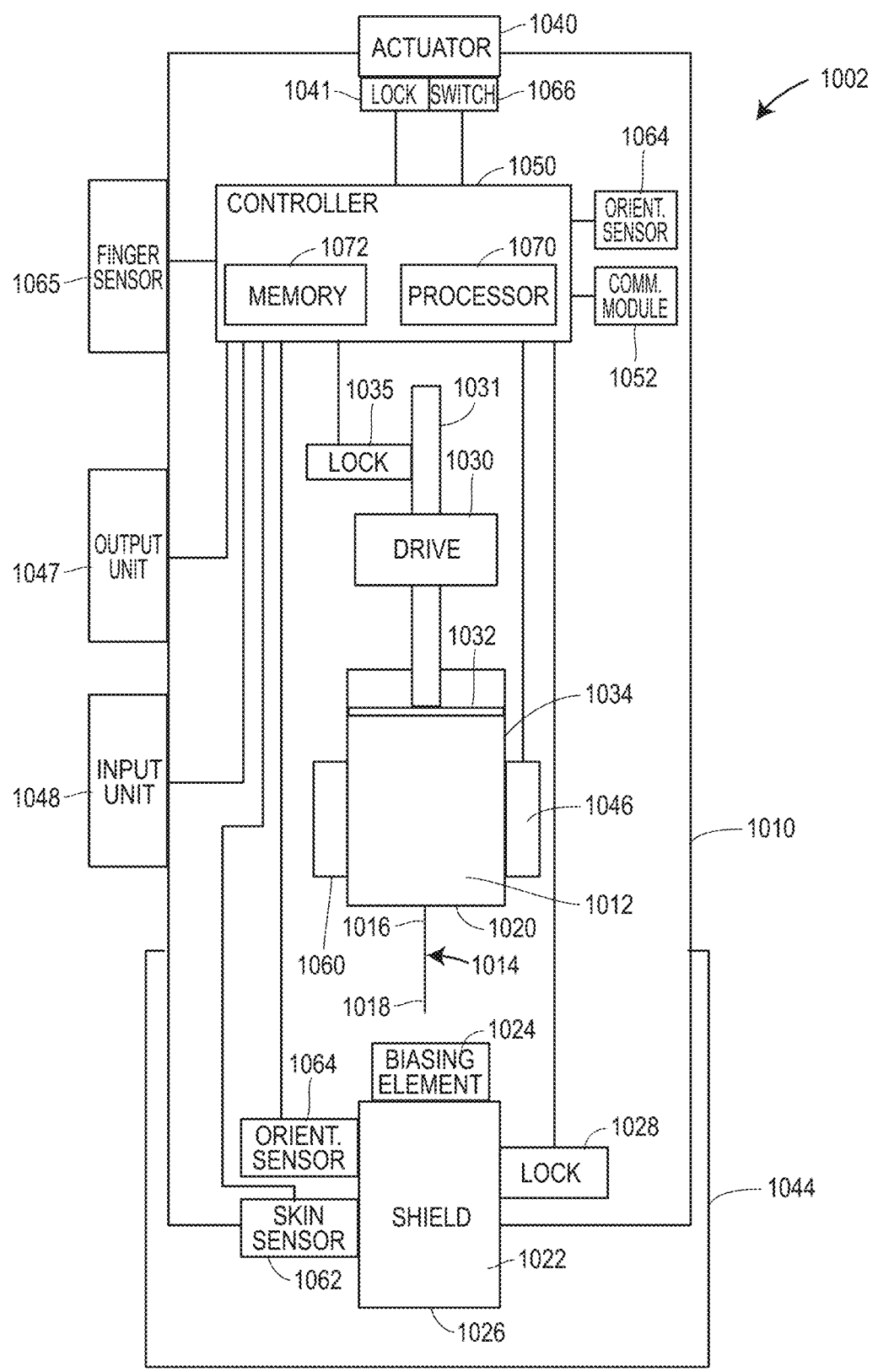
FIG. 16 is a schematic illustration of a drug delivery system including a drug delivery device, a controller, sensors, and controllable elements.
Figure 17:
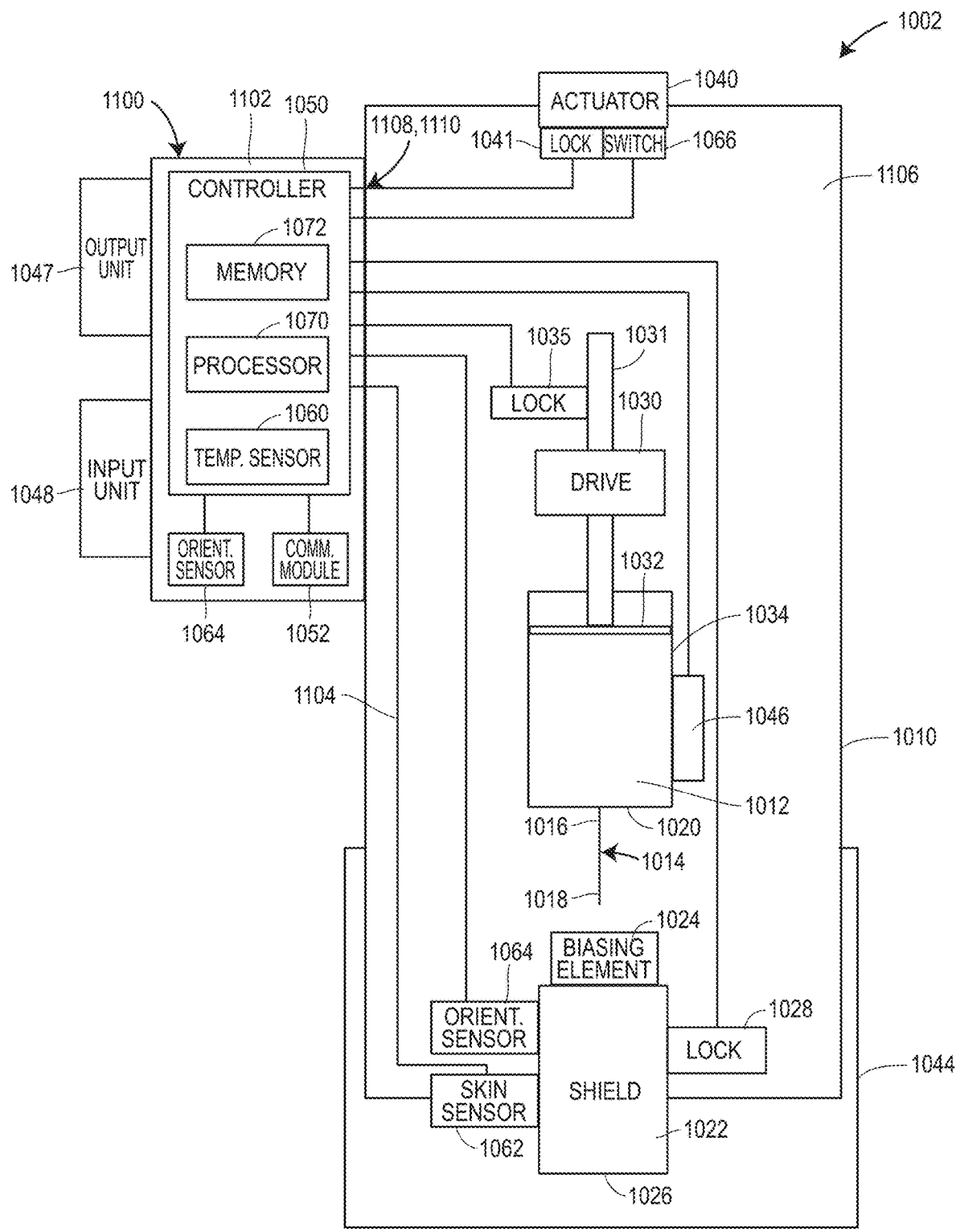
FIG. 17 is a schematic illustration of a drug delivery device with an attachable controller that may be used in the drug delivery system of FIG. 16.

FIGS. 16 and 17 illustrate additional embodiments of a drug delivery system that may be operated in accordance with one or more of the methods described above. The drug delivery system may sense or determine different types of information regarding a drug delivery device, including operational state information (e.g., whether medicament delivery is complete), condition information (e.g. temperature), and identity information (e.g., the name of the medicament). Based on this information, the drug delivery system may control the operation of one or more controllable elements (e.g., a lock, a heating element, a wake-up circuit, an output unit, etc.) of the drug delivery device.

While the sensors and controllable elements described below are configured for use in an autoinjector, one or more of the sensors and controllable elements may be configured for use with an on-body injector. Furthermore, any combination of the following sensors and controllable elements may be implemented in a single autoinjector or a single on-body injector, or any other drug delivery device. Additionally, one or more of the following sensors and/or controllable elements may be used in combination with one or more of the sensors and controllable elements described above in connection with FIGS. 1-15.

FIG. 16 illustrates an embodiment of a drug delivery system 1000 including a drug delivery device 1002. The drug delivery device 1002 may be in the form of an autoinjector, and thus is adapted for hand-held use and application against the skin of the patient. The drug delivery device 1002 includes a housing 1010 in which are disposed assemblies or structures that introduce a delivery cannula into the patient, and that eject a drug or medicament from a reservoir 1012 through the delivery cannula into the patient. According to certain embodiments, the same assemblies or structures that introduce the delivery cannula into the patient may also eject the drug or medicament from the reservoir through the delivery cannula into the patient. The drug delivery device 1002 may also include assemblies or structures that connect the delivery cannula to the reservoir, that withdraw the delivery cannula into the housing 1010 through an opening in the housing 1010 (not illustrated), or that deploy other structures that will prevent contact with the delivery cannula once the delivery cannula has been removed from the patient. Even additional assemblies and structures are possible. The specific embodiment of the drug delivery device 1002 discussed below is thus by way of example and not by way of limitation.

Accordingly, the drug delivery device 1002 includes a reservoir 1012 and a delivery cannula 1014 having a first end 1016 (e.g., a proximal end) that may be connected or connectable in fluid communication with the reservoir 1012 and a second end 1018 (e.g., a distal end) that may be inserted into a patient. The delivery cannula 1014 may be, for example, a rigid needle having a beveled edge that may be sized such that the second end 1018 of the needle 1014 is received under the skin so as to deliver a subcutaneous injection of the medicament within the reservoir 1012. The first end 1016 of the needle 1014 may be disposed through a wall 1020 of the reservoir 1012, and thus be connected in fluid communication with the reservoir 1012. Alternatively, the first end 1016 of the needle 1014 may be disposed only partially through the wall 1020 (which wall 1020 may be a resealable septum or stopper, for example) such that the first end of the needle 1014 may not be connected in fluid communication until the second end 1018 of the needle 1014 is inserted into the patient. In such a circumstance, the first end 1016 of the needle 1014 may thus be described as connectable in fluid communication with the reservoir 1012, although it will be recognized that there are other mechanisms by which the first end 1016 of the needle 1014 may be connectable, but not connected, in fluid communication with the reservoir 1012.

The drug delivery device 1002 includes a shield 1022 (e.g., a needle shield) that may be deployed at least after the injection has been completed to limit access to the second end 1018 of the needle 1014. According to certain embodiments, the shield 1022 may have a biasing element 1024 (such as a spring) that extends the shield 1022 from the housing 1010 such that a distal end 1026 of the shield 1022 extends beyond the second end 1018 of the needle 1014 except when the shield 1022 is disposed against the skin and the insertion of the needle 1014 is actuated. In fact, the insertion of the needle 1014 may be actuated according to certain embodiments of the drug delivery device 1002 by disposing the distal end 1026 of the shield 1022 on or against the skin of the patient.

The drug delivery device 1002 may also include a lock 1028 (e.g., a ratchet) that is coupled to the shield 1022 and configured to limit or prevent movement of the shield 1022 relative to the housing 1010 of the drug delivery device 1002 such that the distal end 1026 of the shield 1022 extends from the housing 1010 a sufficient distance to limit or prevent contact with the second end 1018 of the needle 1014, for example, after the needle 1014 has been removed or separated from the skin of the patient. In some embodiments, the lock 1028 may be coupled to a controller (e.g., controller 1050 described in more detail below) which can selectively activate or deactivate the lock 1028 based on different types of information regarding the drug delivery device 1002, including operational state information, condition information, and/or identity information, in accordance with one or more of the methods described above. When the lock 1028 is activated by the controller 1050, the lock 1028 may be configured to limit or prevent movement of the needle shield 1022 relative to the housing 1010. When the lock 1028 is deactivated by the controller 1050, the lock 1028 may be configured to allow movement of the needle shield 1022 relative to the housing 1010.

The drug delivery device 1002 also includes at least one drive 1030 that may be used to insert the second end 1018 of the needle 1014 into the skin of the patient, and to eject the drug or medicament from the reservoir 1012 through the delivery cannula 1014 into the patient. The drive 1030 may include one or more springs, according to certain embodiments. According to other embodiments, the drive 1030 may include a source of pressurized gas or a source of a material that undergoes a phase change, such that the escaping gas or phase changing material provides a motive force that may be applied to the reservoir 1012 to eject the drug therefrom. According to still other embodiments, the drive 1030 may include an electromechanical system, such as may include a motor for example, although such an electromechanical system may be more appropriate for the on-body autoinjector or infuser described above. Other embodiments of the drive 1030 are also possible.

In one embodiment, the drive 1030 may be coupled to a plunger 1031 and/or a stopper 1032 (e.g., a wall) disposed in the reservoir 1012 to move that stopper 1032 in a distal direction toward the delivery cannula 1014. In accordance with such an embodiment, the stopper 1032 may be a stopper that is fixed to a distal end of the plunger 1031 and received within a bore 1034. The plunger 1031, in conjunction with the drive 1030, may move the stopper 1032 along a longitudinal axis of the drug delivery device 1002 through the bore 1034 from a proximal end of the bore 1034 to a distal end of the bore 1034, and thereby eject the medicament from the reservoir 1012.

In some embodiments, the drive 1030 may also cooperate with the stopper 1032 and/or the bore 1034 to move the reservoir 1012 relative to the housing 1010 so as to move the second end 1018 of the needle 1014 relative to the housing 1010 and into the patient. According to those embodiments wherein the drive 1030 cooperates with the stopper 1032, this may occur before the first end 1016 of the needle 1014 is in fluid communication with the reservoir 1012. According to those embodiments wherein the drive cooperates with the bore 1034, the drive may include one component (e.g., first spring) that cooperates with the bore 1034 to move the reservoir 1012 and needle 1014 relative to the housing 1010, and a second component (e.g., second spring) that cooperates with the stopper 1032 to move the stopper 1032 relative to the bore 1034.

The drug delivery device 1002 may also include a lock 1035 that is coupled to the plunger 1031 and configured to limit or prevent movement of the plunger 1031 relative to the housing 1010 of the drug delivery device 1002 so that the stopper 1032 cannot be advanced to discharge the medicament from the reservoir 1012 to the patient. In some embodiments, the lock 1035 may be coupled to a controller (e.g., controller 1050 described in more detail below) which can selectively activate or deactivate the lock 1035 based on different types of information regarding the drug delivery device 1002, including operational state information, condition information, and/or identity information, in accordance with one or more of the methods described above. When the lock 1035 is activated by the controller 1050, the lock 1035 may be configured to limit or prevent movement of the plunger 1031 relative to the housing 1010. When the lock 1035 is deactivated by the controller 1050, the lock 1028 may be configured to allow movement of the plunger 1031 relative to the housing 1010. In some embodiments, the lock 1035 may include a pin member (not illustrated in FIG. 16) selectively engageable with one or more teeth or notches (not illustrated in FIG. 16) arranged along the length of the plunger 1031. The pin member may be moved into and/or out of engagement with the one or more teeth or notches by a motor controlled by the controller 1050. The drive 1030 may be associated with an actuator 1040. The actuator 1040 may activate the drive 1030 to cause the drive 1030 to insert the needle 1014 and eject the drug from the reservoir 1012 through the needle 1014 into the patient. The actuator 1040 may, according to certain embodiments, be the needle shield 1022, as explained above. According to other embodiments, such as the one illustrated in FIG. 16, the actuator 1040 may be a button that may be manually depressed by the user or patient once the drug delivery device 1002 is placed disposed on or against the patient's skin. A lock 1041 may be coupled to the actuator 1040 and configured to limit or prevent movement of the actuator 1040 so that the actuator 1040 cannot be used to activate the drive 1030. In some embodiments, the lock 1041 may be coupled to a controller (e.g., controller 1050 described in more detail below) which can selectively activate or deactivate the lock 1041 based on different types of information regarding the drug delivery device 1002, including operational state information, condition information, and/or identity information, in accordance with one or more of the methods described above. When the lock 1041 is activated by the controller 1050, the lock 1041 may be configured to limit or prevent movement of the actuator 1040 relative to the housing 1010. When the lock 1041 is deactivated by the controller 1050, the lock 1041 may be configured to allow movement of the actuator 1040 relative to the housing 1010. In alternative embodiments, the lock 1041 may be configured to prevent the actuator 1040 from triggering the drug delivery device 1002 without necessarily preventing movement of the actuator 1040. In such alternative embodiments, the lock 1041 may be an electrical switch configured to selectively open and close an electrical circuit connecting the lock 1040 to the controller 1050. Alternatively, the lock 1041 may be a software module stored in the memory 1072 which, upon execution by the controller 1050, prevents a trigger signal from the actuator 1040 from activating the drug delivery device 1002 to deliver a medicament to the patient.

The drug delivery device 1002 may also include a removable sterile barrier 1044 that is disposed about one or more of a distal end of the housing 1010, the needle shield 1022, and the second end 1018 of the delivery cannula 1014. The removable sterile barrier 1044 may be removably attached to the distal end of the housing 1010 as shown in FIG. 16. In some embodiments, the removable sterile barrier 1044 may form an interference or snap fit with the distal end of the housing 1010. A frictional force associated with the interference or snap fit may be overcome by manually pulling the removable sterile barrier 1044 in a direction away from a housing 1010. The removable sterile barrier 1044, when attached to the drug delivery device 1002, may reduce the risk of contamination of the delivery cannula 1014 and other elements disposed within the drug delivery device 1002.

Additionally, the drug delivery device 1002 may include a heating element 1046 coupled to the exterior of the reservoir 1012 and configured to warm the medicament inside the reservoir 1012 through, for example, conductive heating. The heating element 1046 may be coupled to the controller 1050 so that the controller 1050 can selectively activate or deactivate the heating element 1046 based on different types of information regarding the drug delivery device 1002, including operational state information, condition information, and/or identity information, in accordance with one or more of the methods described above. In some embodiments, the heating element 1046 may include an electrically conductive coil that is wrapped around the exterior of the reservoir 1012. Alternatively, or additionally, a cooling element (not illustrated) may be coupled to the reservoir 1012 and controllable by the controller 1050 in a manner similar to the heating element 1046.

The drug delivery device 1002 may also include an output unit 1047 coupled to the housing 1010 and configured to notify the patient or user of information related to the drug delivery device 1002. The output unit 1047 may be coupled to the controller 1050 so that the controller 1050 can selectively activate or deactivate the output unit 1047 based on different types of information regarding the drug delivery device 1002, including operational state information, condition information, and/or identity information, in accordance with one or more of the methods described above. The output unit 1047 may be any device suitable for conveying information to the patient or user including a display (e.g., a liquid crystal display), a touchscreen, a light (e.g., a light emitting diode), a vibrator (e.g., an electro-mechanical vibrating element), a speaker, and/or an alarm, among other devices.

The drug delivery device 1002 may also include an input unit 1048 coupled to the housing 1010 and configured to allow a user or patient to input information (e.g., password information) to be used by the controller 1050. In some embodiments, the input unit 1048, the output unit 1047, and even the fingerprint sensor 1065, may be a single device such as a touchscreen. In other embodiments, the input unit 1048 may be a separate device from the output unit 1047 such as a keyboard or button.

As illustrated in FIG. 16, the reservoir 1012, the biasing element 1024, the locks 1028, 1035, 1041, the plunger 1031, the stopper 1032, and the drive 1030, and the heating element 1046 are disposed within the housing 1010, along with at least part of the delivery cannula 1014. Also disposed within the housing 1010 is a controller 1050, a communication module 1052 (e.g., a wireless transmitter), and at least one sensor or switch. According to the embodiment illustrated in FIG. 16, four sensors are included: a temperature sensor 1060, a skin sensor 1062, at least one orientation sensor 1064, and a fingerprint sensor 1065. In addition, a switch 1066 is also provided. The controller 1050 is coupled to the communication module 1052, the locks 1028, 1035, 1041, the sensors 1060, 1062, 1064, 1065, the heating element 1046, the fingerprint sensor 1065, the output unit 104, the input unit 1048, and the switch 1066. The controller 1050, the communication module 1052, one or more of the sensors 1060, 1062, 1064, 1065 and the switch 1066 may be packaged together as a single module, or each component may be fabricated separately and coupled once the components are disposed within the housing 1010. According to certain embodiments, each electrical component may be integrated into the structure of the device 1002 associated with that electrical component (e.g., the sensors 1062 and 1064 may be integrated into the shield 1022). In some embodiments, the controller 1050, the communication module 1052, one or more of the sensors 1060, 1062, 1064, 1065, and/or the switch 1066 may be packaged together inside the removable sterile barrier 1044.

The controller 1050 may include at least one processor 1070 (e.g., a microprocessor) and memory 1072. The controller 1050 may also include or be coupled to a power supply, e.g. a battery. The processor 1070 may be programmed to carry out the actions that the controller 1050 is adapted to perform and the memory 1072 may include one or more tangible non-transitory readable memories having executable instructions stored thereon, which instructions when executed by the at least one processor 1070 may cause the at least one processor 1070 to carry out the actions that the controller 1050 is adapted to perform. Alternatively, the controller 1050 may include other circuitry that carries out the actions that the controller is adapted to perform.

The memory 1072 may store the identity information discussed above. The identity information may be stored in the memory 1072 prior to the start of execution of any of the methods discussed above. The identity information may include, by way of example and not by way of limitation, a unique identifier, the name of the drug, the dosage, an expiration date, and information regarding the identity of the patient for whom the drug was prescribed. With this information, the controller 1050 or a local device (e.g., a smartphone) may make a determination regarding the patient that is about to receive the drug, and provide appropriate informational and/or instructional prompts. As an alternative to memory 1072, the identity information may be contained in a QR code label or RFID tag associated with the drug delivery device 1002.

The communication module 1052 may be any of a number of different communication modules used to communicate with a local device (e.g., a smartphone) and/or a remote device (e.g., a server operated by the device manufacturer). According to one embodiment, the communication module 1052 may be a Bluetooth/Bluetooth Low Energy module that is on-board with the controller 1050. The communication module 1052 is used to transmit information from the drug delivery device 1002 to the local device. Alternatively, other wireless protocols may be used by the communication module 1052, such as RFID, Zigbee, Wi-Fi, NFC, and others. In fact, the communication may be sent along a hardwired connection, rather than using the electromagnetic (EM) spectrum. As defined herein, a communication transmitted and/or received between the module 1052, the local device, and/or the remote device may be in the form of a hardwired signal or EM signal or a pattern of such signals, for example.

The temperature sensor 1060 may be disposed proximate to the reservoir 1012 so that the temperature of the drug in the reservoir 1012 may be determined. Alternatively, the temperature sensor 1060 may simply be disposed in the housing 1010, so that an approximate temperature of the drug in the reservoir 1012 and of the drug delivery device 1002 generally may be determined. According to an embodiment, the temperature sensor 1060 may be an on-board temperature sensor 1060 attached to the processor 1070.

The skin sensor 1062 may be attached to or associated with the shield 1022 to determine when the drug delivery device 1002 is disposed on or against the patient's skin. According to one embodiment, the skin sensor 1062 is a pressure sensor. According to other embodiments, the skin sensor 1062 may be a capacitance sensor, resistance sensor, or inductance sensor. The skin sensor 1062 or the switch 1066 (which is attached to or associated with the actuator 1040) may be used to determine when the drug delivery device 1002 is activated or actuated, depending on the design and operation of the drug delivery device 1002 that is used to actuate the drive 1030, in accordance with the discussion above. It may also be the case that a signal from the skin sensor 1060 is used to determine that the drug delivery device 1002 has been activated even when the shield 1022 is not used as the actual actuator, the underlying assumption being that the movement of the shield 1022 is necessarily related to the actuation of the device 1002.

The orientation sensors 1064, of which there may be at least two as illustrated, may be associated with the shield 1022 (or that portion of the housing 1010 adjacent the shield 1022) and the controller 1050 (which may be, as illustrated, disposed at the other end of the drug delivery device 1002 or the housing 1010 from the shield 1022). The orientation sensors 1064 may be magnetometers, for example. In particular, the orientation sensor 1064 associated with the controller 1050 may be an on-board magnetometer. The orientation sensors 1064 may be used to determine the orientation of the drug delivery device 1002 (in particular, the housing 1010) relative to the injection site (or more particularly, relative to the placement of the drug delivery device 1002 on or against the patient's skin)

It will be recognized that the arrangement of the components of the drug delivery device 1002 within the housing 1010 is but one embodiment of this disclosure. For example, FIG. 17 illustrates a second embodiment of the drug delivery device 1002, wherein certain components of the drug delivery device 1002 are disposed outside the drug delivery device 1002.

According to this embodiment, the drug delivery device 1002 may include the housing 1010, the reservoir 1012, the needle 1014, the shield 1022, the biasing element 1024, the lock 1028, the drive 1030, and the button 1040. Furthermore, the sensors 1062, 1064 and the switch 1066 may be disposed within the housing 1010. A separate module 1100 is provided within a housing 1102 in which the controller 1050, communication module 1052, and on-board temperature and orientation sensors 1060, 1064 are disposed. The fingerprint sensor 1065, the output unit 1047, and the input unit 1048 may be disposed on the exterior of the module 1100 so that a user or patient can interact with them. In some embodiments, the communication module 1052 may be disposed within the housing 1010 rather than within the module 1100.

The module 1100 may be adapted to be attached to an exterior surface 1104 of the housing 1010; for example the module 1100 may have an annular or C-shape with a central aperture sized so that an end 1106 of the drug delivery device 1002 may be disposed within the aperture, and the module 1100 held in place by the mating geometries. According to certain embodiments, the module 1100 may be moveable relative to the drug delivery device 1002, such that movement of the module 1100 relative to the housing 1010 may activate the autoinjector (e.g., by depressing the button 1040), in which case the switch 1066 may actually be disposed within the housing 1102 of the module 1100. According to other embodiments, the exterior surface 1104 of the housing 1010 and the module 1100 may have cooperating connectors. As a further alternative, a fastener may be provided on the housing 1010 or the module 1100 that cooperates with a feature of the other of the housing 1010 or the module 1100 to attach or secure the module 1100 to the housing 1010, whether reversibly or irreversibly. One example of such a fastener may be a set screw on the module 1100 that cooperates with a recess on the surface 1104 of the housing 1010.

The exterior surface 1104 of the housing 1010 may also have one or more contacts 1108 that mate with contacts 1110 on an exterior surface 1112 of the housing 1102 of the module 1100. The mating contacts 1108, 1110 couple the sensors 1062, 1064, the locks 1028, 1035, 1041, the heating element 1046, and the switch 1066 inside the drug delivery device 1002 with the controller 1050 inside the module 1100 (i.e., the sensors 1062, 1064, the locks 1028, 1035, 1041, the heating element 1046, and the switch 1066 are coupleable with the controller 1050, as may be the communication module 1052 according to the certain embodiments described above wherein the module 1052 is disposed in the housing 1010 as well). The contacts 1108, 1110 may contact each other, or the contacts may mate without having to physically contact each other, in which case the contacts 1108, 1110 may be provided below the surfaces 1104, 1112 of the housings 1010, 1102.

The separation of the controller 1050, communication module 1052 and other components into a module 1100 may permit the module 1100 to be used with multiple instances of the drug delivery device 1002. In this regard, the module 1100 may be considered to be the reusable portion of the drug delivery device 1002/module 1100 combination (which may be referred to as the drug delivery device 1002 for purposes of this disclosure), while the drug delivery device 1002 may be considered to be the disposable portion of the drug delivery device 1002. By isolating the more expensive components into the reusable module 1100 and the less expensive components (including certain sensors) into the disposable drug delivery device 1002, the overall cost of the autoinjector may be optimized. This arrangement of the components in the module 1100 and the drug delivery device 1002 may also facilitate the manufacture and sterilization of the drug delivery device 1002 and module 1100.

Figure 18A:
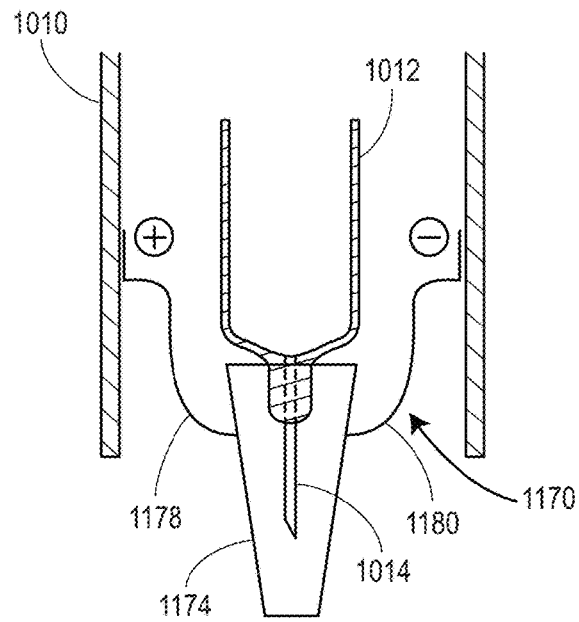
FIG. 18A is a cross-sectional view of an embodiment of a heating element configured to heat a delivery cannula of a drug delivery device prior to removal of a removable sterile barrier.
Figure 18B:
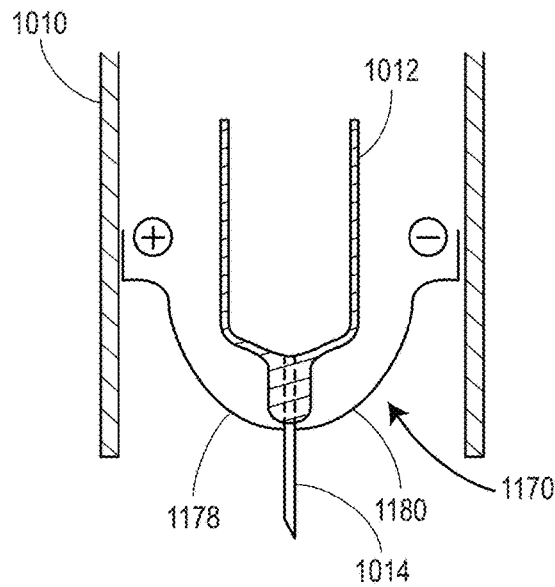
FIG. 18B is a cross-sectional view of the embodiment of FIG. 19A after removal of the removable sterile barrier.

While the heating element 1046 of the drug delivery device 1002 is coupled to the reservoir 1012, in other embodiments, the heating element may be coupled, directly or indirectly, to the cannula 1014. Heating the cannula 1014 as opposed to the reservoir 1012 may be a more efficient manner of heating the medicament because less heat may be lost to the surroundings. FIGS. 18A and 18B illustrate an embodiment of a heating element 1150 configured to contact and heat the cannula 1014 upon removal of a removable sterile barrier 1174 from the cannula 1014. The heating element 1170 may include a first electrically conductive spring arm 1178 and a second electrically conductive spring arm 1180. Prior to removal of the removable sterile barrier 1174 from the cannula 1014, the first and second electrically conductive spring arms 1178, 1180 may be biased against the exterior of the removable sterile barrier 1174, as illustrated in FIG. 18A. Configuring the heating element 1170 so that it does not contact the cannula 1014 prior to use may help preserve the sterility of the cannula 1014. Upon removal of the removable sterile barrier 1174 from the cannula 1014, the first and second electrically conductive spring arms 1178, 1180 return to their relaxed position by pivoting towards the cannula 1014, until each of them contacts the cannula 1014 (see FIG. 18B). In this configuration, the cannula 1014, which may be made of a metallic, electrically conductive material, may provide an electrical connection between the first and second electrically conductive spring arms 1178, 1180, thereby forming a closed electrical circuit. In some embodiments, the controller 1050 may selectively activate or deactivate the heating element 1170 based on different types of information regarding the drug delivery device 1002, including operational state information, condition information, and/or identity information, in accordance with one or more of the methods described above. For example, the controller 1050, which may be coupled to each of the first and second electrically conductive spring arms 1178, 1180, may control the amount of electricity supplied to the heating element 1014 based on the delivery speed of the medicament to the patient. Direct heating of the cannula 1014 may enable more precise control of the viscosity of the medicament, and thus more precise control of the flow rate of the medicament.

The heating element 1170 may be particularly useful in a drug delivery device that uses a spring to drive its plunger. A spring typically provides a constant force, thereby making it difficult, if not impossible, to vary the flow rate of the medicament with a spring. The heating element 1170, by virtue of its ability to alter the viscosity of the medicament, may help overcome the limitations of the spring by providing relatively precise control over the medicament flow rate. In some embodiments, the actual medicament flow rate may be monitored with a sensor, and depending on how close the actual medicament flow rate is to a target medicament flow rate, the heating element 1170 may be controlled to heat the medicament flowing through the delivery cannula 1014 (or allow passive cooling the medicament flowing through the delivery cannula 1014), thereby increasing (or decreasing) the medicament flow rate. Accordingly, the medicament flow rate may be controlled without using any electrically actuated moving parts. Furthermore, in some embodiments, the heating element 1170 may include a Peltier effect circuit for heating and/or cooling the medicament in the delivery cannula 1014.

Other variants of the heating element that directly or indirectly heat the cannula 1014 are envisioned by this disclosure, including a heating element comprised of a coil that is wrapped around the cannula 1014 and/or embedded in a septum of the reservoir 1012. In still further embodiments, the heating element may be a laser or other energy source capable of focusing energy on the cannula 1014 from a distance.

Figure 19:
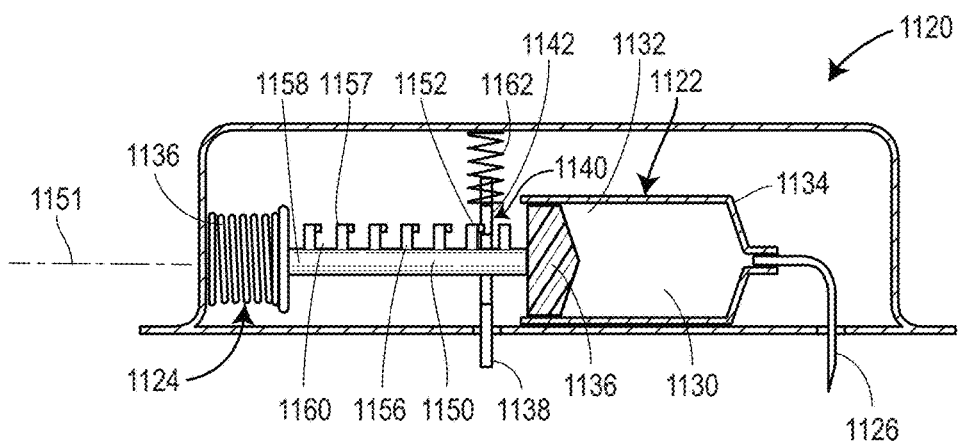
FIG. 19 is a cross-sectional view of an embodiment of a drug delivery device including a mechanically-actuated lock.

While the lock 1035 of the drug delivery device 1002 is activated and deactivated by the controller 1050, the scope of the present disclosure is not limited to electronically controlled locks. FIG. 19 illustrates a drug delivery device 1120 including a reservoir 1122, a plunger assembly 1124, a cannula 1126, a drive 1128, and a mechanically-actuated lock 1140 for limiting movement of the plunger assembly 1124 or the drive 1128. Though not illustrated in FIG. 19, the drug delivery device 1120 may include some or all of the electronic components of the drug delivery devices described above (and below) including, for example, the controller, communication module, input unit, output unit, skin sensor, orientation sensor, fluid level sensor, and/or heating element.

Referring to FIG. 19, the reservoir 1122 includes a bore 1130 having a first end 1132 and a second end 1134. The plunger assembly 1124 includes a plunger 1136 moveable within the bore 1130 of the reservoir 1122 between the first and second ends 1132, 1134. The cannula 1126 includes an operational state wherein the cannula 1126 is connected in fluid communication with the reservoir 1122. The drive 1128, in the form of a spring, is coupled to the plunger assembly 1124 to move the plunger 1136 between the first and second ends 1132, 1134. The lock 1140 may be selectively coupled to one of the plunger assembly 1124 and the drive 1128 to limit movement of the plunger 1136 between the first and second ends 1132, 1134 of the bore 1130. For example, the lock 1140 may be coupled to the one of the plunger assembly 1124 and the drive 1128.

As depicted in FIG. 19, the drug delivery device 1002 may include a proximity sensor 1138 coupled to the lock 1140 and moveable relative to a housing 1139 in which the reservoir 1122, drive 1128, and lock 1140 are disposed. The proximity sensor 1138 has a first sensor state (or position) wherein the proximity sensor 1138 extends (e.g., extends fully) from the housing 1139 and a second sensor state (or position) wherein the proximity sensor 1138 is retracted toward and into the housing 1139 relative to the first sensor state. The lock 1140 is coupled to the one of the plunger assembly 1124 and the drive 1128 with the proximity sensor 1138 in the first sensor state so as to limit or prevent movement of the plunger 1136.

Still referring to FIG. 19, the plunger assembly 1124 may include a plunger arm 1150 attached to the plunger 1136. The lock 1140 may have a wall 1142 that abuts the plunger arm 1150 to limit movement of the plunger 1136 when the lock 110 is coupled to the plunger assembly 1124. The proximity sensor 1138 is coupled to the wall 1142 (as illustrated, the sensor 1138 is integral, or one piece, with the wall 1142), such that the wall 1142 abuts the plunger arm 1150 with the proximity sensor 1138 in the first sensor state and such that the wall 1142 is spaced from the plunger arm 1150 with the proximity sensor 1138 in the second sensor state. In some embodiments, the plunger arm 1150 may have at least one shoulder 1152 formed thereon, and the wall 1142 abuts the at least one shoulder 1152 of the plunger arm 1150 to limit and/or prevent movement of the plunger 1136 when the lock 1140 is coupled to the plunger assembly 1124. As illustrated in FIG. 19, the plunger arm 1150 has a section of its length (i.e., a dimension of the plunger arm 1150 extending in a direction along a longitudinal axis 1151 of the plunger arm 1150) that has at least one feature 1156 that defines the at least one shoulder 1152. For example, the plunger arm 1150 may include a shaft 1158 to which is attached one or more features 1156 that include protrusions 1157 (e.g., teeth). In some embodiments, the protrusions 1157 can be formed integrally (as one piece) with the shaft 1158. Spaces or notches 1160 between adjacent protrusions 1157 permit the wall 1142 to be disposed between adjacent protrusions 1157 with the protrusion 1158 positioned furthest longitudinally from the plunger 1136 defining the shoulder 1152 along a surface of the protrusion 1158 that extends perpendicularly to the axis 1151.

When the drug delivery device 1002 is not disposed on the surface of the patient's skin, the proximity sensor 1138 extends from the housing 1139 as a consequence of the force applied to the lock 1140 by a spring 1162. In turn, the lock 1140 is positioned relative to the plunger assembly 1124, and in particular the plunger arm 1150, such that the lock 1140 resides within one of the spaces or notches 1160. When the drug delivery device 1002 is disposed on the surface of the patient's skin, the proximity sensor 1138 is moved into the housing 1139 against the bias of the spring 1162. As a consequence, the lock 1140 is moved into a position where an aperture in the lock 1140 is aligned with the plunger arm 1150, such that the lock 1140 no longer resides within one of the spaces or notches 1160. This permits movement of the plunger arm 1150 and associated plunger 1136 as a consequence of the force applied to the plunger arm 1150 by the spring 1162.

During the motion of the plunger arm 1150 toward the right relative to the orientation of FIG. 19, the drug delivery device 1002 may become detached or displaced from the patient's skin. In such a case, the lock 1140 would be permitted to move under bias of the spring 1162 such that the aperture in the lock 1140 is no longer aligned with the plunger arm 1150, and instead the lock 1140 becomes disposed within one of the spaces or notches 1160. This can cause engagement between the lock 1140 and one of the protrusions 1157 that would prevent further motion of the plunger arm 1150 at the urging of the spring 1162, and would limit the amount of medical fluid or drug product ejected from the reservoir 1122. That is, according to certain embodiments, engagement between the lock 1140 and a protrusion 1157 may prevent any further medicament from passing through and out of the cannula 1126. According to other embodiments, the plunger arm 1150 and associated plunger 1136 may travel some distance after the plate 158 becomes disposed within a space or notch 1160 but before the lock 1140 engages a protrusion 1157, such that a limited amount of medicament may pass out of the reservoir 1122 through the cannula 1126 even after activation of the lock 1140. It will be recognized that by limiting the amount of medical fluid or drug product ejected from the reservoir 1122, while arresting the overall motion of the plunger 1136, significant advantages may still be obtained.

While the foregoing drug delivery systems and methods utilize controllable elements to automate various aspects of their operation and reduce the likelihood of improper use by patients, the drug delivery systems and methods of the present disclosure may incorporate additional or alternative features to improve their usability, particularly for patients who might have difficulty gripping or handling a drug delivery device, such as elderly and disabled patients. Described below with reference to FIGS. 18 and 19 is a removable sterile barrier that, in addition to inhibiting the contamination of an interior of a drug delivery device, provides an anti-roll functionality, helps patients grip and detach the removable sterile barrier from the drug delivery device, and optionally houses various electronic components including, for example, a controller, a memory, one or more sensors, and/or a communication module.

Figure 20:
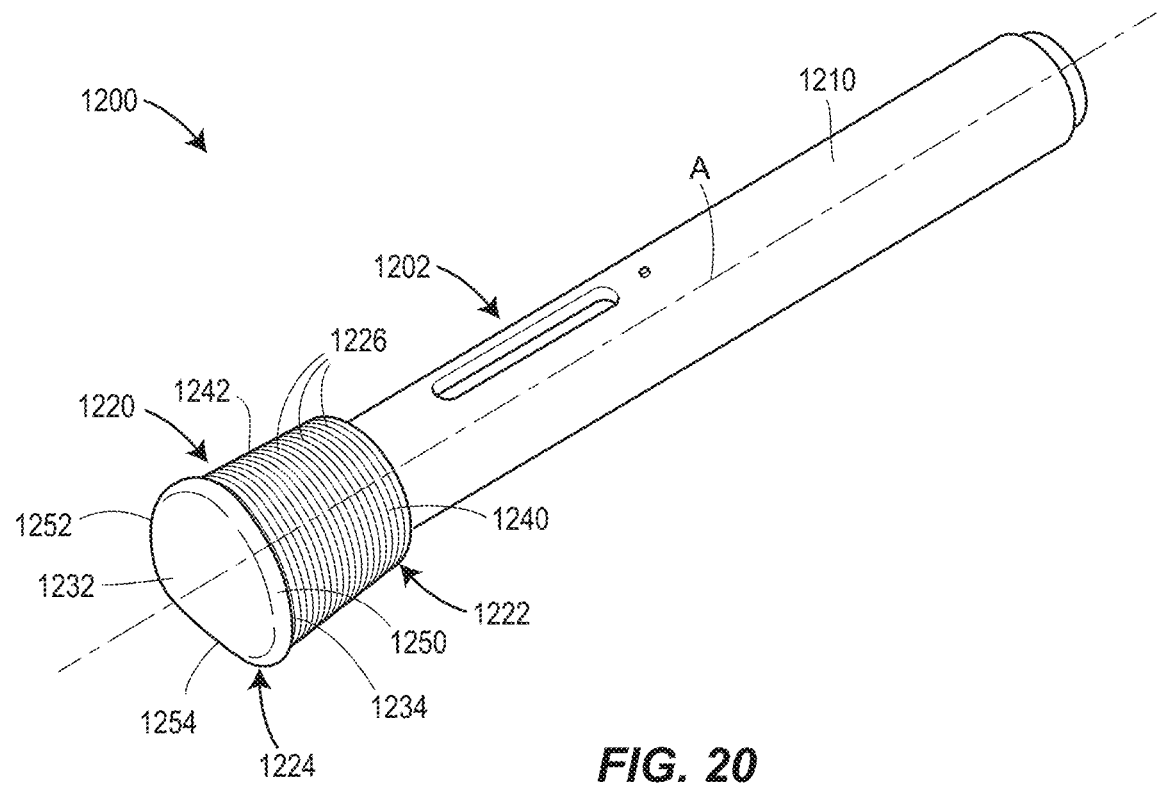
FIG. 20 is a perspective view of a drug delivery system according to a further embodiment of the disclosure including an anti-roll removable sterile barrier.

In particular, as illustrated in FIG. 20, a drug delivery system 1200 is provided that includes a drug delivery device 1202. The drug delivery device 1202 may be in the form of an autoinjector, and thus configured for hand-held use and application against the skin of the patient. The drug delivery device 1202 may include some or all of the same components as the drug delivery device 1002 described above in connection with FIG. 16. The drug delivery device 1202 may include a housing 1210 in which are disposed assemblies or structures that introduce a delivery cannula into a patient and that eject a drug or medicament from a reservoir through the delivery cannula into the patient. The drug delivery device 1202 may also include an actuator 1212, similar to the actuator 1040, disposed at a proximal end of the housing 1210 and configured to be depressed by the patient to activate a drive to that causes a plunger to discharge the medicament from the reservoir through the delivery cannula into the patient.

The drug delivery device 1202 may further include a removable sterile barrier 1220 removably attached to a distal end of the housing 1210. The removable sterile barrier 1220 reduces the risk of contamination of the delivery cannula and other elements within the housing 1210 prior to use of the drug delivery device 1202. The removable sterile barrier 1220 may be formed by a tubular member 1222 and a cover member 1224 that covers an open end of the tubular member 1222. The tubular member 1222 and the cover member 1224 may be integrally formed as a single unitary structure, or alternatively, formed as separate components which are adhered or mechanically interconnected to each other.

Figure 21:
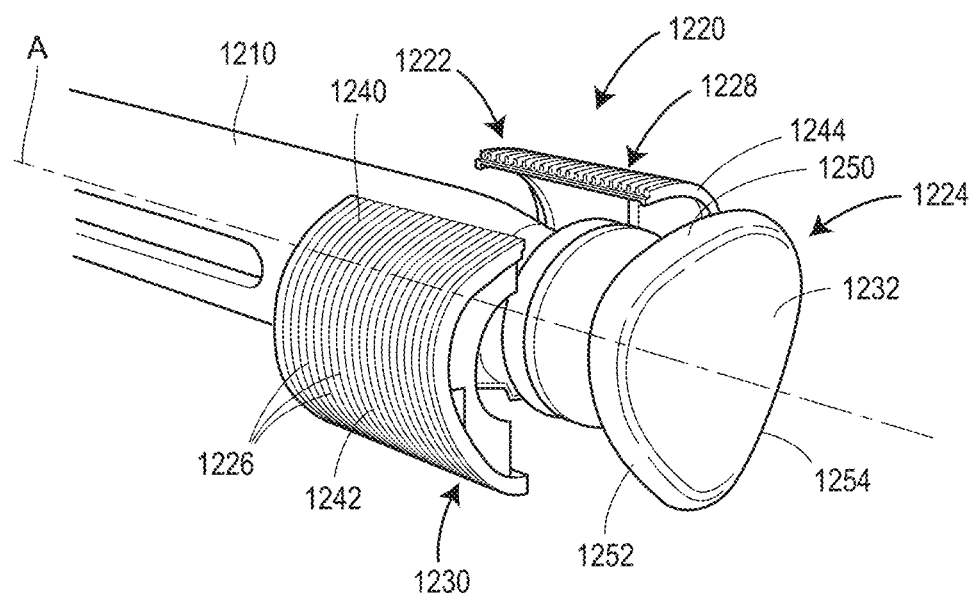
FIG. 21 is an assembly view of the anti-roll removable sterile barrier of FIG. 20.

The tubular member 1222 may be disposed about (e.g., surround) the distal end of the housing 1210 and/or a distal end of a delivery cannula (not illustrated), and may removably attach the removable sterile barrier 1220 to the housing 1210. As shown in FIG. 21, the tubular member 1222 may be assembled by fitting two interlocking and generally C-shaped members 1228, 1230 over the distal end of the housing 1210. In some embodiments, the removable sterile barrier 1220 may form an interference or snap fit with the distal end of the housing 1210. A frictional force associated with the interference or snap fit may be overcome by manually pulling the removable sterile barrier 1220 in a distal direction away from a housing 1210. The interference or snap fit may be formed by configuring an inner diameter of the tubular member 1222 to be slightly smaller than an outer diameter of a distal end of the housing 1210. Alternatively, or additionally, the tubular member 1222 may have a tearable or weakened member (not illustrated) that connects the tubular member 1222 to the distal end of the housing 1210 and which can be broken or torn by the patient when pulling the removable sterile barrier 1220 away from the housing 1210. The tubular member 1222 may further include a plurality of outwardly protruding ribs 1226 designed to help a patient grip the tubular member 1222 to detach it from the housing 1210. The ribs 1226 may be useful to elderly and disabled patients who have below average gripping strength.

The cover member 1224 may be fixed to a distal end of the tubular member 1222 and may completely cover an opening formed at the distal end of the tubular member 1222. A distal end surface 1232 of the cover member 1224 may be planar such that the drug delivery device 1202 can be disposed on planar surface in an upright configuration without falling over. Also, an outer peripheral portion of the cover member 1224 may be wider than an outer peripheral portion of the tubular member 1222 such that a ledge or overhang 1234 is formed at the interface between the cover member 1224 and the tubular member 1222. This ledge 1234 may help prevent a patient's fingers from slipping over the cover member 1224 when trying to pull the removable sterile barrier 1220 off of the housing 1210.

Since the housing 1210 may have a circular cross section resulting in a round exterior side surface, the drug delivery device 1202 may be susceptible to unintentionally rolling across a surface when it is placed on its side. To inhibit or prevent the drug delivery device 1202 from rolling across a surface when placed on its side, the tubular member 1222 and/or the cover member 1224 may be formed with at least one roll inhibiting exterior side surface. The at least one roll inhibiting exterior side surface may extend between proximal and distal ends of the tubular member 1222 and/or between proximal and distal ends of the cover member 1224. The at least one roll inhibiting exterior side surface of the tubular member 1222 and/or the cover member 1224 may be parallel to a longitudinal axis A of the drug delivery device 1202 and/or perpendicular to the distal end surface 1232 of the cover member 1224.

In the embodiment illustrated in FIGS. 20 and 21, the tubular member 1222 has a triangular cross section formed by three planar exterior side surfaces 1240, 1242, and 1244, and the cover member 1224 has a triangular cross section forming three planar exterior side surfaces 1250, 1252, and 1254. The cross section at issue here is the one which is perpendicular to the longitudinal axis A of the drug delivery device 1202. Each of the planar exterior side surfaces 1240, 1242, 1244, 1250, 1252, and 1254 is an example of a roll inhibiting exterior side surface. This is because each of the planar exterior side surfaces 1240, 1242, 1244, 1250, 1252, and 1254 is configured to inhibit (e.g., prevent) the removable sterile barrier 1220 and/or the drug delivery device 1202 from rolling across a support surface when the respective planar exterior side surface rests against the support surface.

As used herein, the term "planar" is hereby defined to mean flat or substantially flat. As shown in FIGS. 18 and 19, each of the planar exterior side surfaces 1240, 1242, 1244, 1250, 1252, and 1254 balloons outwardly and thus has a slight curvature. While the planar exterior side surfaces 1240, 1242, 1244, 1250, 1252, and 1254 are not exactly flat, they are nonetheless substantially flat and therefore are considered to be "planar" in accordance with principles of the present disclosure. In alternative embodiments, one or more of the planar exterior side surfaces 1240, 1242, 1244, 1250, 1252, and 1254 may be exactly flat such that it does not have any curvature. Regardless of whether the planar exterior side surfaces 31240, 1242, 1244, 1250, 1252, and 1254 have a flat configuration or a substantially flat configuration, the planar exterior side surfaces 1240, 1242, 1244, 1250, 1252, and 1254 may have the ability to inhibit (e.g., prevent) rolling of the removable sterile barrier 1220 and/or the drug delivery device 1202.

The anti-roll functionality of the removable sterile barrier 1220 may be achieved through a variety of different shapes and sizes of the tubular member 1222 and/or the cover member 1224. In some embodiments, only the tubular member 1222, or only the cover member 1224, may have a triangular cross section. Other cross-sectional shapes of the tubular member 1222 and/or the cover member 1224 are capable of preventing or inhibiting rolling including, but are not limited to, a hemisphere, a square, a rectangle, a pentagon, hexagon, or any other polygonal shape. Also, the vertices or corners formed by the one or more planar exterior side surfaces of the tubular member 1222 and/or the cover member 1224 may be rounded so that the vertices or corners are not likely to cause injury or pain to a patient while gripping the removable sterile barrier 1220.

It should be noted that the particular shape of the removable sterile barrier 1220 illustrated in FIGS. 18 and 19 is an aesthetic feature not dictated by function.

In an alternative embodiment, the drug delivery device 1202 may include a second removable sterile barrier, separate from the removable sterile barrier 1220, that attaches directly to the reservoir and surrounds the delivery cannula. In such an embodiment, the removable sterile barrier 1220 may cover and/or surround the second removable sterile barrier.

Furthermore, various electronic components of the drug delivery device 1202 may be housed (e.g., embedded) within the removable sterile barrier 1220. For example, the controller 1050, the memory 1072, the processor 1070, the communication module 1052 (e.g., a Bluetooth module, a Bluetooth Low Energy module, etc.), the skin sensor 1062, the orientation sensor 1064, the fingerprint sensor 1065, the temperature sensor 1060, the output unit 1047, and/or the input unit 1048 may be housed (e.g., embedded) within the removable sterile barrier 1220. In some embodiments, the removable sterile barrier 1220 may be configured to include one or more of the electronic elements 630-638 illustrated in FIG. 8.

The removable sterile barrier 1220 can be designed for single, one-time use, or for multiple uses. The embodiment of the removable sterile barrier 1220 illustrated in FIG. 21 may be assembled by fitting each of the C-shaped members 1228, 1230 separately around the distal end of the housing 1210 and then fixing the C-shaped members 1228, 1230 together with an adhesive. After the user removes the removable sterile barrier 1220 from the housing 1210, it may be difficult, if not impossible, to re-attach the removable sterile barrier 1220 to the housing 1210 (or the housing of another drug delivery device), at least not without breaking the C-shaped members 1228, 1230 apart and then re-fitting, and re-adhering, them around the housing 1210. As a result, the removable sterile barrier 1220 illustrated in FIG. 21 may be disposable and only for one-time use. In an alternative embodiment (not illustrated), the C-shaped members 1228, 1230 may be hinged together in a clam shell arrangement. In such an alternative embodiment, after removing the removable sterile barrier 1220 from the housing 1210, it may be possible to re-attach the removable sterile barrier 1220 to the housing 1210 (or the housing of another drug delivery device) by opening the C-shaped members 1228, 1230 like a clam shell and then fitting them around the distal end of the housing 1210. The non-hinged ends of the C-shaped members 1228, 1230 may include a locking mechanism (e.g., mating locking tabs and/or slots) so that the C-shaped members 1228, 1230 can be secured to each other after they are secured around the housing 1210. Substantial cost savings may be realized by the re-usable configuration of the removable sterile barrier 1220 since the electronics onboard the removable sterile barrier 1220 can be used more than once. In still further embodiments, the removable sterile barrier 1220 may be manufactured in one piece, and then installed axially onto the housing 1210 of the drug delivery device 1202.

Removal of the removable sterile barrier 1220 from the housing 1210 may trigger a mechanism that automatically turns on a communication module (e.g., a Bluetooth module, a Bluetooth Low Energy module, etc.), a controller, and/or other electronic components embedded within the removable sterile barrier 1220. In some embodiments, the mechanism may be similar in construction and/or operation to the switch 632 illustrated in FIG. 8. In other embodiments, such as the one illustrated in FIGS. 22 and 23, the removable sterile barrier 1220 may include a spring arm 1260 and a normally open momentary switch 1262 to achieve this functionality. The normally open momentary switch 1262 may selectively provide an electrical connection between a battery and a controller, a communication module, and/or other electronic components embedded in the removable sterile barrier 1220.

FIG. 22 illustrates a cross-sectional view of the removable sterile barrier 1220 prior to its removal from the housing 1210 of the drug delivery device 1202. The spring arm 1260 may have a first end 1264 fixed to an inner wall 1266 of the removable sterile barrier 1220, a second end 1268 moveable relative to the inner wall 1266 of the removable sterile barrier 1220, and a deflectable body portion 1270 that connects the first and second ends 1264, 1268. The deflectable body portion 1270 may protrude inwardly from the inner wall 1266. As shown in FIG. 22, the deflectable body portion 1270 may have triangular shape with its apex pointing inwardly away from the inner wall 1266. When the removable sterile barrier 1220 is disposed about the housing 1210, the housing 1210 may press against and deflect the deflectable body portion 1270 of the spring arm 1260 so that the deflectable body portion 1270 moves towards the inner wall 1266 and also downward in the distal axial direction. As a result, the second end 1268 of the spring arm 1260 may also move downward in the distal axial direction, such that it no longer contacts and depresses the normally open momentary switch 1262. Accordingly, in this configuration, the normally open momentary switch 1262 assumes an OFF position. When the normally open momentary switch 1262 is in its OFF position, as shown in FIG. 22, the controller, communication module, and/or other electronic components may not be supplied with electrical power from the battery.

FIG. 23 illustrates the removable sterile barrier 1220 after it has been removed from the housing 1210 of the drug delivery device 1202. The absence of the housing 1210 allows the deflectable body portion 1270 of the spring arm 1260 to elastically return to its un-compressed, natural shape. This causes the second end 1268 of the spring arm 1260 to move upward in the proximal axial direction until it contacts and depresses the normally open momentary switch 1262. By depressing the normally open momentary switch 1262, the second end 1268 of the spring arm 1260 causes its normally open momentary switch 1262 to assume its ON position. As a result, a controller, a communication module, and/or other electronic components embedded within the removable sterile barrier 1220 may be electrically connected to, and powered by, a battery embedded within the removable sterile barrier 1220. In some embodiments, the supplying the controller with electrical power may cause it to control the communication module to transmit a signal to an external computing device (e.g., a smartphone), via Bluetooth or Bluetooth Low Energy communication, representative of removal of the removable sterile barrier 1220 from the drug delivery device 1202.

During manufacturing, a delay may occur between the assembly of the removable sterile barrier 1220 and its installation on the housing 1210 of the drug delivery device 1202. During this delay, it may be desirable to prevent the second end 1268 of the spring arm 1260 from depressing the normally open momentary switch 1262 and turning on the electronics onboard the removable sterile barrier 1220. To address this concern, the deflectable body portion 1270 of the spring arm 1260 may be twisted so that the second end 1268 of the spring arm 1260 is not aligned with the normally open momentary switch 1262. A pin (not illustrated) may hold second end 1268 of the spring arm 1260 in this non-aligned configuration. Later, when the removable sterile barrier 1220 is fit over the housing 1210, the housing 1210 may deflect the deflectable body portion 1270 of the spring arm 1260, thereby moving the second end 1268 downward in the distal axial direction, in the manner discussed above. Accordingly, the second end 1268 will slip past the pin and the deflectable body portion 1270 will naturally un-twist itself due to its elasticity. This motion may re-align the second end 1268 of the spring arm 1260 with the normally open momentary switch 1262 so that when the removable sterile barrier 1220 is later removed from the housing 1210, the second end 1268 of the spring arm 1260 will depress the normally open momentary switch 1262 (as seen FIG. 23).

The above description describes various sensors and sensor systems which can be used in combination with a drug delivery device for detecting a condition and/or operational state of the drug delivery device. Additional or alternative sensors and sensor systems can also be incorporated in the drug delivery devices described above, including any combination of the sensors and sensor systems disclosed in the co-filed International patent application entitled "Drug Delivery System and Method of Use" and having Ser. No. 15/315,817, the entirety of which is hereby incorporated by reference.

The above description describes various systems and methods for use with a drug delivery device. It should be clear that the system, drug delivery device or methods can further comprise use of a medicament listed below with the caveat that the following list should neither be considered to be all inclusive nor limiting. The medicament will be contained in a reservoir. In some instances, the reservoir is a primary container that is either filled or pre-filled for treatment with the medicament. The primary container can be a cartridge or a pre-filled syringe.

For example, the drug delivery device or more specifically the reservoir of the device may be filled with colony stimulating factors, such as granulocyte colony-stimulating factor (G-CSF). Such G-CSF agents include, but are not limited to, Neupogen® (filgrastim) and Neulasta® (pegfilgrastim). In various other embodiments, the drug delivery device may be used with various pharmaceutical products, such as an erythropoiesis stimulating agent (ESA), which may be in a liquid or a lyophilized form. An ESA is any molecule that stimulates erythropoiesis, such as Epogen® (epoetin alfa), Aranesp® (darbepoetin alfa), Dynepo® (epoetin delta), Mircera® (methyoxy polyethylene glycol-epoetin beta), Hematide®, MRK-2578, INS-22, Retacrit® (epoetin zeta), Neorecormon® (epoetin beta), Silapo® (epoetin zeta), Binocrit® (epoetin alfa), epoetin alfa Hexal, Abseamed® (epoetin alfa), Ratioepo® (epoetin theta), Eporatio® (epoetin theta), Biopoin® (epoetin theta), epoetin alfa, epoetin beta, epoetin zeta, epoetin theta, and epoetin delta, as well as the molecules or variants or analogs thereof as disclosed in the following patents or patent applications, each of which is herein incorporated by reference in its entirety: U.S. Pat. Nos. 4,703,008; 5,441,868; 5,547,933; 5,618,698; 5,621,080; 5,756,349; 5,767,078; 5,773,569; 5,955,422; 5,986,047; 6,583,272; 7,084,245; and 7,271,689; and PCT Publication Nos. WO 91/05867; WO 95/05465; WO 96/40772; WO 00/24893; WO 01/81405; and WO 2007/136752.

An ESA can be an erythropoiesis stimulating protein. As used herein, "erythropoiesis stimulating protein" means any protein that directly or indirectly causes activation of the erythropoietin receptor, for example, by binding to and causing dimerization of the receptor. Erythropoiesis stimulating proteins include erythropoietin and variants, analogs, or derivatives thereof that bind to and activate erythropoietin receptor; antibodies that bind to erythropoietin receptor and activate the receptor; or peptides that bind to and activate erythropoietin receptor. Erythropoiesis stimulating proteins include, but are not limited to, epoetin alfa, epoetin beta, epoetin delta, epoetin omega, epoetin iota, epoetin zeta, and analogs thereof, pegylated erythropoietin, carbamylated erythropoietin, mimetic peptides (including EMP1/hematide), and mimetic antibodies. Exemplary erythropoiesis stimulating proteins include erythropoietin, darbepoetin, erythropoietin agonist variants, and peptides or antibodies that bind and activate erythropoietin receptor (and include compounds reported in U.S. Publication Nos. 2003/0215444 and 2006/0040858, the disclosures of each of which is incorporated herein by reference in its entirety) as well as erythropoietin molecules or variants or analogs thereof as disclosed in the following patents or patent applications, which are each herein incorporated by reference in its entirety: U.S. Pat. Nos. 4,703,008; 5,441,868; 5,547,933; 5,618,698; 5,621,080; 5,756,349; 5,767,078; 5,773,569;

5,955,422; 5,830,851; 5,856,298; 5,986,047; 6,030,086; 6,310,078; 6,391,633; 6,583,272; 6,586,398; 6,900,292; 6,750,369; 7,030,226; 7,084,245; and 7,217,689; U.S. Publication Nos. 2002/0155998; 2003/0077753; 2003/0082749; 2003/0143202; 2004/0009902; 2004/0071694; 2004/0091961; 2004/0143857; 2004/0157293; 2004/0175379; 2004/0175824; 2004/0229318; 2004/0248815; 2004/0266690; 2005/0019914; 2005/0026834; 2005/0096461; 2005/0107297; 2005/0107591; 2005/0124045; 2005/0124564; 2005/0137329; 2005/0142642; 2005/0143292; 2005/0153879; 2005/0158822; 2005/0158832; 2005/0170457; 2005/0181359; 2005/0181482; 2005/0192211; 2005/0202538; 2005/0227289; 2005/0244409; 2006/0088906; and 2006/0111279; and PCT Publication Nos. WO 91/05867; WO 95/05465; WO 99/66054; WO 00/24893; WO 01/81405; WO 00/61637; WO 01/36489; WO 02/014356; WO 02/19963; WO 02/20034; WO 02/49673; WO 02/085940; WO 03/029291; WO 2003/055526; WO 2003/084477; WO 2003/094858; WO 2004/002417; WO 2004/002424; WO 2004/009627; WO 2004/024761; WO 2004/033651; WO 2004/035603; WO 2004/043382; WO 2004/101600; WO 2004/101606; WO 2004/101611; WO 2004/106373; WO 2004/018667; WO 2005/001025; WO 2005/001136; WO 2005/021579; WO 2005/025606; WO 2005/032460; WO 2005/051327; WO 2005/063808; WO 2005/063809; WO 2005/070451; WO 2005/081687; WO 2005/084711; WO 2005/103076; WO 2005/100403; WO 2005/092369; WO 2006/50959; WO 2006/02646; and WO 2006/29094.

Examples of other pharmaceutical products for use with the device may include, but are not limited to, antibodies such as Vectibix® (panitumumab), Xgeva™ (denosumab) and Prolia™ (denosamab); other biological agents such as Enbrel® (etanercept, TNF-receptor/Fc fusion protein, TNF blocker), Neulasta® (pegfilgrastim, pegylated filgrastim, pegylated G-CSF, pegylated hu-Met-G-CSF), Neupogen® (filgrastim, G-CSF, hu-MetG-CSF), and Nplate® (romiplostim); small molecule drugs such as Sensipar® (cinacalcet). The device may also be used with a therapeutic antibody, a polypeptide, a protein or other chemical, such as an iron, for example, ferumoxytol, iron dextrans, ferric glyconate, and iron sucrose. The pharmaceutical product may be in liquid form, or reconstituted from lyophilized form.

Among particular illustrative proteins are the specific proteins set forth below, including fusions, fragments, analogs, variants or derivatives thereof:

OPGL specific antibodies, peptibodies, and related proteins, and the like (also referred to as RANKL specific antibodies, peptibodies and the like), including fully humanized and human OPGL specific antibodies, particularly fully humanized monoclonal antibodies, including but not limited to the antibodies described in PCT Publication No. WO 03/002713, which is incorporated herein in its entirety as to OPGL specific antibodies and antibody related proteins, particularly those having the sequences set forth therein, particularly, but not limited to, those denoted therein: 9H7; 18B2; 2D8; 2E11; 16E1; and 22B3, including the OPGL specific antibodies having either the light chain of SEQ ID NO:2 as set forth therein in FIG. 2 and/or the heavy chain of SEQ ID NO:4, as set forth therein in FIG. 4, each of which is individually and specifically incorporated by reference herein in its entirety fully as disclosed in the foregoing publication;

Myostatin binding proteins, peptibodies, and related proteins, and the like, including myostatin specific peptibodies, particularly those described in U.S. Publication No. 2004/0181033 and PCT Publication No. WO 2004/058988, which are incorporated by reference herein in their entirety particularly in parts pertinent to myostatin specific peptibodies, including but not limited to peptibodies of the mTN8-19 family, including those of SEQ ID NOS:305-351, including TN8-19-1 through TN8-19-40, TN8-19 con1 and TN8-19 con2; peptibodies of the mL2 family of SEQ ID NOS:357-383; the mL15 family of SEQ ID NOS:384-409; the mL17 family of SEQ ID NOS:410-438; the mL20 family of SEQ ID NOS:439-446; the mL21 family of SEQ ID NOS:447-452; the mL24 family of SEQ ID NOS:453-454; and those of SEQ ID NOS:615-631, each of which is individually and specifically incorporated by reference herein in their entirety fully as disclosed in the foregoing publication;

IL-4 receptor specific antibodies, peptibodies, and related proteins, and the like, particularly those that inhibit activities mediated by binding of IL-4 and/or IL-13 to the receptor, including those described in PCT Publication No. WO 2005/047331 or PCT Application No. PCT/US2004/37242 and in U.S. Publication No. 2005/112694, which are incorporated herein by reference in their entirety particularly in parts pertinent to IL-4 receptor specific antibodies, particularly such antibodies as are described therein, particularly, and without limitation, those designated therein: L1H1; L1H2; L1H3; L1H4; L1H5; L1H6; L1H7; L1H8; L1H9; L1H10; L1H11; L2H1; L2H2; L2H3; L2H4; L2H5; L2H6; L2H7; L2H8; L2H9; L2H10; L2H11; L2H12; L2H13; L2H14; L3H1; L4H1; L5H1; L6H1, each of which is individually and specifically incorporated by reference herein in its entirety fully as disclosed in the foregoing publication;

Interleukin 1-receptor 1 ("IL1-R1") specific antibodies, peptibodies, and related proteins, and the like, including but not limited to those described in U.S. Publication No. 2004/097712, which is incorporated herein by reference in its entirety in parts pertinent to IL1-R1 specific binding proteins, monoclonal antibodies in particular, especially, without limitation, those designated therein: 15CA, 26F5, 27F2, 24E12, and 10H7, each of which is individually and specifically incorporated by reference herein in its entirety fully as disclosed in the aforementioned publication;

Ang2 specific antibodies, peptibodies, and related proteins, and the like, including but not limited to those described in PCT Publication No. WO 03/057134 and U.S. Publication No. 2003/0229023, each of which is incorporated herein by reference in its entirety particularly in parts pertinent to Ang2 specific antibodies and peptibodies and the like, especially those of sequences described therein and including but not limited to: L1(N); L1(N) WT; L1(N) 1K WT; 2×L1(N); 2×L1(N) WT; Con4 (N), Con4 (N) 1K WT, 2×Con4 (N) 1K; L1C; L1C 1K; 2×L1C; Con4C; Con4C 1K; 2×Con4C 1K; Con4-L1 (N); Con4-L1C; TN-12-9 (N); C17 (N); TN8-8(N); TN8-14 (N); Con 1 (N), also including anti-Ang 2 antibodies and formulations such as those described in PCT Publication No. WO 2003/030833 which is incorporated herein by reference in its entirety as to the same, particularly Ab526; Ab528; Ab531; Ab533; Ab535; Ab536; Ab537; Ab540; Ab543; Ab544; Ab545; Ab546; A551; Ab553; Ab555; Ab558; Ab559; Ab565; AbF1AbFD; AbFE; AbFJ; AbFK; AbG1D4; AbGC1E8; AbH1C12; Ab1A1; Ab1F; Ab1K, Ab1P; and Ab1P, in their various permutations as described therein, each of which is individually and specifically incorporated by reference herein in its entirety fully as disclosed in the foregoing publication;

NGF specific antibodies, peptibodies, and related proteins, and the like including, in particular, but not limited to those described in U.S. Publication No. 2005/0074821 and U.S. Pat. No. 6,919,426, which are incorporated herein by reference in their entirety particularly as to NGF-specific antibodies and related proteins in this regard, including in particular, but not limited to, the NGF-specific antibodies therein designated 4D4, 4G6, 6H9, 7H2, 14D10 and 14D11, each of which is individually and specifically incorporated by reference herein in its entirety fully as disclosed in the foregoing publication;

CD22 specific antibodies, peptibodies, and related proteins, and the like, such as those described in U.S. Pat. No. 5,789,554, which is incorporated herein by reference in its entirety as to CD22 specific antibodies and related proteins, particularly human CD22 specific antibodies, such as but not limited to humanized and fully human antibodies, including but not limited to humanized and fully human monoclonal antibodies, particularly including but not limited to human CD22 specific IgG antibodies, such as, for instance, a dimer of a human-mouse monoclonal hLL2 gamma-chain disulfide linked to a human-mouse monoclonal hLL2 kappa-chain, including, but limited to, for example, the human CD22 specific fully humanized antibody in Epratuzumab, CAS registry number 501423-23-0;

IGF-1 receptor specific antibodies, peptibodies, and related proteins, and the like, such as those described in PCT Publication No. WO 06/069202, which is incorporated herein by reference in its entirety as to IGF-1 receptor specific antibodies and related proteins, including but not limited to the IGF-1 specific antibodies therein designated L1H1, L2H2, L3H3, L4H4, L5H5, L6H6, L7H7, L8H8, L9H9, L10H10, L11H11, L12H12, L13H13, L14H14, L15H15, L16H16, L17H17, L18H18, L19H19, L20H20, L21H21, L22H22, L23H23, L24H24, L25H25, L26H26, L27H27, L28H28, L29H29, L30H30, L31H31, L32H32, L33H33, L34H34, L35H35, L36H36, L37H37, L38H38, L39H39, L40H40, L41H41, L42H42, L43H43, L44H44, L45H45, L46H46, L47H47, L48H48, L49H49, L50H50, L51H51, L52H52, and IGF-1R-binding fragments and derivatives thereof, each of which is individually and specifically incorporated by reference herein in its entirety fully as disclosed in the foregoing publication;

Also among non-limiting examples of anti-IGF-1R antibodies for use in the methods and compositions of the present invention are each and all of those described in:

(i) U.S. Publication No. 2006/0040358 (published Feb. 23, 2006), 2005/0008642 (published Jan. 13, 2005), 2004/0228859 (published Nov. 18, 2004), including but not limited to, for instance, antibody 1A (DSMZ Deposit No. DSM ACC 2586), antibody 8 (DSMZ Deposit No. DSM ACC 2589), antibody 23 (DSMZ Deposit No. DSM ACC 2588) and antibody 18 as described therein;

(ii) PCT Publication No. WO 06/138729 (published Dec. 28, 2006) and WO 05/016970 (published Feb. 24, 2005), and Lu et al. (2004), J. Biol. Chem. 279:2856-2865, including but not limited to antibodies 2F8, A12, and IMC-A12 as described therein;

(iii) PCT Publication No. WO 07/012614 (published Feb. 1, 2007), WO 07/000328 (published Jan. 4, 2007), WO 06/013472 (published Feb. 9, 2006), WO 05/058967 (published Jun. 30, 2005), and WO 03/059951 (published Jul. 24, 2003);

(iv) U.S. Publication No. 2005/0084906 (published Apr. 21, 2005), including but not limited to antibody 7C10, chimaeric antibody C7C10, antibody h7C10, antibody 7H2M, chimaeric antibody *7C10, antibody GM 607, humanized antibody 7C10 version 1, humanized antibody 7C10 version 2, humanized antibody 7C10 version 3, and antibody 7H2HM, as described therein;

(v) U.S. Publication Nos. 2005/0249728 (published Nov. 10, 2005), 2005/0186203 (published Aug. 25, 2005), 2004/0265307 (published Dec. 30, 2004), and 2003/0235582 (published Dec. 25, 2003) and Maloney et al. (2003), Cancer Res. 63:5073-5083, including but not limited to antibody EM164, resurfaced EM164, humanized EM164, huEM164 v1.0, huEM164 v1.1, huEM164 v1.2, and huEM164 v1.3 as described therein;

(vi) U.S. Pat. No. 7,037,498 (issued May 2, 2006), U.S. Publication Nos. 2005/0244408 (published Nov. 30, 2005) and 2004/0086503 (published May 6, 2004), and Cohen, et al. (2005), Clinical Cancer Res. 11:2063-2073, e.g., antibody CP-751,871, including but not limited to each of the antibodies produced by the hybridomas having the ATCC accession numbers PTA-2792, PTA-2788, PTA-2790, PTA-2791, PTA-2789, PTA-2793, and antibodies 2.12.1, 2.13.2, 2.14.3, 3.1.1, 4.9.2, and 4.17.3, as described therein;

(vii) U.S. Publication Nos. 2005/0136063 (published Jun. 23, 2005) and 2004/0018191 (published Jan. 29, 2004), including but not limited to antibody 19D12 and an antibody comprising a heavy chain encoded by a polynucleotide in plasmid 15H12/19D12 HCA (γ4), deposited at the ATCC under number PTA-5214, and a light chain encoded by a polynucleotide in plasmid 15H12/19D12 LCF (κ), deposited at the ATCC under number PTA-5220, as described therein; and (viii) U.S. Publication No. 2004/0202655 (published Oct. 14, 2004), including but not limited to antibodies PINT-6A1, PINT-7A2, PINT-7A4, PINT-7A5, PINT-7A6, PINT-8A1, PINT-9A2, PINT-11A1, PINT-11A2, PINT-11A3, PINT-11A4, PINT-11A5, PINT-11A7, PINT-11A12, PINT-12A1, PINT-12A2, PINT-12A3, PINT-12A4, and PINT-12A5, as described therein; each and all of which are herein incorporated by reference in their entireties, particularly as to the aforementioned antibodies, peptibodies, and related proteins and the like that target IGF-1 receptors;

B-7 related protein 1 specific antibodies, peptibodies, related proteins and the like ("B7RP-1," also is referred to in the literature as B7H2, ICOSL, B7h, and CD275), particularly B7RP-specific fully human monoclonal IgG2 antibodies, particularly fully human IgG2 monoclonal antibody that binds an epitope in the first immunoglobulin-like domain of B7RP-1, especially those that inhibit the interaction of B7RP-1 with its natural receptor, ICOS, on activated T cells in particular, especially, in all of the foregoing regards, those disclosed in U.S. Publication No. 2008/0166352 and PCT Publication No. WO 07/011941, which are incorporated herein by reference in their entireties as to such antibodies and related proteins, including but not limited to antibodies designated therein as follow: 16H (having light chain variable and heavy chain variable sequences SEQ ID NO:1 and SEQ ID NO:7 respectively therein); 5D (having light chain variable and heavy chain variable sequences SEQ ID NO:2 and SEQ ID NO:9 respectively therein); 2H (having light chain variable and heavy chain variable sequences SEQ ID NO:3 and SEQ ID NO:10 respectively therein); 43H (having light chain variable and heavy chain variable sequences SEQ ID NO:6 and SEQ ID NO:14 respectively therein); 41H (having light chain variable and heavy chain variable sequences SEQ ID NO:5 and SEQ ID NO:13 respectively therein); and 15H (having light chain variable and heavy chain variable sequences SEQ ID NO:4 and SEQ ID NO:12 respectively therein), each of which is individually and specifically incorporated by reference herein in its entirety fully as disclosed in the foregoing publication;

IL-15 specific antibodies, peptibodies, and related proteins, and the like, such as, in particular, humanized monoclonal antibodies, particularly antibodies such as those disclosed in U.S. Publication Nos. 2003/0138421; 2003/023586; and 2004/0071702; and U.S. Pat. No. 7,153,507, each of which is incorporated herein by reference in its entirety as to IL-15 specific antibodies and related proteins, including peptibodies, including particularly, for instance, but not limited to, HuMax IL-15 antibodies and related proteins, such as, for instance, 146B7;

IFN gamma specific antibodies, peptibodies, and related proteins and the like, especially human IFN gamma specific antibodies, particularly fully human anti-IFN gamma antibodies, such as, for instance, those described in U.S. Publication No. 2005/0004353, which is incorporated herein by reference in its entirety as to IFN gamma specific antibodies, particularly, for example, the antibodies therein designated 1118; 1118*; 1119; 1121; and 1121*. The entire sequences of the heavy and light chains of each of these antibodies, as well as the sequences of their heavy and light chain variable regions and complementarity determining regions, are each individually and specifically incorporated by reference herein in its entirety fully as disclosed in the foregoing publication and in Thakur et al. (1999), Mol. Immunol. 36:1107-1115. In addition, description of the properties of these antibodies provided in the foregoing publication is also incorporated by reference herein in its entirety. Specific antibodies include those having the heavy chain of SEQ ID NO:17 and the light chain of SEQ ID NO:18; those having the heavy chain variable region of SEQ ID NO:6 and the light chain variable region of SEQ ID NO:8; those having the heavy chain of SEQ ID NO:19 and the light chain of SEQ ID NO:20; those having the heavy chain variable region of SEQ ID NO:10 and the light chain variable region of SEQ ID NO:12; those having the heavy chain of SEQ ID NO:32 and the light chain of SEQ ID NO:20; those having the heavy chain variable region of SEQ ID NO:30 and the light chain variable region of SEQ ID NO:12; those having the heavy chain sequence of SEQ ID NO:21 and the light chain sequence of SEQ ID NO:22; those having the heavy chain variable region of SEQ ID NO:14 and the light chain variable region of SEQ ID NO:16; those having the heavy chain of SEQ ID NO:21 and the light chain of SEQ ID NO:33; and those having the heavy chain variable region of SEQ ID NO:14 and the light chain variable region of SEQ ID NO:31, as disclosed in the foregoing publication. A specific antibody contemplated is antibody 1119 as disclosed in the foregoing U.S. publication and having a complete heavy chain of SEQ ID NO:17 as disclosed therein and having a complete light chain of SEQ ID NO:18 as disclosed therein;

TALL-1 specific antibodies, peptibodies, and the related proteins, and the like, and other TALL specific binding proteins, such as those described in U.S. Publication Nos. 2003/0195156 and 2006/0135431, each of which is incorporated herein by reference in its entirety as to TALL-1 binding proteins, particularly the molecules of Tables 4 and 5B, each of which is individually and specifically incorporated by reference herein in its entirety fully as disclosed in the foregoing publications;

Parathyroid hormone ("PTH") specific antibodies, peptibodies, and related proteins, and the like, such as those described in U.S. Pat. No. 6,756,480, which is incorporated herein by reference in its entirety, particularly in parts pertinent to proteins that bind PTH;

Thrombopoietin receptor ("TPO-R") specific antibodies, peptibodies, and related proteins, and the like, such as those described in U.S. Pat. No. 6,835,809, which is herein incorporated by reference in its entirety, particularly in parts pertinent to proteins that bind TPO-R;

Hepatocyte growth factor ("HGF") specific antibodies, peptibodies, and related proteins, and the like, including those that target the HGF/SF:cMet axis (HGF/SF:c-Met), such as the fully human monoclonal antibodies that neutralize hepatocyte growth factor/scatter (HGF/SF) described in U.S. Publication No. 2005/0118643 and PCT Publication No. WO 2005/017107, huL2G7 described in U.S. Pat. No. 7,220,410 and OA-5d5 described in U.S. Pat. Nos. 5,686,292 and 6,468,529 and in PCT Publication No. WO 96/38557, each of which is incorporated herein by reference in its entirety, particularly in parts pertinent to proteins that bind HGF;

TRAIL-R2 specific antibodies, peptibodies, related proteins and the like, such as those described in U.S. Pat. No. 7,521,048, which is herein incorporated by reference in its entirety, particularly in parts pertinent to proteins that bind TRAIL-R2;

Activin A specific antibodies, peptibodies, related proteins, and the like, including but not limited to those described in U.S. Publication No. 2009/0234106, which is herein incorporated by reference in its entirety, particularly in parts pertinent to proteins that bind Activin A;

TGF-beta specific antibodies, peptibodies, related proteins, and the like, including but not limited to those described in U.S. Pat. No. 6,803,453 and U.S. Publication No. 2007/0110747, each of which is herein incorporated by reference in its entirety, particularly in parts pertinent to proteins that bind TGF-beta;

Amyloid-beta protein specific antibodies, peptibodies, related proteins, and the like, including but not limited to those described in PCT Publication No. WO 2006/081171, which is herein incorporated by reference in its entirety, particularly in parts pertinent to proteins that bind amyloid-beta proteins. One antibody contemplated is an antibody having a heavy chain variable region comprising SEQ ID NO:8 and a light chain variable region having SEQ ID NO:6 as disclosed in the foregoing publication;

c-Kit specific antibodies, peptibodies, related proteins, and the like, including but not limited to those described in U.S. Publication No. 2007/0253951, which is incorporated herein by reference in its entirety, particularly in parts pertinent to proteins that bind c-Kit and/or other stem cell factor receptors;

OX40L specific antibodies, peptibodies, related proteins, and the like, including but not limited to those described in U.S. Publication No. 2006/0002929, which is incorporated herein by reference in its entirety, particularly in parts pertinent to proteins that bind OX40L and/or other ligands of the OX40 receptor; and Other exemplary proteins, including Activase® (alteplase, tPA); Aranesp® (darbepoetin alfa); Epogen® (epoetin alfa, or erythropoietin); GLP-1, Avonex® (interferon beta-1a); Bexxar® (tositumomab, anti-CD22 monoclonal antibody); Betaseron® (interferon-beta); Campath® (alemtuzumab, anti-CD52 monoclonal antibody); Dynepo® (epoetin delta); Velcade® (bortezomib); MLN0002 (anti-α4β7 mAb); MLN1202 (anti-CCR2 chemokine receptor mAb); Enbrel® (etanercept, TNF-receptor/Fc fusion protein, TNF blocker); Eprex® (epoetin alfa); Erbitux® (cetuximab, anti-EGFR/HER1/c-ErbB-1); Genotropin® (somatropin, Human Growth Hormone); Herceptin® (trastuzumab, anti-HER2/neu (erbB2) receptor mAb); Humatrope® (somatropin, Human Growth Hormone); Humira® (adalimumab); insulin in solution; Infergen® (interferon alfacon-1); Natrecor®

(nesiritide; recombinant human B-type natriuretic peptide (hBNP); Kineret® (anakinra); Leukine® (sargamostim, rhuGM-CSF); LymphoCide® (epratuzumab, anti-CD22 mAb); Benlysta™ (lymphostat B, belimumab, anti-BlyS mAb); Metalyse® (tenecteplase, t-PA analog); Mircera® (methoxy polyethylene glycol-epoetin beta); Mylotarg® (gemtuzumab ozogamicin); Raptiva® (efalizumab); Cimzia® (certolizumab pegol, CDP 870); Soliris™ (eculizumab); pexelizumab (anti-C5 complement); Numax® (MEDI-524); Lucentis® (ranibizumab); Panorex® (17-1A, edrecolomab); Trabio® (lerdelimumab); TheraCim hR3 (nimotuzumab); Omnitarg (pertuzumab, 2C4); Osidem® (IDM-1); OvaRex® (B43.13); Nuvion® (visilizumab); cantuzumab mertansine (huC242-DM1); NeoRecormon® (epoetin beta); Neumega® (oprelvekin, human interleukin-11); Neulasta® (pegylated filgastrim, pegylated G-CSF, pegylated hu-Met-G-CSF); Neupogen® (filgrastim, G-CSF, huMetG-CSF); Orthoclone OKT3® (muromonab-CD3, antiCD3 monoclonal antibody); Procrit® (epoetin alfa); Remicade® (infliximab, anti-TNFα monoclonal antibody); Reopro® (abciximab, anti-GP llb/IIia receptor monoclonal antibody); Actemra® (anti-IL6 Receptor mAb); Avastin® (bevacizumab), HuMax-CD4 (zanolimumab); Rituxan® (rituximab, anti-CD20 mAb); Tarceva® (erlotinib); Roferon-A®-(interferon alfa-2a); Simulect® (basiliximab); Prexige® (lumiracoxib); Synagis® (palivizumab); 146B7-CHO (anti-IL15 antibody, see U.S. Pat. No. 7,153,507); Tysabri® (natalizumab, anti-α4integrin mAb); Valortim® (MDX-1303, anti-*B. anthracis* protective antigen mAb); ABthrax™; Vectibix® (panitumumab); Xolair® (omalizumab); ETI211 (anti-MRSA mAb); IL-1 trap (the Fc portion of human IgG1 and the extracellular domains of both IL-1 receptor components (the Type I receptor and receptor accessory protein)); VEGF trap (Ig domains of VEGFR1 fused to IgG1 Fc); Zenapax® (daclizumab); Zenapax® (daclizumab, anti-IL-2Ra mAb); Zevalin® (ibritumomab tiuxetan); Zetia® (ezetimibe); Orencia® (atacicept, TACI-Ig); anti-CD80 monoclonal antibody (galiximab); anti-CD23 mAb (lumiliximab); BR2-Fc (huBR3/huFc fusion protein, soluble BAFF antagonist); CNTO 148 (golimumab, anti-TNFα mAb); HGS-ETR1 (mapatumumab; human antiTRAIL Receptor-1 mAb); HuMax-CD20 (ocrelizumab, anti-CD20 human mAb); HuMax-EGFR (zalutumumab); M200 (volociximab, anti-α5β1 integrin mAb); MDX-010 (ipilimumab, anti-CTLA-4 mAb and VEGFR-1 (IMC-18F1); anti-BR3 mAb; anti-*C. difficile* Toxin A and Toxin B C mAbs MDX-066 (CDA-1) and MDX-1388); anti-CD22 dsFv-PE38 conjugates (CAT-3888 and CAT-8015); antiCD25 mAb (HuMax-TAC); anti-CD3 mAb (NI-0401); adecatumumab; anti-CD30 mAb (MDX-060); MDX-1333 (anti-IFNAR); anti-CD38 mAb (HuMax CD38); antiCD40L mAb; anti-Cripto mAb; anti-CTGF Idiopathic Pulmonary Fibrosis Phase I Fibrogen (FG-3019); anti-CTLA4 mAb; anti-eotaxin1 mAb (CAT-213); anti-FGF8 mAb; antiganglioside GD2 mAb; anti-ganglioside GM2 mAb; antiGDF-8 human mAb (MYO-029); anti-GM-CSF Receptor mAb (CAM-3001); anti-HepC mAb (HuMax HepC); antiIFNα mAb (MEDI-545, MDX-1103); anti-IGF1R mAb; anti-IGF-1R mAb (HuMax-Inflam); anti-IL12 mAb (ABT-874); anti-IL12/IL23 mAb (CNTO 1275); anti-IL13 mAb (CAT-354); anti-IL2Ra mAb (HuMax-TAC); anti-IL5 Receptor mAb; anti-integrin receptors mAb (MDX-018, CNTO 95); anti-IP10 Ulcerative Colitis mAb (MDX-1100); anti-LLY antibody; BMS-66513; anti-Mannose Receptor/hCGβ mAb (MDX-1307); anti-mesothelin dsFv-PE38 conjugate (CAT-5001); anti-PD1mAb (MDX-1106 (ONO-4538)); anti-PDGFRα antibody (IMC-3G3); anti-TGFβ mAb (GC-1008); anti-TRAIL Receptor-2 human mAb (HGS-ETR2); anti-TWEAK mAb; anti-VEGFR/Flt-1 mAb; anti-ZP3 mAb (HuMax-ZP3); NVS Antibody #1; and NVS Antibody #2.

Also included can be a sclerostin antibody, such as but not limited to romosozumab, blosozumab, or BPS 804 (Novartis). Further included can be therapeutics such as rilotumumab, bixalomer, trebananib, ganitumab, conatumumab, motesanib diphosphate, brodalumab, vidupiprant, panitumumab, denosumab, NPLATE, PROLIA, VECTIBIX or XGEVA. Additionally, included in the device can be a monoclonal antibody (IgG) that binds human Proprotein Convertase Subtilisin/Kexin Type 9 (PCSK9), e.g. U.S. Pat. No. 8,030,547, U.S. Publication No. 2013/0064825, WO2008/057457, WO2008/057458, WO2008/057459, WO2008/063382, WO2008/133647, WO2009/100297, WO2009/100318, WO2011/037791, WO2011/053759, WO2011/053783, WO2008/125623, WO2011/072263, WO2009/055783, WO2012/0544438, WO2010/029513, WO2011/111007, WO2010/077854, WO2012/088313, WO2012/101251, WO2012/101252, WO2012/101253, WO2012/109530, and WO2001/031007.

Also included can be talimogene laherparepvec or another oncolytic HSV for the treatment of melanoma or other cancers. Examples of oncolytic HSV include, but are not limited to talimogene laherparepvec (U.S. Pat. Nos. 7,223,593 and 7,537,924); OncoVEXGALV/CD (U.S. Pat. No. 7,981,669); OrienX010 (Lei et al. (2013), World J. Gastroenterol., 19:5138-5143); G207, 1716; NV1020; NV12023; NV1034 and NV1042 (Vargehes et al. (2002), Cancer Gene Ther., 9(12):967-978).

Also included are TIMPs. TIMPs are endogenous tissue inhibitors of metalloproteinases (TIMPs) and are important in many natural processes. TIMP-3 is expressed by various cells or and is present in the extracellular matrix; it inhibits all the major cartilage-degrading metalloproteases, and may play a role in role in many degradative diseases of connective tissue, including rheumatoid arthritis and osteoarthritis, as well as in cancer and cardiovascular conditions. The amino acid sequence of TIMP-3, and the nucleic acid sequence of a DNA that encodes TIMP-3, are disclosed in U.S. Pat. No. 6,562,596, issued May 13, 2003, the disclosure of which is incorporated by reference herein. Description of TIMP mutations can be found in U.S. Publication No. 2014/0274874 and PCT Publication No. WO 2014/152012.

Also included are antagonistic antibodies for human calcitonin gene-related peptide (CGRP) receptor and bispecific antibody molecule that target the CGRP receptor and other headache targets. Further information concerning these molecules can be found in PCT Application No. WO 2010/075238.

Additionally, a bispecific T cell engager antibody (BiTe), e.g. Blinotumomab can be used in the device. Alternatively, included can be an APJ large molecule agonist e.g., apelin or analogues thereof in the device. Information relating to such molecules can be found in PCT Publication No. WO 2014/099984.

In certain embodiments, the medicament comprises a therapeutically effective amount of an anti-thymic stromal lymphopoietin (TSLP) or TSLP receptor antibody. Examples of anti-TSLP antibodies that may be used in such embodiments include, but are not limited to, those described in U.S. Pat. Nos. 7,982,016, and 8,232,372, and U.S. Publication No. 2009/0186022. Examples of anti-TSLP receptor antibodies include, but are not limited to, those described in U.S. Pat. No. 8,101,182. In particularly preferred embodiments, the medicament comprises a therapeutically effective amount of the anti-TSLP antibody designated as A5 within U.S. Pat. No. 7,982,016.

It should be noted that the configurations of the various embodiments of the drug delivery devices and drug delivery systems described herein are illustrative only. Although only a few embodiments of the of the drug delivery devices and drug delivery systems have been described in detail in this disclosure, those skilled in the art who review this disclosure will readily appreciate that many modifications are possible (e.g., variations in sizes, dimensions, structures, shapes and proportions of the various elements, values of parameters, mounting arrangements, use of materials, orientations, etc.) without materially departing from the novel teachings and advantages of the subject matter of this disclosure. For example, any combination of one or more of the sensors and/or controllable elements described herein may be incorporated into one or more of the drug delivery systems and drug delivery devices described herein. Also, the order or sequence of any process or method steps described herein may be varied or re-sequenced, in any combination, according to alternative embodiments. Furthermore, any combination of one or more of the elements of one or more of the claims set forth at the end of this disclosure is possible.

Although the preceding text sets forth a detailed description of different embodiments of the invention, it should be understood that the legal scope of the invention is defined by the words of the claims set forth at the end of this patent. The detailed description is to be construed as exemplary only and does not describe every possible embodiment of the invention because describing every possible embodiment would be impractical, if not impossible. Numerous alternative embodiments could be implemented, using either current technology or technology developed after the filing date of this patent, that would still fall within the scope of the claims defining the invention.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, sixth paragraph.

What is claimed is:

1. A drug delivery system comprising:
   a drug delivery device comprising
      a reservoir,
      a delivery cannula having a proximal end in fluid communication with the reservoir during use of the drug delivery device and a distal end to be received within a patient during use of the drug delivery device,
      a removable sterile barrier, and
      a lock;
   a sensor coupled to the drug delivery device and configured to detect movement of the removable sterile barrier; and
   a controller coupled to the sensor and the lock, the controller being configured to:
      use the sensor to determine if the removable sterile barrier has been removed from the drug delivery device prior to use of the drug delivery device, and
      activate the lock to have a locked state or maintain the lock in the locked state if the removable sterile barrier has been removed from the drug delivery device prior to use of the drug delivery device.

2. The drug delivery system of claim 1, comprising an output unit coupled to the controller, wherein
   the controller is configured to:
      (a) activate the output unit if the removable sterile barrier has not been removed from the drug delivery device prior to use of the drug delivery device,
      (b) use the sensor to determine if the removable sterile barrier has been removed from the drug delivery device subsequent to (a),
      (c) determine if a time period has elapsed since removal of the removable sterile barrier, and
      (d) activate the lock to have the locked state if the removable sterile barrier has been removed from the drug delivery device and the time period has elapsed.

3. The drug delivery system of claim 1, comprising a circuit having a low-energy state and a high-energy state.

4. The drug delivery system of claim 3, wherein the controller is configured to:
   (a) determine if the drug delivery device is ready for use,
   (b) use the sensor to determine if the removable sterile barrier has been removed from the drug delivery device subsequent to (a), and
   (c) switch the circuit from the low-energy state to the high-energy state if the removable sterile barrier has been removed from the drug delivery device.

5. The drug delivery system of claim 1, comprising a heating element configured to heat a medicament in the reservoir or the delivery cannula when activated.

6. The drug delivery system of claim 5, comprising an output unit coupled to the controller, wherein the controller is configured to:
   (a) activate the output unit if the removable sterile barrier has not been removed from the drug delivery device prior to use of the drug delivery device,
   (b) use the sensor to determine if the removable sterile barrier has been removed from the drug delivery device subsequent to (a), and
   (c) activate the heating element if the removable sterile barrier has been removed from the drug delivery device.

7. The drug delivery system of claim 1, the drug delivery device comprising:
   a housing containing the reservoir and the delivery cannula; and
   the removable sterile barrier disposed about a distal end of the housing, the removable sterile barrier having at least one roll inhibiting exterior side surface.

8. The drug delivery system of claim 7, the removable sterile barrier having a triangular cross section.

9. The drug delivery system of claim 7, the removable sterile barrier having a planar distal end surface, the at least one roll inhibiting exterior side surface being perpendicular to the planar distal end surface.

10. The drug delivery system of claim 7, the removable sterile barrier including a cover member and a tubular member, the cover member covering an open end of the tubular member, the tubular member including a plurality of outwardly protruding ribs to be gripped by the patient when removing the removable sterile barrier from the housing.

11. The drug delivery system of claim 7, at least one of the controller or the sensor being housed within the removable sterile barrier.

12. The drug delivery system of claim 1, the drug delivery device comprising:
   a controllable element;
   a memory configured to store identity information representative of at least one of an identity of the patient, an identity of the drug delivery device, or an identity of a medicament to be stored within the reservoir; and
   wherein the controller is coupled to the memory and the controllable element, the controller being configured to control the controllable element based on the identity information.

13. The drug delivery system of claim 12,
   the removable sterile barrier having at least one roll inhibiting exterior side surface.

14. The drug delivery system of claim 13, the removable sterile barrier having a planar distal end surface, the at least one roll inhibiting exterior side surface being perpendicular to the planar distal end surface.

15. The drug delivery system of claim 13, the removable sterile barrier including a cover member and a tubular member, the cover member covering an open end of the tubular member, the tubular member including a plurality of outwardly protruding ribs to be gripped by the patient when removing the removable sterile barrier from the housing.

16. The drug delivery system of claim 1, wherein the removable sterile barrier is disposed about the distal end of the delivery cannula.

* * * * *

UNITED STATES PATENT AND TRADEMARK OFFICE
CERTIFICATE OF CORRECTION

Page 1 of 1

PATENT NO. : 10,646,652 B2
APPLICATION NO. : 15/315829
DATED : May 12, 2020
INVENTOR(S) : McCullough et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 149 days.

Signed and Sealed this
Seventh Day of September, 2021

Drew Hirshfeld
*Performing the Functions and Duties of the*
*Under Secretary of Commerce for Intellectual Property and*
*Director of the United States Patent and Trademark Office*